United States Patent [19]

Ohno et al.

[11] Patent Number: 5,798,211
[45] Date of Patent: Aug. 25, 1998

[54] **PROBE FOR DIAGNOSING *PSEUDOMONAS AERUGINOSA***

[75] Inventors: Tsuneya Ohno, 15-16, Kita-Aoyama 3 chome, Minato-ku, Tokyo 107; Akio Matsuhisa, Nara; Hirotsugu Uehara, Kobe; Soji Eda, Higashi-Osaka, all of Japan

[73] Assignees: Tsuneya Ohno, Tokyo; Fuso Pharmaceuticals, Ltd., Osaka, both of Japan

[21] Appl. No.: 921,177

[22] Filed: Aug. 29, 1997

Related U.S. Application Data

[62] Division of Ser. No. 362,577, Mar. 27, 1995.

[30] Foreign Application Priority Data

Jul. 7, 1995 [JP] Japan .................................... 4-179719

[51] Int. Cl.$^6$ .............................. C12Q 1/68; C07H 21/04
[52] U.S. Cl. ...................... 435/6; 536/24.32; 536/24.33; 935/8; 935/9; 935/78
[58] Field of Search ............................ 435/6; 536/24.32, 536/24.33; 935/8, 9, 78

[56] References Cited

PUBLICATIONS

Loutit et al. Journal of Clinical Microbiology. 29(12): 2897–2900, Dec. 1991.

Alberts et al., *Molecular Biology of the Cell*, Second Edition, Garland Publishing Inc., New York, NY, pp. 182 and 188–193 (1989).

Bell, et al., "The Nucleotide Sequences of the rbsD, rbsA, and rbsC Genes of *Escherichia coli* K12", *The Journal of Biological Chemistry* 261(17):7652–7658 (Jun. 1986).

Betzl, et al., "Identification of Lactococci and Enterococci by Colony Hybridization with 23S rRNA–Targeted Oligonucleotide Probes", *Applied and Environmental Microbiology:* 56(9):2927–2929 (Sep. 1990).

Buckel, et al., "An Analysis of the Structure of the Product of the rbsA Gene of *Escherichia coli* D12", *The Journal of Biological Chemistry* 261(17):7659–7662 (Jun. 1986).

Cano et al., *Microbiology*, West Publishing Company, Minneapolis, MN, pp. 264–268, 279, 293, 296, 297, and 801 (1986).

Davis, et al., "Direct Identification of Bacterial Isolates in Blood Cultures by Using a DNA Probe", *Journal of Clinical Microbiology* 29(10):2193–2196 (Oct. 1991).

De Buyser, et al., "Evaluation of a ribosomal RNA gene probe for the identification of species and subspecies within the genus Staphylococcus", *Journal of General Microbiology* 138:889–899 (1992).

Gerberding et al., Antimicrobial Agents and Chemotherapy 35(12):2574–2579 (1991).

Groarke, et al., "The Amino Acid Sequence of D-Ribose–binding Protein from *Escherichia coli* K12", *The Journal of Biological Chemistry* 258(21): 12952–12956 (Jun. 1983).

Hall, et al., "Typing of Enterococcus Species by DNA Restriction Fragment Analysis", *Journal of Clinical Microbiology* 30(4):915–919, (Apr. 1992).

Hope, et al., "Ribokinase from *Escherichia coli* K12", *The Journal of Biological Chemistry* 261(17):7663–7668 (Jun. 1986).

Joffee, et al., "Epidemiologic Studies of Nosocomial Infections with *Pseudomonas aeruginosa* Using a DNA Probe", *Abstracts of the Annual Meeting:*485 (1989).

Lehninger, A.L., *Principles of Biochemistry*, Worth Publishers, Inc., New York, pp. 809–811 (1982).

(List continued on next page.)

*Primary Examiner*—Carla J. Myers
*Attorney, Agent, or Firm*—Marshall, O'Toole, Gerstein, Murray & Borun

[57] ABSTRACT

DNA probes for diagnosing infectious diseases involving *Pseudomonas aeruginosa* and methods of using such probes are provided.

2 Claims, 6 Drawing Sheets

PUBLICATIONS

Maniatis et al., *Molecular Cloning: A Laboratory Manual*, Cold Spring Harbor Laboratory, Cold Spring Harbor, NY, pp. 309–330, 374 and 375 (1982).

Sambrook et al., *Molecular Cloning : A Laboratory Manual*, Second Edition, Cold Spring Harbor Laboratory Press, Cold Spring Harbor, NY, pp. 5.10, 5.11, and 12.21–12.23 (1989).

Smith et al., *Principles of Biochemistry: General Aspects*, Seventh Edition, McGraw–Hill Book Company, New York, NY, p. 723 (1983).

Tredget, et al., "Epidemiology of Infections with *Pseudomonas aeruginose* in Burn Patients: The Role of Hydrotherapy", *Clinical Infectious Diseases 15:*941–949, (1992).

Watson et al., *Molecular Biology of the Gene*, Fourth Edition, The Benjamin/Cummings Publishing Company, Inc. Menlo Park, CA, pp. 89, 208–210, and 608 (1987).

Watson et al., *Recombinant DNA: A Short Course*, Scientific American Books, USA, pp. 58–60 (1983).

PROBE FOR DIAGNOSING *PSEUDOMONAS AERUGINOSA*

This is a Divisional of U.S. application Ser. No. 08/362/577, filed Mar. 27, 1995.

[TECHNICAL FIELD]

The present invention relates to probes, prepared by making use of causative bacteria of infectious diseases, which are useful for detecting and identifying the causative bacteria.

[BACKGROUND ART]

In pathology, infection is defined as invasion and establishment of a foothold for growth in an organism by a pathogenic organism (hereinafter referred to as "bacteria"), then the outbreak of disease depends upon the interrelationship between the resistance of host and the virulence of bacteria.

In the infectious diseases, improvement in treatment methods of bateremia have been raised as an important issue. That is to say, bacteremia is not a disease caused by a particular bacterium, but is caused by emergence and habitancy of the various bacteria in blood, then onset thereof is clinically suspected when fever of about 40° C. persists for two or more days. If a patient is an infant or is suffering from terminal cancer with weakened resistance, the patient may die in one or two days, therefore, the bacteremia is a serious and urgent disease, and the improvement in treatment methods thereof have been awaited.

In the infectious disease, phagocytes including neutrophils, monocytes and macrophages primarily work in defense of the body. Emergence of bacteria in the blood is thought as invasion of predominant bacteria which have emerged from the tissue of the phagocyte.

Bacteremia is a state wherein the bacteria is emerged into the blood, and a large amount of antibiotic is administrated to treat it wherein the causative bacteria is sensitive to the antibiotic. Generally, since antibiotics lower the functions of the internal organs such as liver, it is necessary to pay an attention to reduce an administration of an ineffective antibiotic to a patient in a serious state.

When bacteremia is defined as a case wherein phagocytesis of cells can not overcome the virulence of bacteria, then the bacteria spread in the body through the blood, bacteremia with serious symptoms due to toxins produced by the bacteria is called as sepsis. Proof of sepsis, in the other word, establishment of the diagnosis requires a check on the items of 1) clinical symptoms, 2) culturing of specimen, 3) gram-staining of the bacteria contained in the specimen, and 4) shock state, then, upon completing the check of these items, the treatment method is determined. Accordingly, to quickly and reliably identify the bacteria have been awaited in the art.

In the present method for detecting and identifying bacteria in a bacteremia-specimen, it is a common procedure to identify in selective medium a specimen which have positive signal in a routine process of culture bottle. However, to successfuly culture the bacteria from these blood specimen is quite difficult, then, if a large dose of antibiotics is administrated when bacteremia was suspected, bacteria in the blood will not be cultured and grown in many cases, therefore, the rate of culture bottle positive case become extremely low.

Although available sub-routine methods include instrumental analysis of constituents and metabolic products of bacteria (Yoshimi Benno, "Quick identification of bacteria with gas chromatography", Rinsho Kensa, Vol. 29, No.12, November 1985, Igaku Shoin ed.), a method utilizing specific antibody (Japanese Patent Provisional Publication No. 60-224068), and a hybridization method utilizing specificity of DNA (Japanese Phase Patent Provisional Publication No. 61-502376) have been developed, any of which are required to separate the bacteria and culture it. On the other hand, as a method established based on the function of phagocytes in infectious diseases, there is a method to examine, under an optical microscope, a stained smear of buffy coat wherein leukocyte of the blood sample is concentrated. Generally speaking, although the rate of detection of bacteria in buffy coat specimens from adult bacteremia patients is 30% at most, which is similar to that in earlobe blood specimens, it was reported that bacteria had been detected in seven cases of ten cases (70%) in newborn patients, therefore, an information concerning the presence of a bacteria in peripheral blood to be obtained by microscope examination on smear is an important for treatment.

Since the conventional methods necessiate the pretreatment which requires at least three to four days in total containing one to two day(s) for selective isolation of bacteria from a specimen, one day for cultivation, and one or more day(s) for fixation, and the culture thereof is continued in practice until the bacteria grow, the culture will needs one week or more even for C.B.-positive cases, therefore, this was a factor in high mortality of C.B.-positive patients being treated by the conventional methods. For example, according to the a report published in "The Journal of the Japanese Association for Infectious Diseases", Vol. 58, No. 2, p. 122, 1984, even though the blood culture positive rate was 28.6% (163 cases/569 cases), the mortality was as high as 84.6% (138 cases/163 cases).

Further, it may be impossible to distinguish contamination at the cultivation by indigenous bacteria. For example, *Staphylococcus epidermides*, which is one of Staphylococci and is the causative bacterium of bacteremia, stayed in the skin of the normal person, then, there is a risk on contamination of a specimen with this bacterium when a needle is inserted into the skin.

As an important matter, under such circumstances above, since many bacteria in a specimen to be cultured have been incorporated into said phagocyte and are dead or stationary immobilized, the number of growable bacteria is small even under appropriate conditions for cultivation, thereby, the actual detection rate of bacteria through culture specimen is as low as about 10%. In the other word, at this moment, 90% of the examined blood, which have been cultured for further one or more day(s), of the patient suspected clinically as suffering with bacteremia can not clarify the presence of bacteria.

In light of the situation above, the present practice depends on a treatment to be started when bacteremia is clinically suspected without awaiting the detection results, that is to say, a trial and error method wherein an antibiotic having broad spectrum is administrated first, and if the antibiotic is not effective after one or two day(s), another antibiotic will be tried.

According to the method to stain the bacteria in the specimen, the constituents of the living body are also stained together with bacteria, therefore, experience to quickly identify bacteria according to thier image through microscope is required, then there may be cases that can be hardly diagnosed as bacteremia.

Although bacteremia is a disease wherein a rapid and exact diagnosis have been required, the conventional diagnosis method can not respond to such requirements.

[DISCLOSURE OF THE INVENTION]

The present invention was established in view of the problems in the art, and is directed to a probe having a specific reactivity with DNA or RNA obtained from primary causative bacteria of the infectious diseases, then provide a genetic information by analyzing the base sequence of DNA in the probe.

By the probe of the present invention, for example, a causative bacteria of the infectious diseases is detected rapidly and exactly, without cultivating/proliferating the bacteria, through a detection of DNA held in the causative bacteria digested and incorporated gradually with the phagocyte. Then, if primers are designed by referring to an information on base sequence of these probes, causative bacteria can identify, without the hybridization, by amplifying the DNA with PCR technique.

When non-radioactive probe, for example, biotinylated probe is used for hybridization, since such probe can be detected with an optical microscope in a conventional laboratory without radio isotope handling facilities, the detection process would be rapid and simple.

[BEST MODE FOR CARRYING OUT THE INVENTION]

Figure 1:
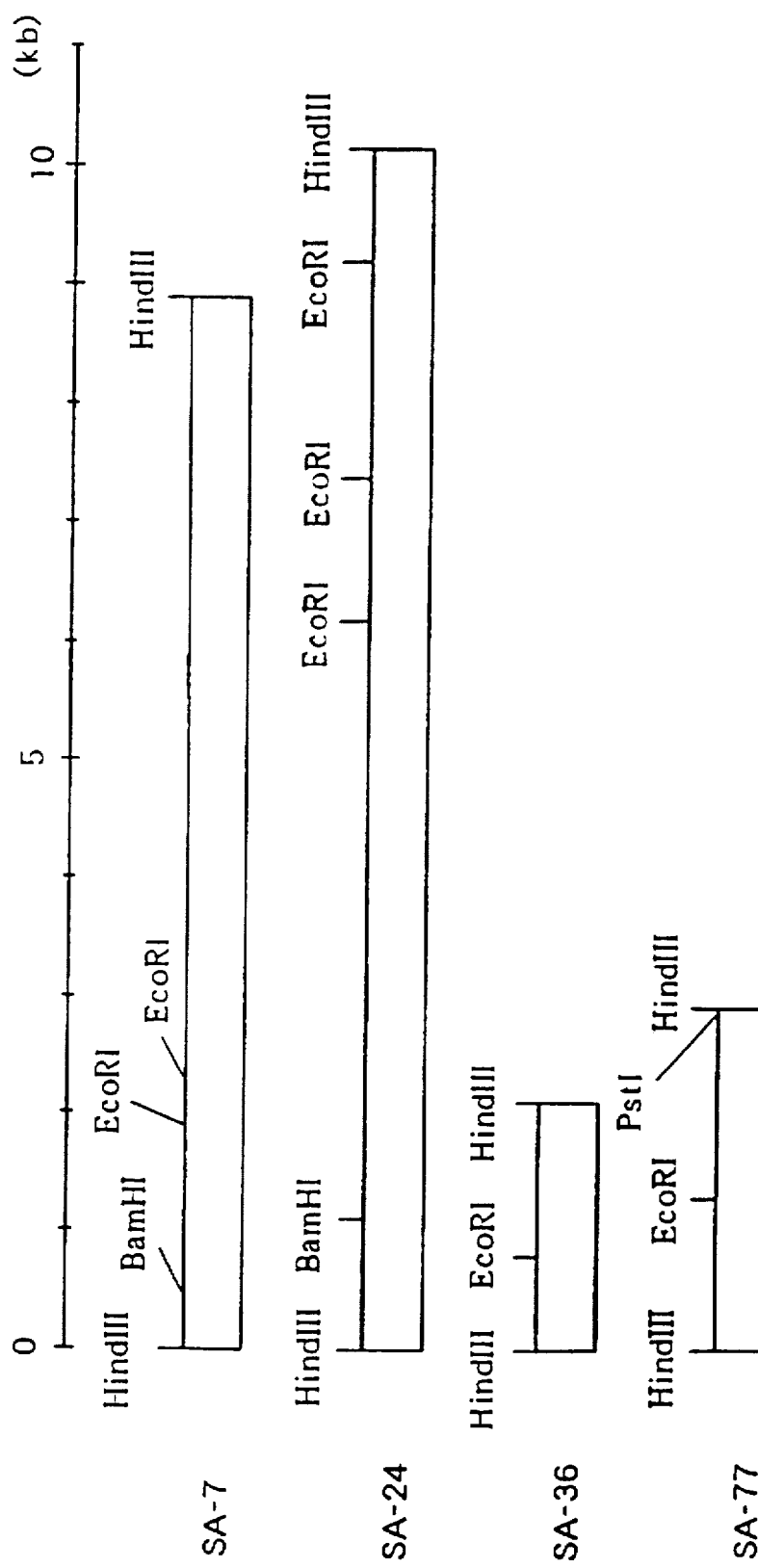
FIG. 1 is a restriction enzyme map of HindIII fragment on probe for detecting *Staphylococcus aureus*.
Figure 2:
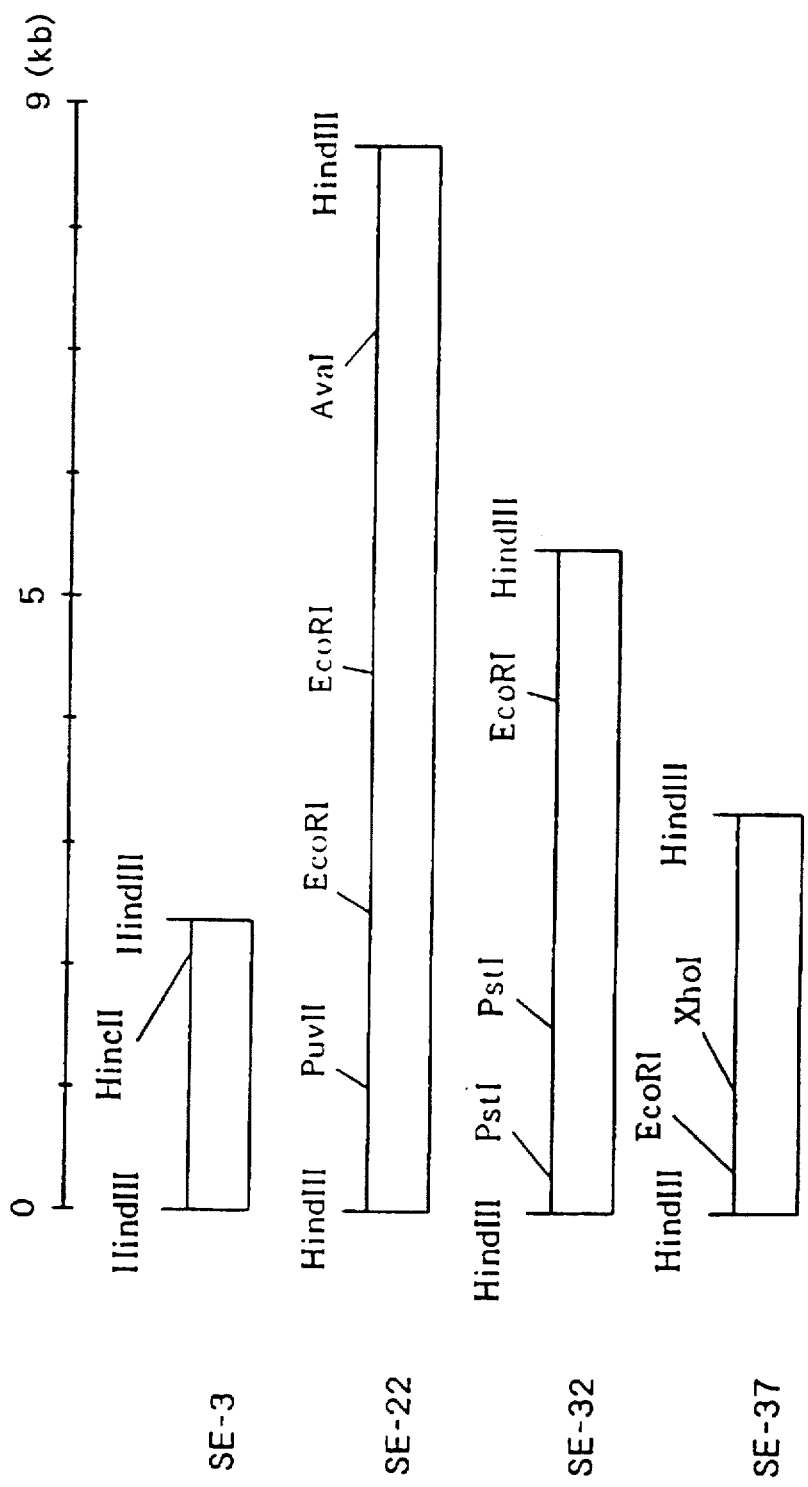
FIG. 2 is a restriction enzyme map of HindIII fragment on probe for detecting *Staphylococcus epidermidis*.
Figure 3:
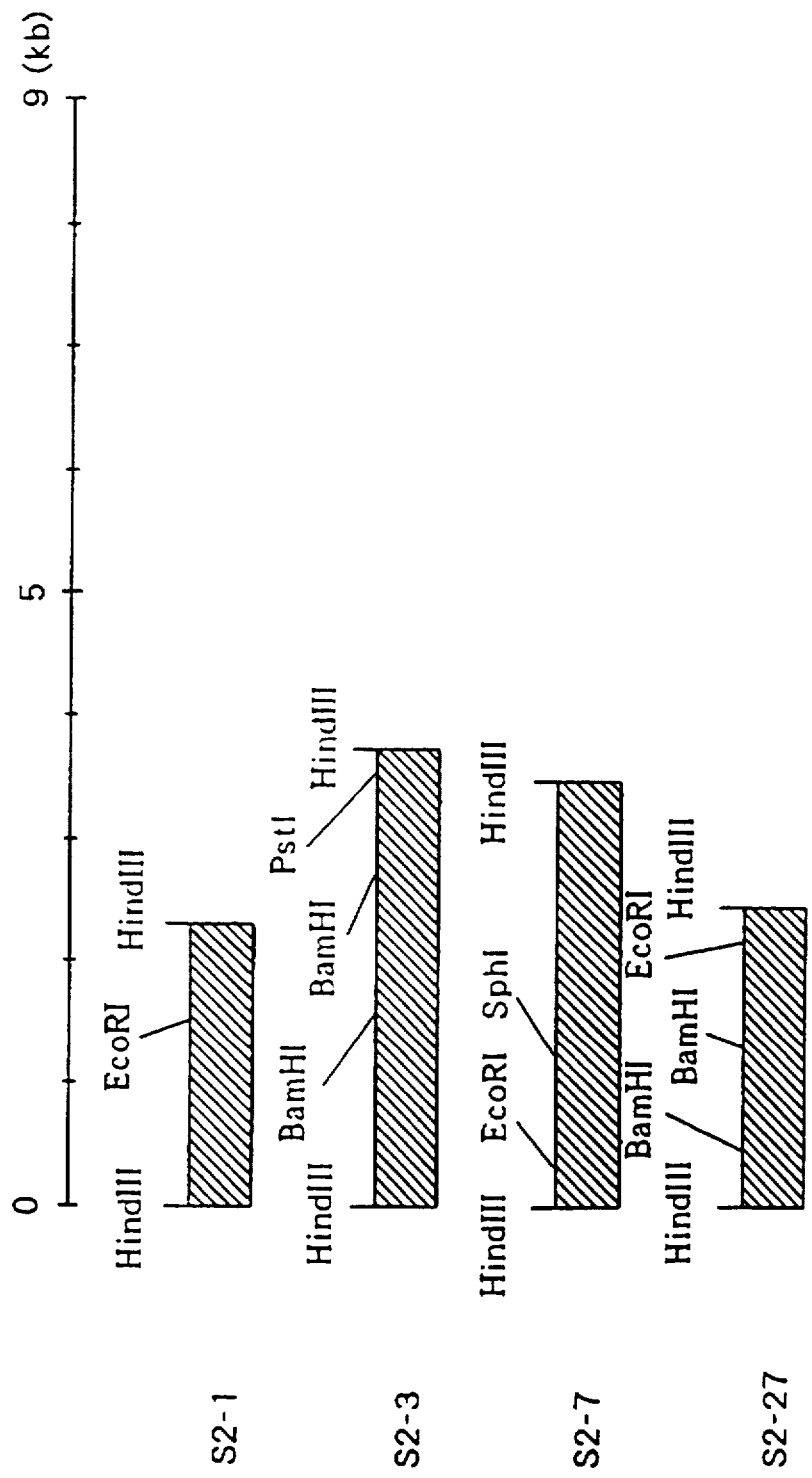
FIG. 3 is a restriction enzyme map of HindIII fragment on probe for detecting *Enterococcus faecalis*.
Figure 4:
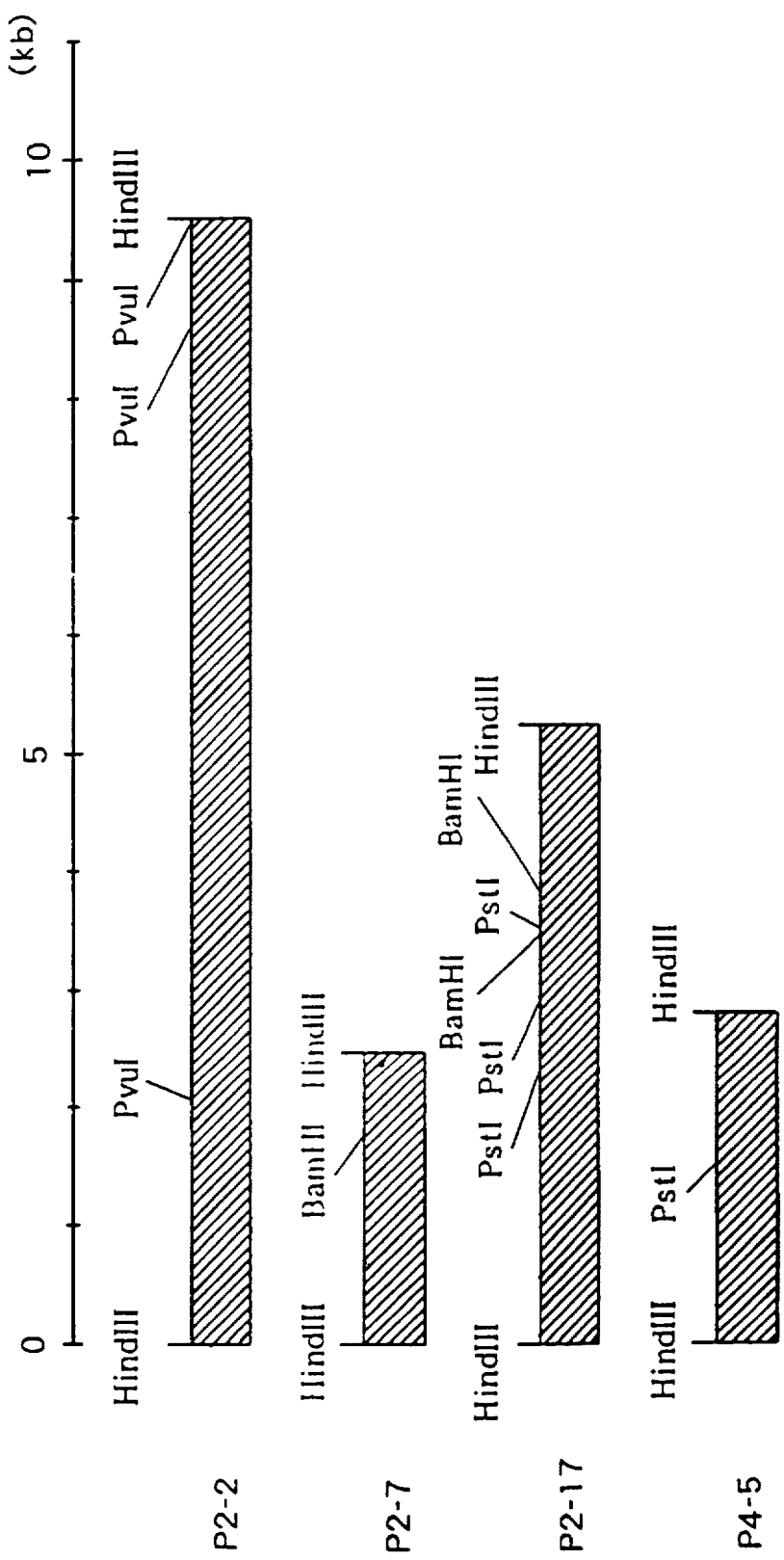
FIG. 4 is a restriction enzyme map of HindIII fragment on probe for detecting *Pseudomonas aeruginosa*.

Examples on probes prepared from *Staphylococcus aureus*, *Staphylococcus epidermidis*, *Enterococcus faecalis*, *Pseudomonas aeruginosa*, *Escherichia coli*, *Klebsiella pneumoniae* and *Enterobacter cloacae* (J. Infection, vol. 26, pp. 159–170 (1993), J. Clin. Microbiol., vol. 31., pp. 552–557 (1993)), respectively listed as relatively popular causative bacteria of the infectious diseases, especially bacteremia were described as follows.

EXAMPLE 1
Preparation of DNA Probe form Causative Bacteria of Infectous Diseases (1) Isolation of Causative Bacteria of Infectious Diseases Blood collected from the patient who have been suffered with targeted diseases were applied to Blood Culture Method (BBC System: Blood Culture System; Roche) and to a conventional identification kit (Api 20, Apistaf, Apistlep 20: Bio-Meryu), and the each causative bacterium was isolated and identified according to the manual of said kit.

(2) Extraction and Purification of Genomic DNA from Isolated Strain

Strains isolated in the above (1) was cultivated overnight in BHI (Brain Heart Infusion) medium, collected the cultivated bacteria, added thereto achromopeptidase in stead of lysozyme, then, Genomic DNA was extracted according to Saito-Miura Method ("Preparation of Transforming Deoxyribonucleic Acid by Phenol Treatment", Biochem. Biophys. Acta. vol. 72, pp. 619–629), and extracted DNA was digested with restriction enzyme HindIII and was random cloned into vector pBR322.

(3) Selection of Probe having Specificity to Species of Origin Bacteria

*Escherichia coli* containing each clone prepared according to Manual of Maniatis (T. Mlaniatis, et al., "Molecular Cloning (A Laboratory Manual)", Cold Spring Harbour Laboratory (1982)) was cultivated with small scale culture, and obtained plasmids containing each clone.

These plasmids were digested with restriction enzyme HindIII, thereby inserts were separated completely from plasmids with 1% agarose-gel electrophoresis (Myupid: Cosmo-Bio), then, were transcribed to nylon membrane with Southern-Transfer Technique (Paul Biodine A: Paul), and were cross-hybridized with a probe prepared by labelling $^{32}$P-dCTP (Amersham) through nick-translation to chromosome DNA from each bacteria species aforelisted.

In this hybridization, a probe which did not cross-react with any insert except for a probe prepared from the origin species thereof was selected as a probe containing DNA fragment which is specific to causative bacteria of the infectious diseases.

With regard to probes prepared from *Escherichia coli*, *Klebsiella pneumoniae*, *Enterobacter cloacae*, since these bacteria are belonged to the same group (enteric bacteria; Gram negative aerobic bacillus) as a causative bacteria of bacteremia (See, J. Infection, vol. 26, pp. 159–170 (1993), J. Clin. Microbiol., vol. 31., pp. 552–557 (1993), supra), and the cross-reaction had been confirmed among said three bacteria in the foregoing series experiments on the specificity, each probe prepared from one of said three bacteria was designated as a probe for detecting all these bacteria as a relevant bacteria.

Probes (denotation) selected from each species through the foregoing methods are listed in the following Table 1.

TABLE 1

| SPECIES | DENOTATION |
|---|---|
| *Staphylococcus aureus* | SA-7, SA-24, SA-36, SA-77 |
| *Staphylococcus epidermidis* | SE-3, SE-22, SE-32, SE-37 |
| *Enterococcus faecalis* | S2-1, S2-3, S2-7, S2-27 |
| *Pseudomonas aeruginosa* | P2-2, P2-7, P2-17, P4-5 |
| *Escherichia coli* | EC-24, EC-34, EC-39, EC-625 |
| *Klebsiella pneumoniae* | KI-50 |
| *Enterobacter cloacae* | ET-12, ET-49 |

Restriction enzyme maps of each probe were also illustrated in FIGS. 1–6 respectively.

EXAMPLE 2
Evaluation on Species-Specificity of Each DNA Probe

Reactivity between each probe and DNA from causative bacteria of infectious diseases were examined according to the following method.

First of all, as subject strains for an examination, clinical isolates of *Staphylococcus aureus*, *Staphylococcus epidermidis*, *Enterococcus faecalis*, *Pseudomonas aeruginosa*, *Escherichia coli*, *Klebsiella pneumoniae*, and *Enterobacter cloacae* were isolated according to the method of Example 1 (1) above.

Then, DNA of each clinical isolate were extracted according to the method of Example 1 (2), and samples for dot-blot-hybridization were obtained by spotting certain amount (e.g., 5 μl) of DNA to nylon filter and selecting the isolates denatured with alkaline. Hybridization on DNA probes prepared from each subjected bacterium and labelled with biotin (Bio-dUTP; BRL) were performed overnignt according to Manual of Mianiatis, supra, under the condition of 45% formamide, 5×SSC, 42° C.

Samples obtained through overnight hybridization were washed twice with 0.1×SSC, 0.1% SDS for 20 minutes at 55° C., then, were detected the color reaction with Streptavidin-ALP conjugates (BRL), and evaluated the hybridization.

Experimental results on reactivity between each probe and DNA of each clinical isolate are illustrated in the following table 2(i)-(vi). With regard to a denotation in the tables, denotation of "+" refers to the presence of a signal on hybridization, while that of "–" refers to the absence of a signal on hybridization.

TABLE 2 (i)

|  | SA-7 | SA-24 | SA-36 | SA-77 |
| --- | --- | --- | --- | --- |
| Staphylococcus aureus | + | + | + | + |
| Staphylococcus epidermidis | – | – | – | – |
| Enterococcus faecalis | – | – | – | – |
| Pseudomonas aeruginosa | – | – | – | – |
| Escherichia coli | – | – | – | – |
| Klebsiella pneumoniae | – | – | – | – |
| Enterobacter cloacae | – | – | – | – |

TABLE 2 (ii)

|  | SE-3 | SE-22 | SE-32 | SE-37 |
| --- | --- | --- | --- | --- |
| Staphylococcus aureus | – | – | – | – |
| Staphylococcus epidermidis | + | + | + | + |
| Enterococcus faecalis | – | – | – | – |
| Pseudomonas aeruginosa | – | – | – | – |
| Escherichia coli | – | – | – | – |
| Klebsiella pneumoniae | – | – | – | – |
| Enterobacter cloacae | – | – | – | – |

TABLE 2 (iii)

|  | S2-1 | S2-3 | S2-7 | S2-27 |
| --- | --- | --- | --- | --- |
| Staphylococcus aureus | – | – | – | – |
| Staphylococcus epidermidis | – | – | – | – |
| Enterococcus faecalis | + | + | + | + |
| Pseudomonas aeruginosa | – | – | – | – |
| Escherichia coli | – | – | – | – |
| Klebsiella pneumoniae | – | – | – | – |
| Enterobacter cloacae | – | – | – | – |

TABLE 2 (iv)

|  | P2-2 | P2-7 | P2-17 | P4-5 |
| --- | --- | --- | --- | --- |
| Staphylococcus aureus | – | – | – | – |
| Staphylococcus epidermidis | – | – | – | – |
| Enterococcus faecalis | – | – | – | – |
| Pseudomonas aeruginosa | + | + | + | + |
| Escherichia coli | – | – | – | – |
| Klebsiella pneumoniae | – | – | – | – |
| Enterobacter cloacae | – | – | – | – |

TABLE 2 (v)

|  | EC-24 | EC-34 | EC-39 | EC-625 |
| --- | --- | --- | --- | --- |
| Staphylococcus aureus | – | – | – | – |
| Staphylococcus epidermidis | – | – | – | – |
| Enterococcus faecalis | – | – | – | – |
| Pseudomonas aeruginosa | – | – | – | – |
| Escherichia coli | + | + | + | + |
| Klebsiella pneumoniae | + | + | + | + |
| Enterobacter cloacae | + | + | + | + |

TABLE 2 (vi)

|  | ET-12 | ET-49 | KI-50 |
| --- | --- | --- | --- |
| Staphylococcus aureus | – | – | – |
| Staphylococcus epidermidis | – | – | – |
| Enterococcus faecalis | – | – | – |
| Pseudomonas aeruginosa | – | – | – |
| Escherichia coli | + | + | + |
| Klebsiella pneumoniae | + | + | + |
| Enterobacter cloacae | + | + | + |

Apparently from Table 2 above, each probe have reacted only with DNA obtained from origin strain (or relative strain thereof) and not reacted (hybridized) with any DNA obtained from strains except for strains from the origin strain, therefore, their specificity have been confirmed.

EXAMPLE 3

Analysis of Base Sequence

Base sequence of DNA probes (total 23 probes) of the present invention, which have been confirmed their specificity to the origin species in the Examples 1 and 2, were sequenced according to the following method.

(1) Preparation of Plasmid DNA

Escherichia coli K-12, JM109 transformants, wherein the subcloned insert fragments (to be seqeuenced) is contained in pGem-3Z (Promega), was inoculated in 5 ml of Luria-Bactani Medium (bacto-tryptone, 10 g/1 L; bacto-yeast extract, 5 g/1 L; NaCl, 10 g/1 L; adjusted pH to 7.0 with 5N NaOH) and cultivated overnight.

Culture liquid was centrifuged (5,000 rpm, 5 min.) and collected the bacteria. 100 µl of solution of 50 mM glucose/ 50 mM Tris-HCl (pH 8.0)/10 mM EDTA containing 2.5 mg/ml of lysozyme (Sigma) was added to precipitate, and left at room temperature for five minutes. 0.2M NaOH solution containing 1% of sodium dodecyl sulfate (Sigma) was added to the suspension so obtained and mixed therewith. 150 µl of 5M pottasium acetate solution (pH 4.8) was further added thereto and mixed therewith, then iced for 15 minutes.

Supernatant obtained by centrifugation (15,000 rpm, 15 min.) was treated with phenol/CHCl$_3$ and added thereto ethanol of two times volume, then precipitate was obtained by centrifugation (12,000 rpm, 5 min.). This precipitate was dissolved in 100 µl of solution of 10 mM Tris-HCl (pH 7.5)/0.1 mM EDTA and added thereto 10 mg/ml RNaseA (Sigma) solution, then left it at room temperature for 15 minutes.

300 µl of 0.1M sodium acetate solution (pH 4.8) was added to this preparation and treated with phenol/CHCl$_3$, then precipitate was obtained by adding ethanol to supernatant. DNA samples were prepared by drying this precipitate and dissolving in 10 µl distilled water.

(2) Pretreatment for Sequencing

Pretreatment for sequencing was performed with Auto-Read™ Sequencing Kit (Pharmasia).

Concentration of DNA to become a template was, adjusted to 5–10 μg in 32 μl. 32 μl of template DNA was transferred to 1.5 ml mini-tube (Eppendolf), and added thereto 8 μl of 2M NaOH solution, then mixed gently therewith. After instant centrifugation, it was left at room temperature for 10 minutes.

7 μl of 3M sodium acetate (pH 4.8) and 4 μl of distilled water, then 120 μl of ethanol were added thereto then mixed therewith, and left for 15 minutes on dry ice. DNA which have been precipitated by centrifugation for 15 minutes were collected, and supernatant was removed carefully. The precipitate so obtained were washed with 70% ethanol and centrifuged for 10 minutes. Then, the supernatant wa removed carefully again and dried the precipitate under the reduced pressure.

The precipitate was dissolved in 10 μl of distilled water, then 2 μl of fluorescent primer (0.42 $A_{260}$ unit/10 ml, 4–6 pmol) [M13 Universal Primer; 5'-Fluorescein-d [CGACGTTGTAAAACGACGGCCAGT]-3 (SEQ ID NO:24 ) (1.6 pmol/μl; 0.42 $A_{260}$ unit/ml); M13 Reverse Primer, 5'-Fluorescein-d[CAGGAAACAG CTATGAC]-3' (SEQ ID NO:25)(2.1 pmol/μl; 0.42 $A_{260}$ unit/ml)] and 2 μl of saline for annealing were added thereto, and mixed gently.

After instant centrifugation, they were heat-treated at 65° C. for 5 minutes and rapidly transferred it to a circumstance of 37° C. and kept the temperature for 10 minutes. After keeping the temperature, it was left at room temperature for 10 minutes or more and centrifugated instantly. Then, samples were prepared by adding thereto 1 μl of an elongation saline and 3 μl of dimethyl sulfoxide.

Four mini-tubes have been identified with one of marks of "A", "C", "G" and "T", and, according to the mark, 2.5 μl of A Mix (dissolved ddATP with dATP, dCTP, $c^7$dGTP and dTTP), C Mix (dissolved ddCTP with dATP, dCTP, $c^7$dGTP and dTTP), G Mix (dissolved ddGTP with dATP, dCTP, $c^7$dGTP and dTTP), or T Mix (dissolved ddTTP with dATP, dCTP, $c^7$dGTP and dTTP) were poured into each identified tube. Each solution was preserved in freezed condition, and the solution was heated at 37° C. for one minute or more to use it.

2 μl of diluted T7DNA polymerase (Pharmacia; 6–8units/2 μl) was added to DNA sample, and completely mixed by pipetting or mixing it gently. Immediately after completing the mixing, these mixed solution was poured into 4.5 μl of four-types solution respectively which have kept the certain temperature. Fresh tips were used at the time of pouring.

The solution have been kept for five minutes at 37° C., then 5 μl of termination solution were poured into each reaction-solution. Fresh tips were used for pouring. Immediately after keeping the solution for 2–3 minutes at 90° C., it was cooled on ice. 4–6 μl/lane of the solution was applied to the electrophoresis.

(3) Sequencing on Base Sequence

Sequencing on each base sequence of probes, disclosed in Examples 1 and 2, having the specificity against *Staphylococcus aureus* or *Staphylococcus epidermidis* were performed with A.L.F. DNA Sequencer System (Pharmacia) under an electrophoresis condition of 45° C. for 6 hours.

Then, base sequences of the probes (SEQ ID. No.) prepared from each causative bacteria of the infectious diseases and listed in the following table 3 were disclosed in the sequence listing attached hereto.

TABLE 3

| SPECIES | Probes (SEQ ID. No.) |
|---|---|
| *Staphylococcus aureus* | SA-7 (1), SA-24 (2) |
| | SA-36 (3), SA-77 (4) |
| *Staphylococcus epidermidis* | SE-3 (5), SE-22 (6) |
| | SE-32 (7), SE-37 (8) |
| *Enterococcus faecalis* | S2-1 (9), S2-3 (10) |
| | S2-7 (11), S2-27 (12) |
| *Pseudomonas aeruginosa* | P2-2 (13), S2-7 (14) |
| | P2-17 (15), P4-5 (16) |
| *Escherichia coli* | EC-24 (17), EC-34 (18), |
| | EC-39 (19), EC-625 (20) |
| *Klebsiella pneumoniae* | KI-50 (23) |
| *Enterobacter cloacae* | ET-12 (21), ET-49 (22) |

Thereby, genetic information concerning the specific site of each causative bacteria of the infectious diseases (or relative bacteria thereof) have been clarified.

According to probes of the present invention, for example, causative bacteria of the infectious diseases which have incorporated into the phagocyte can be directly detected, and rapidly and exactly identified without proliferating the bacteria. That is to say, according to the diagnosis using the probe of the present invention, identification of the bacteria can be realized with single specimen, then, reduced the necessary time for diagnosis to about one to two day(s), while the conventional method (with low detection rate) required 3–4 days, and improved remarkably the detection rate. Therefore, this invention can provide an objective factors for the treatment of bacteremia, then realize the effective treatment in the early stage of the infectious diseases, and expect to reduce the mortality.

Then, by clarifying the base sequences of probes which specifically react with primary bacteria of the infectious diseases, these probes can be prepared artifically. Further, a part of information on the analyzed base sequences may be used for rapidly diagnosing the causative bacteria by amplifying DNA of causative bacteria of the infectious diseases in the clinical specimen with PCR technique and primers prepared by making use of said information.

Further, by comparing base sequences of Genomic DNA in the clinical specimen with that of the present invention, rapid identification of the species of the causative bacteria of infectious diseases can be realized.

As stated above, the present invention provide desirable probes for diagnosing the infectious diseases, then expect utilities as a factor to prepare primers for PCR and standard sequence for a comparison with Genomic DNA in the clinical specimen, and further expect an effect to provide valuable hints for preparing and developing the other probes which specifically react with causative bacteria of the infectious diseases.

Then, since the base sequences disclosed in the present application was obtained by random-cloning the Genomic DNA of clinical isolates, utilities of the base sequences of the present invention should be extended to the complementary strands thereof.

Further, although it may be thought that DNA obtained from the wild strains contain the mutated portion, apparently from the disclosure of the Examples above, said mutated DNA portion would not affects the utilities to be derived by the present invention comprising the specificity of the probes of the present invention in the hybridization for a diagnosis of the infectious diseases, and an usage of the information on the base sequences disclosed in the present application to design the primers for PCR technique to realize a rapid diagnosis of the infectious diseases.

We claim:

1. A probe composition for detecting *Pseudomonas aeruginosa* wherein the probe composition consists essentially of (a) the DNA of any one of SEQ ID NOS:13 through 16, or (b) the complement of (a).

2. A method for detecting the presence of *Pseudomonas aerugiinosa* in a sample comprising the steps of contacting nucleic acid from said sample with the probe composition of claim 1 and detecting hybridization of the nucleic acid from said sample with DNA in said probe composition as an indication of the presence of *Pseudomonas aeruginosa*.

* * * * *

UNITED STATES PATENT AND TRADEMARK OFFICE
CERTIFICATE OF CORRECTION

PATENT NO.    : 5,798,211              Page 1 of 2
DATED         : August 25, 1998
INVENTOR(S)   : Ohno et al.

Figure 5:
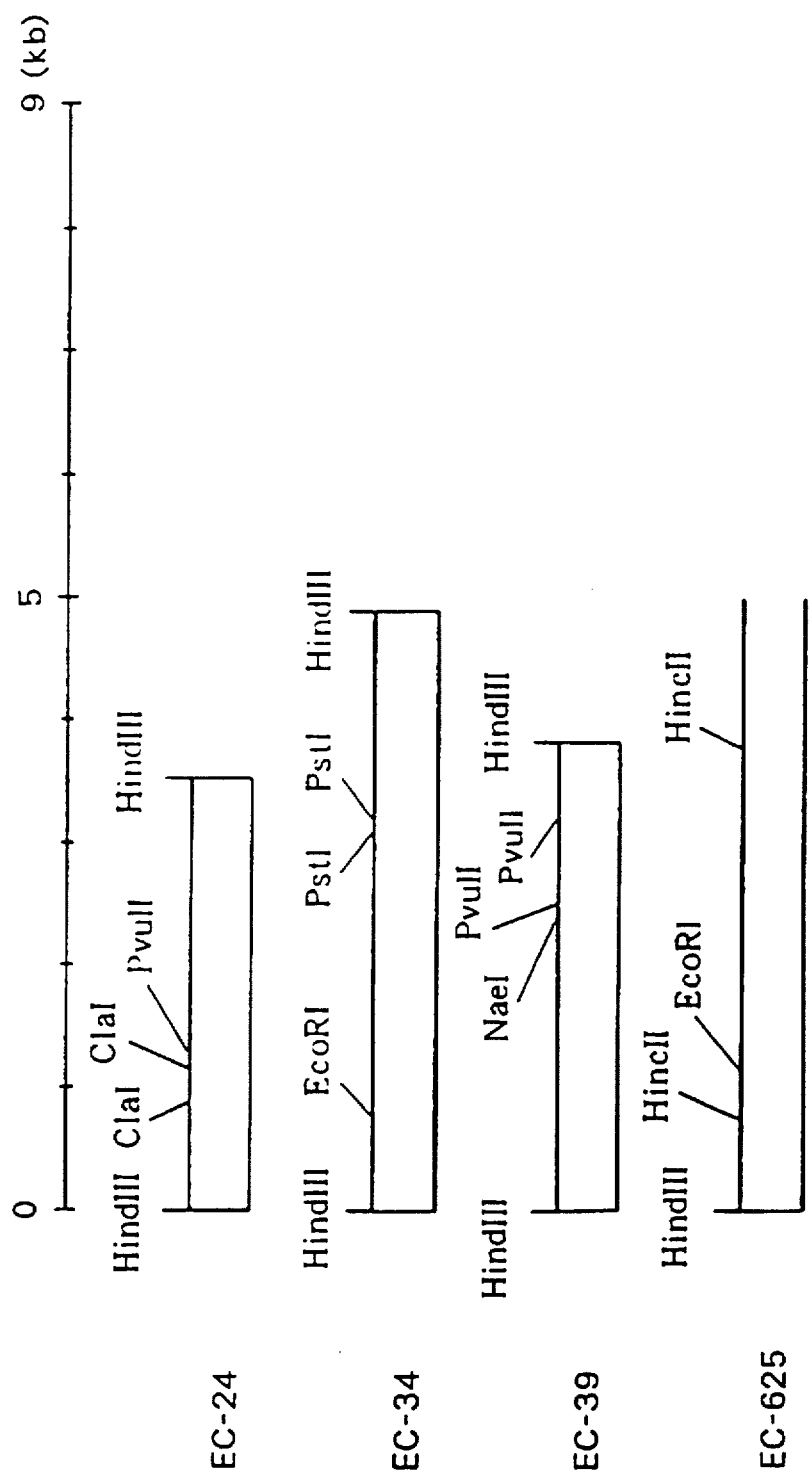
FIG. 5 is a restriction enzyme map of HindIII fragment on probe for detecting *Escherichia coli*.
Figure 6:
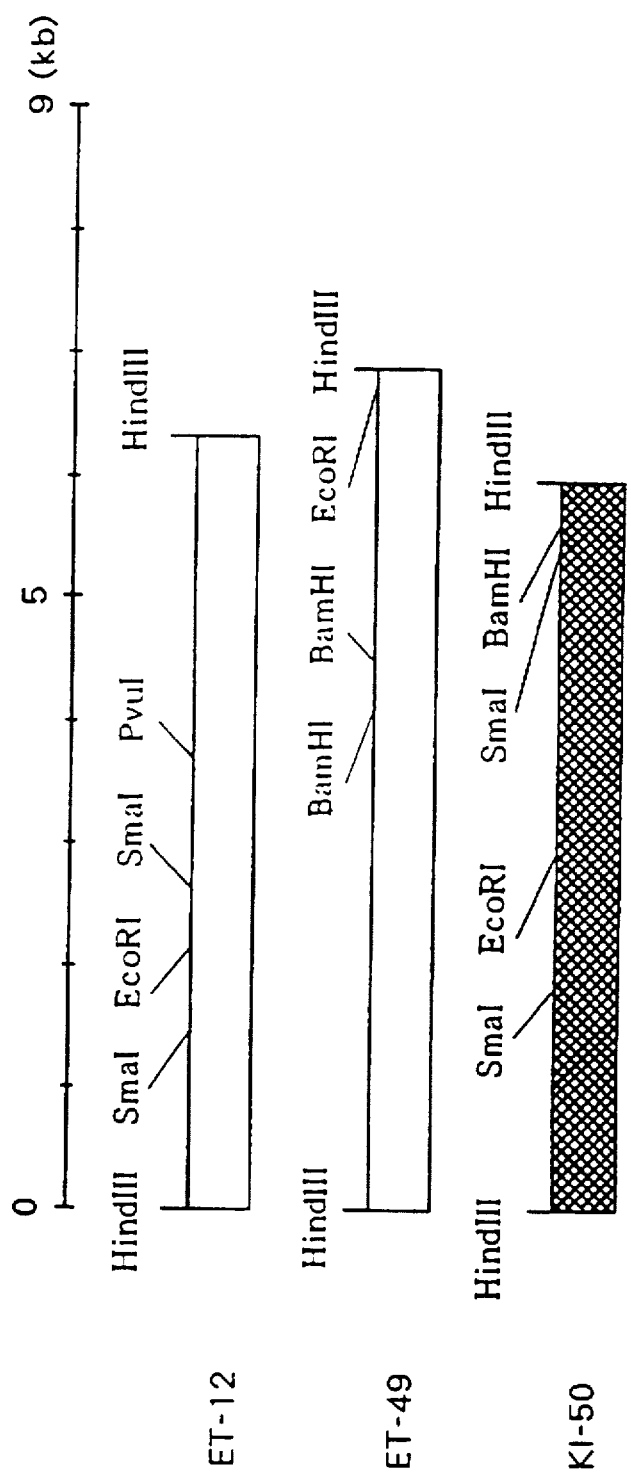
FIG. 6 is a restriction enzyme map of HindIII fragment on probe for detecting *Enterobacter cloacae* and *Klebsiella pneumonia*.

It is certified that error appears in the above-identified patent and that said Letters Patent is hereby corrected as shown below:

Drawings,
FIG. 5, please delete "

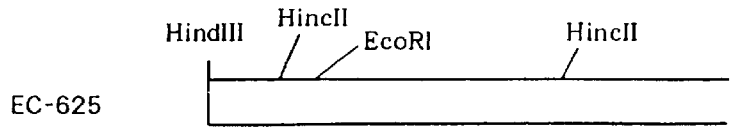

and insert --

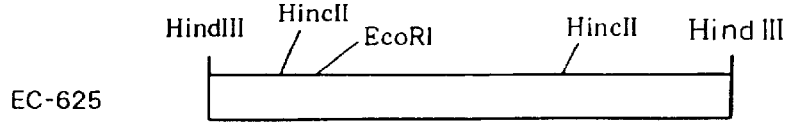

therefor. --

Column 1,
Line 21, please delete "bateremia" and insert -- bacteremia -- therefor.

Column 2,
Line 36, please delete "*epidermides*" and insert -- *epidermidis* -- therefor.
Line 62, please delete "thier" and insert -- their -- therefor.

Column 3,
Line 52, please delete "form" and insert -- from -- therefor.
Line 53, please delete "Infectous" and insert -- Infectious -- therefor.

Column 4,
Line 8, please delete "Mlaniatis" and insert -- Maniatas -- therefor.

Column 5,
Line 3, please delete "Mianiatis" and insert -- Maniatas -- therefor.

UNITED STATES PATENT AND TRADEMARK OFFICE
CERTIFICATE OF CORRECTION

PATENT NO. : 5,798,211
DATED : August 25, 1998
INVENTOR(S) : Ohno et al.

It is certified that error appears in the above-identified patent and that said Letters Patent is hereby corrected as shown below:

Column 6,
Line 37, please delete "seqeuenced" and insert -- sequenced -- therefor.
Line 49, please delete "pottasium" and insert -- potassium -- therefor.
Line 67, please delete "(Pharmasia)" and insert -- (Pharmacia) -- therefor.

Column 7,
Line 1, after "was" please delete "," therefor.
Line 13, please delete "wa" and insert -- was -- therefor.
Line 19, please delete "3" and insert -- 3' -- therefor.

Column 8,
Line 10, please delete "Pseudomonas aeruginosa P2-2(13), S2-7(14)" and insert -- Pseudomonoas aeruginosa P2-2(13), P2-7(14) -- therefor.

Column 114,
Line 42, please delete "aerugiinosa" and insert -- aeruginosa -- therefor.

Signed and Sealed this

Twenty-seventh Day of August, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
    ( A ) LENGTH: 8959 base pairs
    ( B ) TYPE: nucleic acid
    ( C ) STRANDEDNESS: double
    ( D ) TOPOLOGY: linear ( i i ) MOLECULE TYPE: Genomic DNA ( v i ) ORIGINAL SOURCE:
    ( A ) ORGANISM: Staphylococcus aureus
    ( B ) STRAIN: Clinical Isolate SA- 7

( x i ) SEQUENCE DESCRIPTION: SEQ ID NO:1:

| | | | | | | |
|---|---|---|---|---|---|---|
| AAGCTTTATC | TGCTGAATAT | ACCGCATTTT | TTATCTTGTT | AATTGTCGGC | ACATTTTCTT | 60 |
| CAATAGTTAA | ACCTGCTTTG | TTAGCTTCTT | CTAATAATGC | TCGAGTTACT | GTTTATTAAA | 120 |
| TGTTCATTCG | CTTTTCAACG | ACAACTGACG | AACCAGTATC | TGTTAGCTTA | GACGCAACAG | 180 |
| CGTTAATCTT | CTGATTCACC | TTAAATTCTA | CATCTGCTTT | TTGAGGCTGC | TTACGTAGTG | 240 |
| TCCCGGTAAT | TTCATGTGTA | AACTTAGATG | GGATGTAAAT | ACCTGCAAAA | TATTTACCCA | 300 |
| TTTTTATCTC | ATGATCAGCT | TTCTCTCTAC | TTACAAACTG | CCAATCAAAA | CTTTTATTTT | 360 |
| TCTTGAGTGT | ATTAACCATC | GTATTACCGA | CATTAACTTT | TTTCCCTCTG | ATTGTGTCGC | 420 |
| CTTTATCTTC | ATTAACGACT | GCGACCTTGA | TGTGTCCCGT | GTTGCCATAT | GGATCCCACA | 480 |
| TTGCCCATAA | GTTAAACCAA | GCGTAGAACG | ATGGCAAAAT | AGCTAAGCCT | GCTAAGATAA | 540 |
| TCCACACAGC | TGGCGTCTTA | GCTACTTTCT | TCAGATCCAT | TTTAAATAAT | TTAAATGCGT | 600 |
| TCTTCATTGT | CACACTCCTA | TGTAGGAATT | ATTCATATTT | TTTATATATT | TTTTGTAAAT | 660 |
| TAATTTATTT | TTGCGTTGTG | AATTAGTATA | ATCAATTTAC | TGGAAGATAT | TTAGTCGATT | 720 |
| GATACCTATC | AACTATTTTC | AGCATACGAT | AAATTATAAC | AAATCATAGT | TTATTATCAC | 780 |
| ACTTAATTAT | TATATTTTTC | AAGGGAGAAT | ACGAAATATG | CCTAAAAATA | AAATTTTAAT | 840 |
| TTATTTGCTA | TCAACTACCC | TCGTATTACC | TACTTTAGTT | TCACCTACCG | CTTATGCTGA | 900 |
| TACACCTCAA | AAAGATACTA | CAGCTAAGAC | AACATCTCAT | GATTCAAAAA | AATCTAATGA | 960 |
| CGATGAAACT | TCTAAGGATA | CTACAAGTAA | AGATACTGAT | AAAGCAGACA | ACAATAATAC | 1020 |
| AAGTAACCAA | GACAATAACG | ACAAAAAATT | TAAAACTATA | GACGACAGCA | CTTCAGACTC | 1080 |
| TAACAATATC | ATTGATTTTA | TTTATAAAGA | ATTACCACA | AACCAATATA | AACCAATTGC | 1140 |
| TAACCAAAAA | TAAATACGAT | GATAATTACT | CATTAACAAC | TTTAATCCAA | AACTTATTCA | 1200 |
| ATTTAAATTC | GGATATTTCT | GATTACGAAC | AACCTCGTAA | TGGCGAAAAG | TCAACAAATG | 1260 |
| ATTCGATAAA | AACAGTGACA | TAGCATCAAA | AATGACACTG | ATACGCAATC | ATCTAAACAA | 1320 |
| GATAAAGCAG | ACAATCAAAA | AGCACCTAAA | TCAAACAATA | CAAAACCAAG | TACATCTAAT | 1380 |
| AAGCAACCAA | ATTCGCCAAA | GCCAACACAA | CCTAATCAAT | CAAATAGTCA | ACCAGCAAGT | 1440 |
| GACGATAAAG | CAAATCAAAA | ATCTTCATCG | AAAGATAATC | AATCAATGTC | AGATTCGGCT | 1500 |
| TTAGACTCTA | TTTTGGATCA | ATACAGTGAA | GATGCAAAGA | AAACACAAAA | AGATTATGCA | 1560 |
| TCTCAATCTA | AAAAAGACAA | AAATGAAAAA | TCTAATACAA | AGAATCCACA | GTTACCAACA | 1620 |
| CAAGATGAAT | TGAAACATAA | ATCTAAACCT | GCTCAATCAT | TCAATAACGA | TGTTAATCAA | 1680 |

-continued

| | | | | | |
|---|---|---|---|---|---|
| AAGGATACAC | GTGCAACATC | ATTATTCGAA | ACAGATCCTA | GTATATCTAA | CAATGATGAT | 1740 |
| AGCGGACAAT | TTAACGTTGT | TGACTCAAAA | GATACACGTC | AATTTGTCAA | ATCAATTGCT | 1800 |
| AAAGATGCAC | ATCGCATTGG | TCAAGATAAC | GATATTTATG | CGTCTGTCAT | GATTGCCCAA | 1860 |
| GCAATCTTAG | AATCTGACTC | AGGTCGTAGT | GCTTTAGCTA | AGTCACCAAA | CCATAATTTA | 1920 |
| TTCGGTATCA | AAGGTGCTTT | TGAAGGGAAT | TCTGTTCCTT | TTAACACATT | AGAAGCTGAT | 1980 |
| GGTAATAAAT | TGTATAGTAT | TAATGCTGGA | TTCCGAAAAT | ATCCAAGCAC | GAAAGAATCA | 2040 |
| CTAAAAGATT | ACTCTGACCT | TATTAAAAAT | GGTATTGATG | GCAATCGAAC | AATTTATAAA | 2100 |
| CCAACATGGA | AATCGGAAGC | CGATTCTTAT | AAAGATGCAA | CATCACACTT | ATCTAAAACA | 2160 |
| TATGCTACAG | ATCCAAACTA | TGCTAAGAAA | TTAAACAGTA | TTATTAAACA | CTATCAATTA | 2220 |
| ACTCAGTTTG | ACGATGAACG | CATGCCAGAT | TTAGATAAAT | ATGAACGTTC | TATCAAGGAT | 2280 |
| TATGATGATT | CATCAGATGA | ATTCTGTTCC | TTTTAACACA | TTAGAAGCTG | ATGGTAATAA | 2340 |
| ATTGTATAGT | ATTAATGCTG | GATTCCGAAA | ATATCCAAGC | ACGAAAGAAT | CACTAAAAGA | 2400 |
| TTACTCTGAC | CTTATTAAAA | ATGGTATTGA | TGGCAATCGA | ACAATTTATA | AACCAACATG | 2460 |
| GAAATCGGAA | GCCGATTCTT | ATAAAGATGC | AACATCACAC | TTATCTAAAA | CATATGCTAC | 2520 |
| AGATCCAAAC | TATGCTAAGA | AATTAAACAG | TATTATTAAA | CACTATCAAT | TAACTCAGTT | 2580 |
| TGACGATGAA | CGCATGCCAG | ATTTAGATAA | ATATGAACGT | TCTATCAAGG | ATTATGATGA | 2640 |
| TTCATCAGAT | GAATTCAAAC | CTTTCCGCGA | GGTATCTGAT | AGTATGCCAT | ATCCACATGG | 2700 |
| CCAATGTACT | TGGTACGTAT | ATAACCGTAT | GAAACAATTT | GGTACATCTA | TCTCAGGTGA | 2760 |
| TTAGGTGAT | GCACATAATT | GGAATAATCG | AGCTCAATAC | CGTGATTATC | AAGTAAGTCA | 2820 |
| TACACCAAAA | CGTCATGCTG | CTGTTGTATT | TGAGGCTGGA | CAATTTGGTG | CAGATCAACA | 2880 |
| TTACGGTCAT | GTAGCATTTG | TTGAAAAAGT | TAACAGTGAT | GGTTCTATCG | TTATTTCAGA | 2940 |
| TCAATGTTAA | AGGATTAGGT | ATCATTTCTC | ATAGAACTAT | CAATGCAGCT | GCCGCTGAAG | 3000 |
| AATTATCATA | TATTACAGGT | AAATAAGTAT | TATTAAACCC | GCAAAATTTA | TAAGTATAAA | 3060 |
| CAAGGAGTTC | GGACTTAAAC | ATATTTCTGT | TCATAAGTCC | GATTTCTTAT | TCAATTAAAC | 3120 |
| CCGAGGTATT | CAGTTCGAAC | GCCTCGGGTC | ATTTTATATA | AATATATTAT | TTTATGTTCA | 3180 |
| AATGTTCCTC | ATCATATCCG | TTTCAATTGT | CATCTCACAC | ATTTTATAAA | TATGAGCAAA | 3240 |
| TGTACTTATT | TTCAAACATT | ACTGCCTAGC | TTTAATTGAC | GTTATATTAA | CTATAAACTA | 3300 |
| CTTTTCCATG | ACTCTACGGA | TTCAATGTCA | CATGAGCGTG | ATAAATTTG | TTCAATAATA | 3360 |
| AAGTCATGTT | TATCATCTGA | TCTATCACCA | ACAGCATCTT | CTAAACAGT | AATATAATAG | 3420 |
| TCTTTATCTA | CACTTTCTAA | TGCCGTGCTC | AATACAGCTC | CACTCGTAGA | GACACCCGTT | 3480 |
| AATACTAAAT | GATTAATATC | ATTTGCACGT | AAATAAACTT | CCAAGTAACT | ACCTGTAAAT | 3540 |
| GCGCTAAAGC | GTCGCTTAGA | AATAATCGGC | TCATCTTCTA | GTGGTGCTAA | ATCTTCAAGT | 3600 |
| ATTCGTGTAG | ATGCATCTGC | TTCAGTAATC | GCATATCCTT | GAGCTTTAAT | TGTTGAAAAC | 3660 |
| ACTTTATTAC | TCGAGGAGAC | ATCATTAAAA | TGCTTATCTA | ACACTAAACG | TATGAAAATG | 3720 |
| ACTGGTATTC | GATGTTGTCT | TGCTGCTTCA | ATTGCTCTCT | GATTCGCTTT | AATAATATTT | 3780 |
| TTTATTCTAG | GTACACTACT | CGCTATACTT | CTTGCATATC | CAAACTAATA | GCGCCGTTTT | 3840 |
| TCGAGACATC | TTCATTCTCC | TTTACTTCTG | TAGTTCTAAG | TCGTTAAATT | CATTATAACG | 3900 |
| TTAAAATGAT | GGACAATCTA | TTCATTGCAT | TTGCATATA | CTTCACAATA | ATTTAAGGGG | 3960 |
| GAAATAAGAC | GTCTTATATA | CTTAAAAAAA | TATATAGATG | CTCTTCCCCC | AATATAATTA | 4020 |
| TGCTTTATTT | TTCAACTTAT | TGCGTCGTGA | TAACCAAATC | ATTAGTACAC | CCATTGCACC | 4080 |

| | | | | | |
|---|---|---|---|---|---|
| AACAATTACA | GATATCGGCA | ACCAATGTTC | TTTTATCGTT | TCCCCGCTTT | AGGCAAGATA | 4140 |
| CATTACCATC | AGCATTTAAT | AATCCACTTA | ACAATCCATT | ACCTTTACCA | AGTGTTACGT | 4200 |
| CTTTTCTGGC | TTTGGTGTGG | GTATATCTGG | AATACTGTCT | AATAAATTTG | ATCCTTGATT | 4260 |
| CATTAAATTT | GCTAACTTAT | TTAAATCCGT | TGTTTCCCA | TTTTATTCA | ATCGATCTAG | 4320 |
| TAAACTTGGA | CGATTTACTA | TTGGTGATAA | AATATAGTCT | ATATCTTTT | TCGTTTGATT | 4380 |
| GAGTCTCTTT | TGTAAATTCA | ATAAATCATC | CGCTTTACCA | TTCAATGCCG | ATTTAACTAA | 4440 |
| ATTAAAAATT | TTATTTTGAT | CTGTTTCTAT | TTAGTAATT | AAATCTGCCA | GTAATTTTGC | 4500 |
| CTTTTGTCTT | TCTATACGTG | TTGCTAAAAT | CGTTTCAATT | GCTTGCTTTT | TATCTTTGGC | 4560 |
| ATTATTCAAA | ATTGCTTTTA | ATATATCATC | TGAAGACGTG | TCGCCAGTTG | ATGCAAAATG | 4620 |
| TTTCTTCAAT | TGGTCAACGA | TTTGGCGATT | TGATAATCCT | TTATTCGTCC | AATCTTTAGC | 4680 |
| CAATTTATCT | GCTTCAGCTT | TTCCTAATTT | CGTTTGTAAG | ATTTGAGAAA | TCAATAGCGA | 4740 |
| CTTATCTTGT | GATTGATCAA | TCAATGACGT | TAATAAATCA | TCACTCGTTG | TCAGAGATAG | 4800 |
| TTGATCAATA | TGACGAGTAA | TTTGATCTGC | AATTTGTTGA | TCTGTTTTAC | CATCAACACG | 4860 |
| TATATCTTTT | AGAATTTTAT | CTGCCTCGTC | TTTATTAAAT | ATACTTTCTA | AAATGCTTTG | 4920 |
| TGTAGCATAC | TTTTTATCAT | CAGTACGTGC | AAGTTCTTCC | AAAATAATAT | TTCGTTGACT | 4980 |
| TTTTATACGC | TCTTTCGTCT | TATTTACTTC | GCTCATTAAG | TCTGATTTTT | GATTTTAGG | 5040 |
| AAGTTGCGTA | TTTGCAATAC | GTTGATCTAA | AGATTGTAAC | GTATTCAGTT | TATGATATGT | 5100 |
| GTAATGTTGC | GTTGAGGCAT | TACTTTTAGC | CAATTTTTCA | ATCATAGCAT | GATTAATTTT | 5160 |
| ATCGCTTCCT | TGTAATTTAT | CAGTGAGTTG | ATTACTATGG | CTTTGATTCT | CTTCATTTGA | 5220 |
| AAGAAATTTA | TTTAACACAA | CATGTCCAGA | ACCATCATTA | TTTGGCGTTT | TAGCTACTTC | 5280 |
| ATGATTACTA | TCTGTTGTAG | ACACTGCCGG | ATCTTTCGAT | GCATCTTTCA | ATGCATCTTT | 5340 |
| CGATTGTGT | ATTTGCTGAT | TCAAATGGTC | TAGGTCTTCT | AACGCCTTAT | TTACCATTGC | 5400 |
| TTCATCATTT | TTATCATCTT | TTTCTCCATA | TTTTGTTGTA | GCCGTTTGTG | ACATATCATT | 5460 |
| TTTCATTGCA | TTAAGATCGT | CCTCGCCACT | TTGTTGACCC | CTATCAACAT | TGAAGAAAC | 5520 |
| CTCATTTAAA | TCTTTAAGCA | ATTGATCTAA | TTTACTGTCT | ATATCACTTT | GACCGTTCAT | 5580 |
| TTCAGTGTGA | GAACTTTTAT | TTTCTTTGCT | ATCCAACTCA | TTAGCTCGTT | TTATGATTTC | 5640 |
| ATCTATTTGC | GATGCTGTTT | TCGCTTCATT | TAGTTGTGCT | TTATAATGTG | CTTTAGATGA | 5700 |
| AGCCGATAAC | TGTTTTAATT | GCTCAATTTG | ACGAATTGCT | TTGTCAACTT | TGTCTAATAA | 5760 |
| ATCTTGCTTA | GATAATATCT | CTTTTGAAAT | TTCAGTATCC | TTTTCAGATG | CAGCTTGGGC | 5820 |
| ATCGTACGGC | AAGATATTCG | TTAAAATGAT | ACTTGACGCC | ATCATTGTCG | AACACGATAA | 5880 |
| CTTTACATAT | AATTGAAACG | GTTTCCCTCG | ATATTTAGCC | ATCAACATAC | TCCTTTCTCA | 5940 |
| CTTACTTCCT | TCAAAGAATT | ACATACTATT | ATATACCTGT | TTACAAGAAA | TTTACACTTA | 6000 |
| TCTATCTAGT | TATTGTTGTT | AGTAATTATC | AACTTATTAC | TTAGCTTATA | TTAAGTAAA | 6060 |
| CAAAAAAGCA | TGACGTAATA | TCATATTGTC | CATGTCGCTA | ACATCATATT | ACGTCAAATC | 6120 |
| TTTTAAATTA | AATGATGCTT | TATTTAGAC | TGCTTTTTCT | TTTAGCTTT | CGAGCGCCTG | 6180 |
| TTTAAAAACT | TGCTCGAATT | GTTCACGCGA | GATTTCGTGT | GCATGTGCTT | TTTGTGCTAA | 6240 |
| TAAAGCATCT | CGAAACTGTT | GTTGATCTTT | CAAACTTTCT | AACATTTGTA | TTAATTGGTC | 6300 |
| TTTACTTTCC | ATTGTTATCT | CATCATTATG | CTCAAATAAG | TGCTCTGATA | ATGTTACTTT | 6360 |
| AGCATGGTGT | GCGGTTTGAC | GATAACCTAA | AATCAACAAC | TCATAGTCAA | ACGCTTGTTC | 6420 |
| CACCGCATTT | AAAATTTCAT | TACCCTCATT | GATATCAAGA | TAAATATCAC | ATAACTGGTA | 6480 |

| | | | | | |
|---|---|---|---|---|---|
| TAGTTCATTT | ACCCTGTCAA | TATAATAGAT | GGTATAAGTG | CACATTAGCA | TATTGATCAA | 6540 |
| GTTGCATTAG | CTTATCAGAC | ATCTCTGTAA | TAGCAGCGAT | GTGAAAATTA | AAATCTGGTA | 6600 |
| AAGTTTCAAC | CAATACCTTG | ATGTTACGAA | GTTGATCCGA | GTTAGTTAAT | ATTACAATTT | 6660 |
| CTTAGTATA | TCTATTACGA | CTACGATAGT | TATATAGATA | TCCGCCTTGT | AAAATACGAG | 6720 |
| ATTGAACCTT | TGCGTCTGCT | ATATTGAGCA | TCGTTTCATA | TTCGTTTTA | TCTGGAATAA | 6780 |
| TAATATTACA | ATGTCGTTTC | ATATCACCTT | TACACATCAA | TTGCATATTT | CCCGGGACAT | 6840 |
| TACCATTACA | GTGTTCTTGC | CATACCAAAA | CATCACTACC | TTTTGATGGC | AAATTATATA | 6900 |
| ACACTGAAAA | TGGTAGGGCT | AGTGAGTTAA | TAACGAAATG | ATGTTCCGTA | ATTTCAAGTT | 6960 |
| GCTTGATAAA | AAATAATACG | AATGCGAGCT | TTGAAGGGAA | AAAGTAAGAC | TTCCCTTGCC | 7020 |
| AATCCAATAT | GACATCAGAT | GTTACAAAAT | TTTCATAAAT | CACTTCTTTA | CCTTCTGCTG | 7080 |
| TCATATATTT | CTTCAAGATC | GCTTTACGAT | TTAAATCGTA | ACAGTTTGTG | CAATTTAATA | 7140 |
| CCATTCTTAG | AATAATAATC | GACAAATCGG | ACACGTTGTT | GGTCATCAAA | CCATTCGACA | 7200 |
| CGACTAACAA | TTCTAGGGCG | CTCTCCACTT | TGATAAAATA | TTTTGCCTCG | TAGACGTCCC | 7260 |
| ATATCATTAA | TTGTAGCCGA | ATTGTTGTTA | CCTTTAATTT | CCCAAAAAGC | TGGTACAGTA | 7320 |
| ACCTGATTAA | AAAATCGTGG | TTTCATATTT | TCTGTATTAT | GATTATCTGC | AAAAAATTGA | 7380 |
| TACGGTGATA | TAACATCGTC | CGGTAAAAAG | CCATTGTCAT | TGAGTACAAT | TGTTAAATCT | 7440 |
| TCTTCCAACT | TACTGGCTTT | AAAAGACTCA | TATAACTTTC | GTGAATGATC | GTTAAAGTAA | 7500 |
| TCAAATAATT | TAATCATGTA | GCACCTCTTG | AACTAATGTT | TCCCATTTTA | AAATAATATC | 7560 |
| TTGAGTCATA | AATTGCTGTG | CCACTTCATA | AGAGATGTCA | TGTGGTGCCT | GGGGACCATT | 7620 |
| GTTAAAATAC | ATTACAATGG | CATGAGCTAG | TTTTGCGATA | ACATCATCCA | CACTATCTTC | 7680 |
| GTCGGTATCA | AAAGGTACCA | AGTAGCCATT | TTCCCCATCT | CGAATAAAGG | TTGGGTTACC | 7740 |
| ATAATTCACA | TTTAATCCAA | TCATACCTAG | TCCTGAGCCT | ACCGCTTCCA | TTAGTGTTAA | 7800 |
| CCCAAAACCT | TCGCTAGTTG | ATGCAGAAAG | AAATAACTCA | TAATCATTAT | AAATTTCATC | 7860 |
| AAGTTTAACA | TGCCCTTAGT | AAACCGAATA | TAATCTTGTG | CGCGGTGTGT | ATCAATAATT | 7920 |
| TTACGCAGTC | GCGTCTTCTC | GCTACCTTCT | CCATAAATAT | CAAATGTTAA | TTCTGGCACT | 7980 |
| TGTCGTTTAG | CCACGATAAC | CGCCTTGACA | AGCCAATCAA | TATGTTTCTC | ATTTGCTAAA | 8040 |
| CGAGATGCAC | TAATCATCGC | ATATGGCTTT | CTTGATAATT | TAGGATATGA | TAACGCATCA | 8100 |
| ATGCTTCCCA | CCGGDATAGT | ATAGACACGT | GGACGATAAC | CTTGATATTG | CTCAAATTGT | 8160 |
| CGACAAACCA | TATGATTTTG | AATATCTGTT | GCTGTAATAA | AGAAATCAAT | GTATTTAGCT | 8220 |
| TTTGAAAATT | GATATTCATA | ATAATTGTTC | CATAGTATAT | GCTGCTCGCT | CATCATATTA | 8280 |
| TTACTATAAT | GATCAGCATG | AATCACAACA | CCAACTTTAC | TATCACCTTT | ATGCTGCAAA | 8340 |
| ACAGCCTGAC | CAATATCAGA | AGCGCGGTCT | AATATGACAA | TATCGTCTCG | GGTTAAATTC | 8400 |
| AATCGTTGTA | AAAGTATGC | AATAAATTCC | GTTTGTTAT | ACAACACCGC | ATCTTCAAAC | 8460 |
| ACATATATAG | AGCTGTCTCC | ATCAATATAT | TCGTTATAAG | CGATGGAACC | ATCTTCATTA | 8520 |
| TAGAATTGTC | GCATATATAA | TTTCGCTTTA | TTATCAGCTG | GTGCATAATA | CTCAGAAAAT | 8580 |
| ATACGCGTAT | AACTATAAAA | ATCTTTACGT | ACTAACATAC | TATTAATTAC | AATTCTGCAC | 8640 |
| GATCCACAAC | ATCTTTTTGT | TCATTTGTA | GATAACATGT | TACAAATGAT | GATTTCCCAT | 8700 |
| TAAAATATAG | ACGGACTATC | TTACCATTTC | TTTCTCTAAA | ACTAATTTCA | TGACCAAGCT | 8760 |
| CACGTTCAAT | GTCATCTAAC | GTGTACGTTG | TTGGTGCTAT | AGAAATATCA | CTAAAAATAC | 8820 |
| TGATACAACC | AAATAACTTC | TTGATCTTTA | AACCCAATGT | TTTGCGTTAA | TGTCTGTATG | 8880 |

| | | | | | |
|---|---|---|---|---|---|
| TTCTCTGACT | GTATAAAATC | TAAAAACACA | AATTTAGTGT | CTTGATTTGT | ACGTCTCAAT | 8940
| AATTTAGCAC | GGTAAGCTT | | | | | 8959

( 2 ) INFORMATION FOR SEQ ID NO:2:

( i ) SEQUENCE CHARACTERISTICS:
        ( A ) LENGTH: 10207 base pairs
        ( B ) TYPE: nucleic acid
        ( C ) STRANDEDNESS: double
        ( D ) TOPOLOGY: linear ( i i ) MOLECULE TYPE:Genomic DNA ( v i ) ORIGINAL SOURCE:
        ( A ) ORGANISM: Staphylococcus aureus
        ( B ) STRAIN: Clinical Isolate SA- 24

( x i ) SEQUENCE DESCRIPTION: SEQ ID NO:2:

| | | | | | |
|---|---|---|---|---|---|
| AAGCTTATGG | ACCTATTTTA | GGTATATTGA | TTAGTTGGCT | TGGATTAATT | TCTGGAACAT | 60
| TTACAGTCTA | TTTGATCTGT | AAACGATTGG | TGAACACTGA | GAGGATGCAG | CGAATTAAAC | 120
| AACGTACTGC | TGTTCAACGC | TTGATTAGTT | TTATTGATCG | CCAAGGATTA | ATCCCATTGT | 180
| TTATTTTACT | TTGTTTTCCT | TTTACGCCAA | ATACATTAAT | AAATTTGTA | GCGAGTCTAT | 240
| CTCATATTAG | ACCTAAATAT | TATTTCATTG | TTTGGCATC | ATCAAAGTTA | GTTCAACAA | 300
| TTATTTTAGG | TTATTTAGGT | AAGGAAATTA | CTACAATTTT | AACGCATCCT | TTAAGAGGGA | 360
| TATTAATGTT | AGTTGTGTTG | GTTGTATTTT | GGATTGTTGG | AAAAAAGTTA | GAACAGCATT | 420
| TTATGGGATC | GAAAAAGGAG | TGACATCGTG | AAAAAAGTTG | TAAAATATTT | GATTTCATTG | 480
| ATACTTGCTA | TTATCATTGT | ACTGTTCGTA | CAAACTTTTG | TAATAGTTGG | TCATGTCATT | 540
| CCGAATAATG | ATATGTCACC | AACCCTTAAC | AAAGGGACGT | GTTATTGTAA | ATAAAATTAA | 600
| AGTTACATTT | AATCAATTGA | ATAATGGTGA | TATCATTACA | TATAGGCGTG | GTAACGAGAT | 660
| ATATACTAGT | CGAATTATTG | CCAAACCTGG | TCAATCAATG | GCGTTTCGTC | AGGGACAATT | 720
| ATACCGTGAT | GACCGACCGG | TTGACGCATC | TTATGCCAAG | AACAGAAAAA | TTAAAGATTT | 780
| TAGTTTGCGC | AATTTTAAAG | AATTAGATGG | AGATATTATA | CCGCCTAACA | ATTTTGTTGT | 840
| GCTAAATGAT | CATGATAACA | ATCAGCATGA | TTCTAGACAA | TTTGGTTTAA | TTGATAAAAA | 900
| GGATATTATT | GGTAATATAA | GTTGAGATA | TTATCCTTTT | TCAAAATGGA | CGATTCAGTT | 960
| CAAATCTTAA | AAAGAGGTGT | CAAAATTGAA | AAAAGAATTA | TTGGAATGGA | TTATTTCAAT | 1020
| TGCAGTCGCT | TTTGTCATTT | TATTTATAGT | AGGTAAATTT | ATTGTTACAC | CATATACAAT | 1080
| TAAAGGTGAA | TCAATGGATC | CAACTTTGAA | AGATGGCGAG | CGAGTAGCTG | TAAACATTAT | 1140
| TGGATATAAA | ACAGGTGGTT | TGGAAAAAGG | TAATGTAGTT | GTCTTCCATG | CAAACAAAAA | 1200
| TGATGACTAT | GTTAAACGTG | TCATCGGTGT | TCCTGGTGAT | AAAGTAGAAT | ATAAAAATGA | 1260
| TACATTATAT | GTCAATGGTA | AAAAACAAGA | TGAACCATAT | TTAAACTATA | ATTAAAACA | 1320
| TAAACAAGGT | GATTACATTA | CTGGGACTTT | CCAAGTTAAA | GATTTACCGA | ATGCGAATCC | 1380
| TAAATCAAAT | GTCATTCCAA | AAGGTAAATA | TTTAGTTCTT | GGAGATAATC | GTGAAGTAAG | 1440
| TAAAGATAGC | CGTGCGTTTG | GCCTCATTGA | TGAAGACCAA | ATTGTTGGTA | AAGTTTCATT | 1500
| TAGATTCTGG | CCATTTAGTG | AATTTAAACA | TAATTTCAAT | CCTGAAAATA | CTAAAAATTA | 1560
| ATATGAAACA | AATACAACAT | CGTTTGTCGG | TTTAATACT | GATAAACGAT | GTTTATTTT | 1620
| GTTAGTACCA | CAATAAAAGC | TAAGTTCGAA | ATGAACTTAT | AATAAATCAA | TCACAATCAC | 1680
| TTTGTGTTAA | AATATGTGTC | AAAGGAAGTG | AGGGTTTGTC | ATGACATTAC | ATGCTTATTT | 1740
| AGGTAGAGCG | GGAACAGGTA | AGTCTACGAA | AATGTTGACC | GAAATAAAAC | AAAAAATGAA | 1800

```
AGCAGATCCG CTTGGAGATC CAATCATTTT AATTGCGCCA ACTCAAAGTA CATTTCAATT   1860
AGAACAAGCC TTTGTCAATG ATCCGGAATT AAATGGTAGT TTAAGAACAG AAGTGTTGCA   1920
TTTTGAACGA TTAAGTCATC GTATTTTCCA AGAAGTTGGT AGTTATAGCG AACAAAAGTT   1980
ATCTAAAGCT GCAACGGAAA TGATGATTTA TAACATTGTT CAAGAACAAC AAAAGTATTT   2040
AAAACTTTAT CAATCACAAG CAAAATATTA TGGGTTTAGT GAAAAATTAA CAGAACAAAT   2100
TCAAGATTTT AAAAAATATG CAGTAACGCC TGAACATTTA GAACACTTTA TTGCTGATAA   2160
AAATATGCAA ACTCGAACTA AAAATAAGTT AGAGGATATT GCTTTAATAT ACCGTGAGTT   2220
CGAACAACGC ATTCAAAACG AGTTTATTAC TGGTGAGGAT TCATTACAAT ATTTTATTGA   2280
TTGTATGCCG AAATCAGAGT GGCTAAAACG TGCTGATATA TATATTGATG GTTTCACAA    2340
CTTTTCAACG ATTGAGTATT TAATAATCAA AGGATTAATT AAATATGCGA GAGTGTCACA   2400
ATTATATTGA CGACAGATGG TAACCACGAT CAATTTAGTT TTTTAGAAAA CCATCGGAAG   2460
TGTTACGACA TATTGAAGAA ATAGCAAATG AACTCAATAT TTCTATTGAA CGTCAATATT   2520
TCAACCAATT ATATCGCTTC AATAATCAAG ATTTAAAGCA TCTTGAACAA GAATTTGATG   2580
TACTTCAAAT CAATCGAGTG GCATGTCAAG GTCATATCAA TATTTTAGAA TCTGCGACTA   2640
TGAGAGAGGA AATAAATGAA ATTGCGCGAC GTATCATCGT TGATATTCGT GATAAGCAAT   2700
TACGATATCA AGATATTGCA ATTTTATATC GTGACGAGTC TTATGCTTAT TTATTTGATT   2760
CCATATTACC GCTTTATAAT ATTCCTTATA ACATTGATAC AAAGCGTTCG ATGACACATC   2820
ATCCGGTCAT GGAAATGATT CGTTCATTGA TTGAAGTTAT TCAATCTAAT TGGCAAGTGA   2880
ATCCAATGCT ACGCTTATTG AAGACTGATG TGTTAACGGC ATCATATCTA AAAAGTGCAT   2940
ACTTAGTTGA TTTACTTGAA AATTTTGTAC TTGAACGTGG TATATACGGT AAACGTTGGT   3000
TAGATGATGA GCTATTTAAT GTCGAACATT TTAGCAAAAT GGGGCGTAAA GCGCATAAAC   3060
TGACCGAAGA TGAACGTAAC ACATTTGAAC AAGTCGTTAA GTTAAAGAAA GATGTCATTG   3120
ATAAAATTTT ACATTTTGAA AAGCAAATGT CACAAGCGGA AACTGTAAAA GACTTTGCAA   3180
CTGCTTTTTA TGAAAGTATG GAATATTTCG AACTGCCAAA TCAATTGATG ACAGAGCGAG   3240
ATGAACTTGA TTTAAATGGT AATCATGAAA AGGCGGAGGA AATTGATCAA ATATGGAATG   3300
GCTTAATTCA AATCCTTGAC GACTTAGTTC TAGTATTTGG AGATGAACCA ATGTCGATGG   3360
AACGTTTCTT AGAAGTATTT GATATTGGTT TAGAACAATT AGAATTTGTC ATGATTCCAC   3420
AAACATTAGA TCAAGTTAGT ATTGGTACGA TGGATTTGGC TAAAGTCGAC AATAAGCAAC   3480
ATGTTTACTT AGTTGGAATG AACGACGGCA CCATGCCACA ACCAGTAACT GCATCAAGTT   3540
TAATTACTGA TGAAGAAAAG AAATATTTTG AACAACAAGC AAATGTAGAG TTGAGTCCTA   3600
CATCAGATAT TTTACAGATG GATGAAGCAT TGTTTGCTA TGTTGCTATG ACTAGAGCTA    3660
AGGGAGATGT TACATTTTCT TACAGTCTAA TGGGATCAAG TGGTGATGAT AAGGAGATCA   3720
GCCCATTTTT AAATCAAATT CAATCATTGT TCAACCAATT GGAAATTACT AACATTCCTC   3780
AATACCATGA AGTTAACCCA TTGTCACTAA TGCAACATGC TAAGCAAACC AAAATTACAT   3840
TATTTGAAGC ATTGCGTGCT TGGTTAGATG ATGAAATTGT GGCTGATAGT TGGTTAGATG   3900
CTTATCAAGT AATTAGAGAT AGCGATCATT TAAATCAAGG TTTAGATTAT TTAATGTCAG   3960
CATTAACGTT TGACAATGAA ACTGTAAAAT TAGGTGAAAC GTTGTCTAAA GATTTATATG   4020
GTAAGGAAAT CAATGCCAGT GTATCTCGTT TTGAAGGTTA TCAACAATGC CCATTTAAAC   4080
ACTATGCTTC ACATGGTCTG AAACTAAATG AACGAACGAA ATATGAACTT CAAAACTTTG   4140
ATTTAGGTGA TATTTTCCAT TCCGTTTTAA AATATATATC TGAACGTATT AATGGCGATT   4200
```

```
TTAAACAATT AGACCTGAAA AAAATAAGAC AATTAACGAA TGAAGCATTG GAAGAAATTT    4260
TACCTAAAGT TCAGTTTAAT TTATTAAATT CTTCAGCTTA CTATCGTTAT TTATCAAGAC    4320
GCATTGGCGC TATTGTAGAA ACAACACTAA GCGCATTAAA ATATCAAGGC ACGTATTCAA    4380
AGTTTATGCC AAAACATTTT GAGACAAGTT TTAGAAGGAA ACCAAGAACC AAATGTACGA    4440
ATTAATTGCA CAAACATTAA CGACAACTCA AGGTATTCCA ATTAATATTA GAGGGCAAAT    4500
TGACCGTATC GATACGTATA CAAAGAATGA TACAAGTTTT GTTAATATCA TTGACTATAA    4560
ATCCTCTGAA GGTAGTGCGA CACTTGATTT AACGAAAGTA TATTATGGTA TGCAAATGCA    4620
AATGATGACA TACATGGATA TCGTTTTACA AAATAAACAA CGCCTTGGAT AACAGATAT     4680
TGTGAAACCA GGTGGATTAT TATACTTCCA TGTACATGAA CCTAGAATTA AATTTAAATC    4740
ATGGTCTGAT ATTGATGAAG ATAAACTAGA ACAAGATTTA ATTAAAAGT TTAAGCTGAG     4800
TGGTTTAGTG AATGCAGACC AAACTGTTAT TGATGCATTG GATATTCGTT TAGAACCTAA    4860
ATTCACTTCA GATATTGTAC CAGTTGGTTT GAATAAAGAT GGCTCTTTGA GTAAACGAGG    4920
CAGCCAAGTG GCAGATGAAG CAACAATTTA TAAATTCATT CAGCATAACA AAGAGAATTT    4980
TATAGAAACA GCTTCAAATA TTATGGATGG ACATACTGAA GTGCACCATT AAAGTACAAA    5040
CAAAAATTGC CATGTGCTTT TTGTAGTTAT CAATCGGTAT GTCATGTAGA TGGCATGATT    5100
GATAGTAAGC GATATCGAAC TGTAGATGAA ACAATAAATC CAATTGAAGC AATTCAAAAT    5160
ATTAACATTA ATGATGAATT TGGGGGTGAG TAATAGATGA CAATTCCAGA GAAACCACAA    5220
GGCGTGATTT GGACTGACGC GCAATGGCAA AGTATTTACG CAACTGGACA AGATGTACTT    5280
GTTGCAGCCG CGGCAGGTTC AGGTAAAACA GCTGTACTAG TTGAGCGTAT TATCCAAAAG    5340
ATTTACGTG ATGGCATTGA TGTCGATCGA CTTTAGTCG TAACGTTTAC AAACTTAAGC      5400
GCACGTGAAA TGAAGCATCG TGTAGACCAA CGTATTCAAG AGGCATCGAT TGCTGATCCT    5460
GCAAATGCAC ACTTGAAAAA CCAACGCATC AAAATTCATC AAGCACAAAT ATCTACACTT    5520
CATAGTTTTT GCTTGAAATT AATTCAACAG CATTATGATG TATTAAATAT TGACCCGAAC    5580
TTTAGAACAA GCAGTGAAGC TGAAAATATT TTATTATTAG AACAAACGAT AGATGAGGTC    5640
ATAGAACAAC ATTACGATAT CCTTGATCCT GCTTTTATTG AATTAACAGA ACAATTGTCT    5700
TCAGATAGAA GTGATGATCA GTTTCGAATG ATTATTAAAC AATTGTATTT CTTTAGCGTT    5760
GCAAATCCAA ATCCTACAAA TTGGTTGGAT CAATTGGTGA CACCATACGA AGAAGAAGCA    5820
CAACAAGCGC AACTTATTCA ACTACTAACA GACTTATCTA AGTATTTAT CACAGCTGCC     5880
TATGATGCTT TAAATAAGGC GTATGATTTG TTTAGTATGA TGGATGGCGT CGATAAACAT    5940
TTAGCTGTTA TAGAAGATGA ACGACGTTTA ATGGGGCGTG TTTTAGAAGG TGGTTTTATT    6000
GATATACCTT ATTTAACTGA TCACGAATTT GGCGCGCGTT TGCCTAATGT AACAGCGAAA    6060
ATTAAAGAAG CAAATGAAAT GATGGTCGAT GCCTTAGAAG ATGCTAAACT TCAGTATAAA    6120
AAATATAAAT CATTAATTGA TAAAGTGAAA AATGATTACT TTCAAGAGA AGCTGATGAT     6180
TTGAAAGCTG ATATGCAACA ATTGGCGCCA CGAGTAAAGT ACCTTGCGCG TATTGTGAAA    6240
GATGTTATGT CAGAATTCAA TCGAAAAAG CGTAGCAAAA ATATTCTGGA TTTTTCTGAT     6300
TATGAACAAT TTGCATTACA AATTTTAACT AATGAGGATG GTTCGCCTTC AGAAATTGCC    6360
GAATCATACC GTCAACACTT TCAAGAAATA TTGGTCGATG AGTATCAAGA TACGAACCGG    6420
GTTCAAGAGA AAATACTATC TTGCATCAAA ACGGGTGATG AACATAATGG TAATTTATTT    6480
ATGGTTGGAG ATGTTAAGCA ATCCATTTAT AAATTTAGAC AAGCTGATCC AAGTTTATTT    6540
ATTGAAAAGT ATCAACGCTT TACTATAGAT GGAGATGGCA CTGGACGTCG AATTGATTTG    6600
```

```
TCGCAAAACT CCGTTCTCGA AAAGAAGTAC TGTCAACGAC TAACTATATA TCAAACATAT    6660
GATGGATGAA CAAGTCGGTG AAGTAAAATA TGATGAAGCG GCACAGTTGT ATTATGGTGC    6720
ACCATATGAT GAATCGGACC ATCCAGTAAA CTTAAAAGTG CTTGTTGAAG CGGATCAAGA    6780
ACATAGTGAT TTAACTGGTA GTGAACAAGA AGCGCATTTT ATAGTAGAAC AAGTTAAAGA    6840
TATCTTAGAA CATCAAAAAG TTTATGATAT GAAAACAGGA AGCTATAGAA GTGCGACATA    6900
CAAAGATATC GTTATTCTAG AACGCAGCTT TGGACAAGCT CGCAATTAC AACAAGCCTT     6960
TAAAAATGAA GATATTCCAT TCCATGTGAA TAGTCGTGAA GGTTACTTTG AACAAACAGA    7020
AGTCCGCTTA GTATTATCAT TTTTAAGAGC GATAGATAAT CCATTACAAG ATATTTATTT    7080
AGTTGGGTTA ATGCGCTCCG TTATATATCA GTTCAAAGAA GACGAATTAG CTCAAATTAG    7140
AATATTGAGT CAAATGATGA CTACTTCTAT CAATCGATTG TAAATTACAT TAATGACGAA    7200
GCAGCAGATG CTATTTTAGT TGATAAATTA AAAATGTTTT TATCAGATAT TCAAAGTTAC    7260
CAACAATATA GTAAAGATCA TCCGGTGTAT CAGTTAATTG ATAAATTTTA TAATGATCAT    7320
TATGTTATTC AATACTTTAG TGGACTTATT GGTGGACGTG GACGACGTGC AAACCTTTAT    7380
GGTTTATTTA ATAAAGCTAT CGAGTTTGAG AATTCAAGTT TTAGAGGTTT ATATCAATTT    7440
ATTCGTTTTA TCGATGAATT GATTGAAAGA GGCAAAGATT TTGGTGAGGA AAATGTAGTT    7500
GGTCCAAACG ATAATGTTGT TAGAATGATG ACAATTCATA GTAGTAAAGG TCTAGAGTTT    7560
CCATTTGTCA TTTATTCTGG ATTGTCAAAA GATTTAATA AACGTGATTT GAAACAACCA     7620
GTTATTTTAA ATCAGCAATT TGGTCTCGGA ATGGATTATT TTGATGTGGA TAAAGAAATG    7680
GCATTTCCAT CTTTAGCTTC GGTTGCATAT AAAGCTGTTG CCGAAAAAGA ACTTGTGTCA    7740
GAAGAAATGC GATTAGTCTA TGTAGCATTA ACAAGAGCGA AAGAACAACT TATTTAATT     7800
GGTAGAGTGA AAAATTGATA AATCGTTACT AGAACTAGAG CAATTGTCTA TTTCTGGTGA    7860
GCACATTGCT GTCAATGAAC GATTAACTTC ACCAAATCCG TTCCATCTTA TTTATAGTAT    7920
TTTATCTAAA CATCAATCTG CGTCAATTCC AGATGATTTA AAATTTGAAA AAGATATAGC    7980
ACAAGTTGAA GATAGTAGTC GTCCGAATGT AAATATTTCA ATTATATACT TGAAGATGT     8040
GTCTACAGAA ACCATTTTAG ATAATAATGA ATATCGTTCG GTTAATCAAT TAGAAACTAT    8100
GCAAAATGGT AATGAGGATG TTAAAGCACA AATTAAACAC CAACTTGATT ATCAATATCC    8160
ATATGTAAAT GATACTAAAA AGCCATCCAA AACAATCTGT TTCTGAATTG AAAAGGCAAT    8220
ATGAAAGAAG AAAGTGGCAC AAGTTACGAA CGAGTAAGAC AATATCGTAT CGGTTTTCAA    8280
CGTATGAACG ACCTAAATTT CTAAGTGAAC AAGGTAAACG AAAAGCGAA TTGAAATTGG     8340
TACGTTAATG CATACAGTGA TGCAACATTT ACCATTCAAA AAGAACGCA TATCTGAAGT     8400
TGAGTTACAT CAGTATATCG ATGGATTAAT CGATAAACAT ATTATCGAAG CAGATGCGAA    8460
AAAAGATATC CGTATGGATG AAATAATGAC ATTATCAATA GTGAGTATAT TCGATTATTG    8520
CTGAAGCAGA GCAAGTTTAT CGTGAATTAC CGTTTGTAGT TAACCAAGCA TTAGTTGACC    8580
AATTGCCACA AGGAGACGAA GACGTCTCAA TTATTCAAGG TATGATTGAC TTAATCTTTG    8640
TTAAAGATGG TGTGCATTAT TTTGTAGACT ATAAAACCGA TGCATTTAAT CGTCGCCGTG    8700
GGATGACAGA TGAAGAAATT GGTACACAAT TAAAAATAA ATATAAGATA CAGATGAAAT     8760
ATTATCAAAA TACGCTTCAA ACGATACTTA ATAAAGAAGT TAAAGGTTAT TTATACTTCT    8820
TCAAATTTGG TACATTGCAA CTGTAGTATT TTGATTTCA AAAGAATAAA AATAATTTC      8880
GATTAAGTGC AAAGTCCTTG TAGCAGAATG AACACAACTC ATTTTCAAAA TTGTCTTACT    8940
TATTTATTTG TTATTTGATA ACGAAAAAAG TTATAATGTG AATTAAGATA AAGATGAGGA    9000
```

-continued

```
GTTGAGAATG  AATGAAATTC  TTATCATTCA  AGTATAATGA  CAAAACTTCA  TATGGCGTTA   9060
AAGTAAAACG  CGAAGATGCT  GTATGGGATT  TAACACAAGT  ATTTGCTGAC  TTTGCAGAAG   9120
GAGATTTCCA  TCCTAAAACA  TTGTTAGCTG  GTTTACAACA  AAATCATACT  TTAGATTTTC   9180
AAGAACAAGT  ACGTAAAGCA  GTTGTAGCAG  CAGAAGATAG  CGGCAAAGCT  GAAGACTATA   9240
AAATTTCATT  TAATGACATT  GAATTCTTAC  CACCAGTAAC  ACCTCCGAAT  AATGTGATTG   9300
CTTTTGGTAG  AAATTACAAA  GATCATGCGA  ACGAATTAAA  TCATGAAGTA  GAAAAATTAT   9360
ATGTATTTAC  AAAAGCAGCG  TCATCTTTAA  CAGGAGATAA  TGCAACAATT  CCAAATCATA   9420
AAGATATTAC  TGATCAATTA  GATTATGAAG  GTGAATTAGG  TATTGTTATT  GGTAAGTCTG   9480
GTGAAAAGAT  TCCAAAAGCA  TTAGCTTTAG  ATTATGTTTA  CGGCTATACA  ATTATTAACG   9540
ATATCACTGA  TCGCAAAGCA  CAAAGTGAAC  AAGATCAAGC  ATTTTTATCA  AAAAGTTTAA   9600
CTGGCGGTTG  CCCAATGGGT  CCTTATATCG  TTACTAAAGA  CGAACTACCA  TTACCTGAAA   9660
ATGTAAATAT  TGTTACAAAA  GTTAACAATG  AAATTAGACA  AGATGGTAAC  ACTGGCGAAA   9720
TGATTCTTAA  AATTGATGAA  TTAATAGAAG  AAATTTCAAA  ATATGTTGCA  CTACTACCGG   9780
GAGATTATTA  TTGCAACTGG  TACACCAGCT  GGCGTTGGTG  CAGGTATGCA  ACCACCTAAA   9840
TTTTTACAAC  CAGGTGATGA  AGTTAAAGTG  ACTATTGATA  ATATTGGAAC  GCTGACAACT   9900
TATATCGCTA  AATAATTATC  ATTTAAAAAG  CTAACCAGGT  CTTTATATAG  ATTGGTTAGT   9960
TTTTTCTTGC  TTTTCTAAAA  AGGTGTTAAA  GATAAATTAT  TTATAATGTT  ACCATTTTGA  110020
GATGAAAGTG  AAATATTGAT  ATTAAGAAGT  AGTTGATTAT  TTTACAGCAG  ATTCACAATA  110080
TTCTAATAAG  GGCAATGCAA  ATGTCATGTT  CTTCCTCTCA  AATATAGAAG  TGTGGTAGAA  110140
TATATATTCG  TGTATAATCA  AATCTAGATT  AAATTACAAG  CAAGTGGGTA  TTAATCCCAA  110200
GAAGCTT                                                                 110207
```

( 2 ) INFORMATION FOR SEQ ID NO:3:

( i ) SEQUENCE CHARACTERISTICS:
        ( A ) LENGTH: 2082 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 36

( x i ) SEQUENCE DESCRIPTION: SEQ ID NO:3:

```
AAGCTTTCTA  ATCTATCGTT  AATGATTTGC  TTTAAAATTG  GGTCGAAGTT  AATTGAAGGT    60
GTGAAGTGTA  TATCTGTATT  AATAACCATG  TCATTCATTT  GCTGCTTCAC  TTTGTTAACA   120
AGTCTTCCGT  CATATAAAAA  TAATGGTACG  ACAATCAATT  TTTGATACCG  TTCGAGATG    180
CTTTCTAAAT  CATGTGTAAA  ACTAATCTCT  CCATATAGCG  TTCTCGCATA  AGTAGGTTTA   240
TTAATCTGCA  AATGTTGAGC  GCATATTTGT  AACTCTTCGT  GTGCCTTAGT  AAAATTTCCA   300
TTAATATTGC  CGTGTGCAAC  AACCATAACT  CCAACTTGTT  GTTCGTCACC  TGCTAATGCG   360
TCACAAATAC  GTTGTTCAAT  TAATCGTCTC  ATTAAAGGAT  GTGTGCCAAG  TGGCTCGCTT   420
ACTTCTACCT  TTATGTCTGG  ATACCGTCGT  TTCATTTCAT  GAACGATATT  CGGTATATCC   480
TTGAGATAAT  GCATTGCACT  AAAGATTAGC  AATGGTACAA  TTTAAAATG   GTCAACCCCA   540
CTTTGAATCA  ACGTCGTCAT  TACCGTCTCT  AAATCCTGAT  GCTCACTTTC  TAAAAACGCA   600
```

| | | | | | |
|---|---|---|---|---|---|
|ATATCATAGT|GATGTATATC|ATCTTTTACT|AATTCAGAAA|TAAATGCTTC|TAACGCTTGA|660|
|TTCTGTCGTC|CGTGCCTCAT|GCCATGTGCA|ACAATGATAT|TCCCATTCAC|ATTACCAAC|720|
|CCTTTCACAC|GTATTGTATA|CCAAATCATT|TTGTTTTTGT|GAAAAGAATC|ACATTATAAT|780|
|GTAAAATCAG|GGAATTCCCT|GATGCCTGTA|GTCATGCATA|TTCCTTATAC|ATTTTCCCTT|840|
|TTTGTTAAAT|CAAAAAAAGC|GACCGATATA|TGAATCCCTA|CTCAACATTT|ATTTGAGCAA|900|
|GCATCAATAT|ATCGGTCGCT|TGTAGTGTAT|ATTATTATCT|TAAAATGGTG|GTTGGCCTAA|960|
|TATTGTTTCG|TCAAAGCGCT|CGGGTATCAA|TACTTTGCGC|ATGATCACAC|CTAAATCGCC|1020|
|ATCATCATTT|TCATGTTCGC|TGTATATTTC|ATAACCTCTT|TTTTCATAAA|TTTTAAGTAA|1080|
|CCACGGATGC|AATCTTGCAG|ATGTACCTAA|AGTAACTGCC|GCTGACTTTA|ACGTATCTCG|1140|
|CAAAAATGCT|CTTCAACATA|AGTAAGTAAT|TGGCTACCAT|AGCCTTTCCC|TTCATACTCA|1200|
|GGATTTGTCG|CAAACCACCA|GACAAAGGA|TAGCCCGAAA|TACTTTTCAC|ACTTCCCCAA|1260|
|GGATATCTAA|CCGTAATCGT|AGATATAATT|TCATCATCAA|TTGTCATGAC|AAATGTAGTA|1320|
|TTTTTATCTA|TATTTCTTT|AACAGCATCT|AAATTAGCAT|TAACTGAAGG|CCAATCAATA|1380|
|CCTAGTTCTC|TTAGAGGCGT|AAATGCTTCA|TGCATGAGTT|GTTGCAATTT|TCTGCATCT|1440|
|TGTTCACTTG|CGAGTCGAAT|CATCGTTTTT|GTCATATTAA|TCCCCACTCT|TTTTTAAATG|1500|
|ATTTAACCAT|ATTTTATTTT|TAAAATAAAT|ATCCATCAAA|GTGTATCAAT|AAATTTATCA|1560|
|CATGTCAGAA|AGTATGCTTC|ATCTGAATAC|ACCAATACTC|TCATGAAACT|TATTAAAAAT|1620|
|TACTCTCTCA|ACGTAAAAAA|ACCATTCAAA|TTCATGAATG|GTTGGAAGA|ATGATTCATT|1680|
|GTTACGCTAT|TTAATCACTA|CATCTTAATT|ATTGTTGCTC|TAAACGATTA|CGCTTACCAT|1740|
|TTAAGAAAGC|ATAAACGAGA|CCTACAAAAA|TACCGCCACC|GACAAAGTTA|CCTAAGAAAG|1800|
|CAAAAACGAT|ATTTTTAAA|ACATGTAACC|ATGAAACTGC|ATCAAGGTTA|AAGAATACCA|1860|
|TACCTGCATA|TAGACCTGCA|TTGAACACAA|CGTGCTCATA|TCCCATGTAT|ACAAAGACCA|1920|
|CGACACCACA|AGCTATGAAG|AATGCCTTTG|TTAAGCCGCC|TTTGAATTGC|ATAGAGATGA|1980|
|AAATACCAAT|ATTAATAAAG|AAGTTACAGA|AAATACCTTT|TGTAAAAATA|TTCAACCATG|2040|
|TTGAATCAAC|AGTCTTTTTC|TGAACTAAAG|CTGTTAAAGC|TT| |2082|

( 2 ) INFORMATION FOR SEQ ID NO:4:

( i ) SEQUENCE CHARACTERISTICS:
        ( A ) LENGTH: 2885 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 77

( x i ) SEQUENCE DESCRIPTION: SEQ ID NO:4:

| | | | | | |
|---|---|---|---|---|---|
|AAGCTTTTGA|TTAATTTGGG|CTTTAAAGTA|TTCCCAATTA|TAATTCTTCA|TGATTTTCTT|60|
|ATTGGATTTC|GAATTTGGTT|TCATGCATTG|TTGCCTCAAA|GAACATGCTG|AACAGTCATC|120|
|GCATTCATAT|AGCTTGAAGT|CACGTTTAAA|ACCATATCTA|TCATTACGGT|ATGCATATCT|180|
|TTTAAAACCT|ATTCTTTTGT|TATTAGGACA|TATAAATTCA|TCATTAAGTT|CGTCATATTT|240|
|CCAATTTGA|GTGTTAAAAA|TGTCACTTTT|AAACTTTCTA|GTTTATCTT|TAATAAACAT|300|
|GCCATACGTA|ATAAGTGGCG|TTTTATTAAA|ACATCTATAA|TAGCCATATA|GTTTGCTCA|360|
|CTATCATAAC|TGCATCAGCT|ACATTAACTC|TGGTAATACC|GAGGATTTGA|ATCATTGTTA|420|

```
AAAATGGAAT TAAAGTTCTA GTATCTGTTG GGGTTTGAAA TAGGTCATAG GATAAAAAAA      480
TTGAGAATTT GTCGCTATTT GTAAATTGTA TCCTGGCTTA AGTTGGCCAT TTTTCATATG      540
GTCTTCCTTC ATTCTCATAA AAGTTGCATC ATGATCAGCC CAGAAAGCTA TTTCTATCTT      600
TAAGAATCCA TTTTTGTTCT TCATATTTAT TTTTCTTTC  GGAATAATCA TCAAATTTCT      660
TTTTGAACTT CTTAATCTCA GTTCTTTTTT ACGGGTCTGT TTTCTAATTT GAGCACTCTT      720
CGTTCTAAAT AGAATGATTT AAATCTTCGA TTTCTTTTAT CTAAATGACT ACCAATTAAA      780
TCTATTTCTT CTCGTGATTT TGAATACTTT TCTTCCACAC AAATGTATAT CTATTGGCAT      840
TAGCTTCTAC TTATGTACCA TCAATAAAAA TTGAATTATT ATCAATAAGA TTTTGCTTTA      900
AACATTGACT ATGGAACTGA ATAAATAAAG ATTCAATTAA CGCATCAGTA TTAGGATTCA      960
CTCTAAAACG ATTAATAGTT TTATAAGAAG GTGTTTGATC TTGAGCTAAC CACATCATTC     1020
GAATACTGTC ATGAAGTAAT TTCTCTATTC TACGACCAGA AAATACAGAT TGAGTATATG     1080
CATATAAGAT GATTTTTAAC ATCATTTTTG GATGATAGGA TGTTGCGCCA CGATGATGTC     1140
TGAATTCATC GAATTCGCTA TCAGGTATCG TTTCAACAAT TTCATTACA TATCGCGAAA      1200
TATCATTTTA AGGAATTCTA ACAGAAGTTT CTATTGGTAG TGTAAGTTGG GCAAAGTGTC     1260
TTATTTTTTT AAAGTATGTA AAAGTAAAAT TACATGTTAA TACGTAGTAT TAATGGCGAG     1320
ACTCCTGAGG GAGCAGTGCC AGTCGAAGAC CGAGGCTGAG ACGGCACCCT AGGAAAGCGA     1380
AGCATTCAAT ACGAAGTATT GTATAAATAG AGAACAGCAG TAAGATATTT TCTAATTGAA     1440
AATTATCTTA CTGCTGTTTT TTAGGGATT  TATGTCCCAG CCTGTTTTAT TTTCGACTAG     1500
TTTGGAGAAT TTATTGACAT TCACATTATT TAAACGGCAA CAAAGATTGT TTTATTTTGA     1560
TAGGCATTAT ATGGTGTTAA AAAATTTGCA TGAAAATTAA AAAATGCTTC GTTCAGGAAG     1620
GTGTCGTAAT TTACCTATTT GCTGAATGAA GCATTTTATT TTTAAATATG ATAGCCAATA     1680
TAACAAGCTA TAAATCCAAT GATGAATTGT AAAAGTGAAT AATTGAGAAA AAGGTTAATA     1740
TCAAATTTTG GTGTCATCAT TAATGTAAGT TCCTTGGCTA ACGTTGAGAA AGTTGTTAAG     1800
CCACCTAAAA AAACCGGTGA CAAAGAACGC AGGGAACCAT GAGATTGAAA TTGATAGGCC     1860
TATAGTTAAT CCAATTAAAA AACTACCAAC TAGATTTACT ATCAATGTTG CGATAGGTAA     1920
CTTTGAAGTA AATTTATGAT TAAAATAATC AGTAATGGCA CTTCTAGCAA TTGCGCCAAA     1980
ACCGCCGCCA ATCATGACTA AAATGATTGA TATCATGATA AACCACCACC TAGTTTTATA     2040
CCGACGTAAC ATAACAAAAT ACCAAGACA  TAACTTGTTA CAGCATATAG TAGTAAAGTT     2100
ATAAATTGTT GATGATCAAA CATATGTATT AATTCTAATT GAAATGTTGA AAAAGTCGTT     2160
AAAGCACCAA GAAAACCAGT CGTAATAGCT TTTTTTAGGG TCGGATGGTT TGAAAAAAAT     2220
GCAATTGTTA AGGCTGTTAG CAATCCCATT ACAAAGGCAC CAGTCAAATT GGCTATCAGT     2280
GTTCCGATTG GAAAACCTCC GTCAGTATTC AGAAAAGAAA TGAGGTAACG TAATAAAGCG     2340
CCTAAAGCAC CACCGATAAA AATATATACA TATTGCATTT GGTTCACCTC GAAAAGAAGT     2400
AGTTGAATT  TAAAAAGAG  GTTTTGGCAA CACGACGACA AAAATTGTCG ATGCATTATC     2460
AAACCTCATT ATATGTTATA TCTTGTTGTA TAACTATAGC GATTAGATGC ATAGTTATGA     2520
TTTCGAAAAT CTAATATTTT TTATACGCAA CAACGTCATC AAATTGTTTT ACTCATTATA     2580
GCATGATACA TTGTATTGTT TTGTATTAAC GCTACATTGA CATTTTATCT TTTTTAAATA     2640
AAACCGAATG TACGACAATT GAAAGATAT  GTACTAAAAT AACAATTAGA ATAATCCAAG     2700
GCAAACTTTT ACTCGCAATT CTAATCCAAT CTGCATCAGG CTTAGTGAT  TTAATTGAAC     2760
GATCTGCAAA AATTATAGAC AAAATTAGTA CAATTGAGTT AATAACACTG CAGAAAAGTA     2820
```

-continued

```
TTAATTTAAT AAAAGAATTA AAAAATCCAC TTAGGAAAAC GTTATTTGTA TTAAAGAAAA    2880
AGCTT                                                                2885
```

( 2 ) INFORMATION FOR SEQ ID NO:5:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 3

( x i ) SEQUENCE DESCRIPTION: SEQ ID NO:5:

```
AAGCTTCACA ACTTGAAAAT ATAGCACAAA CATTAAAGGA TTTAGGTAGA AAACGAGCAA      60
TTTTAATTCA TGGTGCAAAT GGGATGGATG AGGCCACGCT TTCTGGTGAA AATATCATTT     120
ATGAAGTTAG CAGCGAAAGA GCATTAAAAA AATATAGTTT AAAAGCAGAA GAAGTCGGTT     180
TAGCTTATGC AAATAATGAC ACGTTGATAG GTGGTCACC  TCAAACAAAT AAACAAATTG     240
CATTGAATAT CCTAAGTGGC ACGGATCACT CAAGTAAACG AGATGTAGTT TTGTTAAATG     300
CTGGAATTGC TTTATATGTT GCTGAGCAAG TGGAAAGTAT CAAACATGGC GTAGAGAGAG     360
CGAAATATCT CATTGATACA GGTATGGCAA TGAAACAATA TTTAAAAATG GGAGGTTAAG     420
TAATGACTAT TTTAAATGAA ATTATTGAGT ATAAAAAAC  TTTGCTTGAG CGTAAATACT     480
ATGATAAAAA ACTTGAAATT TTACAAGATA ACGGAAATGT TAAGAGGAGA AAGCTGATTG     540
ATTCACTTTA ACTATGATAG AACATTATCA GTTATTGCTG AAATAAAATC GAAAAGCCCA     600
TCTGTACCTC AATTACCGCA ACGTGATCTT GTTCAACAAG TTAAAGATTA TCAAAAATAT     660
GGTGCTAATG CTATTTCAAT ATTAACTGAT GAAAAATACT TGGCGGTAG  TTTTGAACGA     720
TTAAATCAGT TATCAAAGAT AACATCGTTA CCAGTTTTAT GTAAAGATTT TATTATTGAT     780
AAAATTCAAA TAGATGTTGC AAAACGAGCT GGTGCATCTA TTATTTATT  AATAGTAAAT     840
ATTTTAAGTG ATGACCAATT AAAAGAATTG TATTCATATG CAACAAACCA TAATTTAGAA     900
GCTCTAGTAG AAGTTCATAC AATTAGAGAA CTTGAACGTG CACACCAAAT TAACCCTAAA     960
ATTATTGGTG TTAATAATCG TGATTTAAAA CGATTTGAAA CCGATGTTCT ACATACAAAT    1020
AAATTACTTA AGTTTAAAAA GTCTAATTGC TGCTACATTT CAGAGAGTGG CATTCATACA    1080
AAAGAAGATG TTGAGAAAAT AGTAGATTCA AGTATTGACG GTTTACTTGT AGGGGAGGCA    1140
TTAATGAAAA CAAATGACTT AAGTCAGTTT TTTGCCTAGT TTAAAGTTAA AGAAGAATCT    1200
CTATGATAGT TAAATTTTGT GGTTTTAAAA CCGAAAGTGA TATTAAGAAA ATTAAAAAAT    1260
TAGAAGTTGA TGCAGTAGGG TTTATACATT ATCCCGATAG TAAGAGACAT GTCTCACTGA    1320
AACAATTAAA ATATTTGGCT AAAATAGTGC CAGATCATAT AGAGAAAGTA GTGTCGTAGT    1380
AAATCCTCAA ATGTCCACCA TAAAGAGAAT AATTAATCAA ACTGATATTA ACACAATCCA    1440
ATTACATGGA AATGAAAGCA TTCAATTAAT TAGAAATATT AAGAAACTTA ATTCAAAAAT    1500
AAGAATCATA AAAGCAATTC CAGCAACAAG AAATTTAAAT AATAACATTC AAAAGTATAA    1560
AGATGAGATA GACTATGTTT ATTATAGATA CACCATCAAT CACATACGGA GGGACAGGTC    1620
AAAGTTTTGA CTGGAAATTA TTAAAAAAAA TAAAGGCGTT GATTTTCTCA TTGCGGTGGT    1680
TTGGATTTTG AAAAGATAAA ACGATTAGAA ATATATTCAT TTGGACAATG TGGTTATGAC    1740
```

| | | | | | | |
|---|---|---|---|---|---|---|
| ATCTCAACTG | GCATTGAGTC | ACATAATGAA | AAAGATTTTA | ATAAGATGAC | TCGAATATTA | 1800 |
| AAATTTTTGA | AAGGAGACGA | ATGATTAATG | AAAATTCAAA | CAGAAGTAGA | TGAATTGGGC | 1860 |
| TTTTTCGGTG | AATATGGTGG | CCAATATGTA | CCTGAAACAT | TGATGCCAGC | TATTATTGAA | 1920 |
| CTTAAAAAAG | CATATGAGGA | CGCGAAATCA | GATACTCACT | TCAAGAAAGA | ATTTAATTAT | 1980 |
| TATTTAAGTG | AATATGTTGG | TAGAGAAACG | CCTTTAACAT | TTGCTGAATC | ATACACAAAA | 2040 |
| TTGTTAGGTG | GTGCCAAAAT | ATATCTTAAA | AGAGAAGACT | TAAATCACAC | TGGTGCTCAT | 2100 |
| AAAATTAATA | ACGCGATAGG | ACAGGCACTA | TTAGCTAAAA | GGATGGGGAA | AACTAAATTA | 2160 |
| GTAGCCGAAA | CAGGTGCTGG | TCAACATGGT | GTAGCAAGTG | CCACCATCGC | TGCTTTATTC | 2220 |
| GATATGGATC | TTATTGTTTT | CATGGGAAGT | GAAGATATCA | AACGTCAACA | ACTTAACGTA | 2280 |
| TTTAGAATGG | AATTGCTAGG | AGCTAAAGTA | GTGTCTGTGT | CAGATGGGCA | AGGAACACTA | 2340 |
| TCAGATGCTG | TAAATAAAGC | TT | | | | 2362 |

( 2 ) INFORMATION FOR SEQ ID NO:6:

( i ) SEQUENCE CHARACTERISTICS:
        ( A ) LENGTH: 8654 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 22

( x i ) SEQUENCE DESCRIPTION: SEQ ID NO:6:

| | | | | | | |
|---|---|---|---|---|---|---|
| AAGCTTGTTT | TATTGCTTAG | TTATATTTCC | AATAACACTC | ATTTTATATG | TACGTATTGC | 60 |
| CAAAAAAAT | TATCTATACA | GTAATAAGTA | TGAAATGAGA | ACTGGAATAA | TCATTGGTAT | 120 |
| TATTGCTTTA | ATTCTAGTAA | TTATGCAAGG | GTTTCACTTT | AACTGGGCTA | TTATTCCTAT | 180 |
| TTCTATCTAT | GGTCATCAGT | TTGTATTTTT | CGCTGGAATT | ATTTAAGTC | TTGTTGGTAT | 240 |
| ATTCTTTAAA | CGTATAGAAT | TTGTAGGAGT | TGGCTTACTA | TTTTGTCAAA | AACATAGATG | 300 |
| CAATGGTAAC | TGACCCGGAA | ATTGCACAGT | TTTTCTCTTT | AGCAATTTGG | ATTATACTTG | 360 |
| TTGTGCTAAT | CATTTTTTAT | ACGATACGTT | TATCTGAACG | CACTAAATCA | TCATCATATA | 420 |
| CAAAGATTTA | AACTCAGAAA | ATATGCTAGA | CATATCTTTC | TGAGTTTTTT | AATTTATTAA | 480 |
| AATATATCAT | TTGTTTACCA | TATAAGTTTG | TTTTAGAAAA | TGAATCACTA | TTTTAATATA | 540 |
| CAAATAATTT | AATTACACTG | AAAATAACCT | AAAAGCGTAA | CACTATTTTA | ATATGGGTAT | 600 |
| ATAAATGACT | AAAGGGAGGT | GCCAAGATGA | ATAAAATTCA | AATTTGTAAT | CAGATTGAAC | 660 |
| TTAACTATAT | TGATGAAGGC | GAAGGCATCC | CCATCATTTT | AATTCATGGA | TTAGATGGAA | 720 |
| ACTTGGCAGG | ATTTAAAGAT | TTAAAAAATG | AACTCAAGAA | GCAGTATAGA | GTAATTACTT | 780 |
| ATGATGTCAG | AGGTCATGGA | AAATCTTCAC | GAACAGAATC | ATATGAATTA | AAAGATCATG | 840 |
| TTGAAGATTT | AAATGATTTA | ATGGGAGCAT | TAAATATCGA | TTCTGCACAT | ATTTTAGGAC | 900 |
| ATGATATGGG | GGGCATCATT | GCGAGTGAAT | TTACTGAAAA | ATATCAATAT | AAAGTGATTA | 960 |
| CATTGACAAT | TGTTTCGGCC | AAAAGTGAAG | ACATTGCAAA | TGGTTTCAAC | AAATTAATGG | 1020 |
| TTGATTACCA | AGAAGAATTA | GCAGGCTTTA | ATAAATCTGA | GGCAATGATT | ATTTTATTCT | 1080 |
| CTAAATTATT | TAAAGAGAAA | GATAAAGCAA | TGAAATGGGT | ATCAAAGCCA | AAAATTATAC | 1140 |
| AATAGACCAA | CTCCGGAAGA | AAGTGCAATT | GCAGTACGTG | CATTGCTTAA | TATTAAAGAT | 1200 |
| TTAACTCGTG | TTCATCATAA | TGTGTCCATA | CCTACTTTAA | TTGTGAATGG | TAAGTATGAC | 1260 |

```
CCACTCATAC AAAATAAAAG TCATTATGAT ATGGATCAAT ATTATGATCA AGTTACAAAA      1320
ATTGTATTTG ATAATTCAGG ACATGCACCA CATATCGAGG AACCAGAAAA ATTCCTGAAA      1380
CTCTACTTAG ATTTTGTTAG TTAAAAAATA AGAACATAAA TAAAAACCCT TAAATGATTA      1440
TTGTCGGAAA ATCATTTGAG GGTTTTGTAG TAGCAGTAAA GTTGGACTC AGATCACTAT       1500
CGTATTAACT TAATAAAGA GTAAACAGT CTTATCTTTC ATAAGTGAAA GAAATATCTG        1560
TTTNACTCCC TAGCCATTAT ACTTCATTTC ATTATTTGCT TCTGTGATAC GGTTGTTTAC      1620
TCGTTTAAGT AAATCATCGA TTTTTTTACG CTGCTTAGAA TCTACTAAGA TTAAAACAGT      1680
TCTTTCATCG TGTTCATTAC GTTTTTTATT AAAGTAATTT TCTTGAGATA AATTTTTAAC      1740
AGCTTTAACA ACTTGAGGTT GTTATAATT TAAGTGATTG ATAATATCTT TAAGATAATA      1800
TTCCTCTTCT TTATTCTCAC TAATATAAGT TAATACTGCA AATTCTTCAA AGCTGATTGA      1860
GAATTCTTTT TTAATTATTC CTTTAATCT GTCAGCATAA GTGACCATAG CTAATAATTC       1920
AAAGCAGTCA TTGATTTTG AAATAGCCAT TAATGAAACC TCCCTATTTA TATCATATCC       1980
ATAAATCTTA AAACCCATCT TTTTAAATTT AAAGATAGTT AATTATATTA TTGAATTAAG      2040
ATTACTTGGA TACTATACCC TAATTTATTA ATTTATATCT ATTTTTCTTA TGAAAATACG      2100
AAAGTGTCCG TCATAATATA GTATTAATTT AAATTTAAAG AATATATTTA ATGCTATATT     2160
ATTTAGTTAA TTATAACTAA ATAAAATTAA GAAGTAAACA AATAAGTGTT TATAAAACAA      2220
ATTATCTTTT AAAGTTTATA CTTGAATTAG CAATGTAGCA TTTGCTATAT TCAAAAAAAT     2280
AAGATTGTTT CTAATTTTCC TTAATTTAAT AAAAATTATA CTAAAAGAA TACTTTTTGG      2340
AAAGAATTTT ACTAACATTT TTTATATATA AATGTTTATT AATTTAGAAG TAGGATTTTT     2400
AACAACTTTT TCATCTATCA ATAAGCCTTT AGTTATATTA ATATACCCAC TTTTTAAACT     2460
CTTTTGTAT GTTACTTCTC TTTTTGTAGA ATTAAAACAT AGCGTTTTG AACAATAGCT      2520
GACGTAGGTA ACTCTATGTC ATTTGAGGCT AATTTGATTT TAAAGTGTGT TCCAATTTGA    2580
TGATTGGGTT GTGTAGAAAG TAAAATGTCG TAATATGAGA CGCCATTTTT TATTTTTGAT  2640
GGTATATTCG AAATTTCTTT AATTTTACTA GTAAATTGAG TGTTGTCACT AGATGTTACA    2700
GAAATATTTT GATTTATTTT TAATAAATTC AACTCAGATT CTGATATATT AGCACGAATA     2760
ATACGTTCGT TGCTATTAAT TTGCACTATC TTTTCGTTTG GTTTGAAGG GATAGAATTA     2820
ATATATGAAA TACTTCCATT AATTGGTGAA AATAAAGTGG ATTTAATTGA GGATTTAGTT    2880
TGAATCATTT GTAATTTTAG CTGATTAAGG AATGAATAAT AATGTAAATC ATTTTTAGAA    2940
TTTAAAGTTT TGTTGTTACG TTCATTACTA AGTGTATTTT GGAGTTCCTC ATATAAATGA    3000
TCTTTTTCAT AATTGTAATA TTCTAACACT GGAGTGTTTT TAGATACTTT GCTATGATTT   3060
TTTACTAAAA GTTTTTGGAG TTGTCCTAAA GTGGGAGTGT AGTAGAAAAT ATAGCTGTTA   3120
AGAGGGCTT GTATACCAGT TGTTGAAAGG AGTAATTTGG GCTTTGCTTT TATAGTTTTT    3180
ATATTTTAA TATCTTCTGT TTTAGAAGTT AATTTAGAGA AAGTAATGTA ACTAAAACTA    3240
CAAGTTGTGA GAATGAAAAT GAATAGTAAT GAAGAAATAA CGATGCGTTG CTTGGTCATG    3300
GATGTTCACC TCATAATATT ATTGTGAGGT TATTATACAC TATTATTTTA AATGAAATAT    3360
ATTAATTTTA AATAAGCATT ACTTTTGGTT TGTATATTGT TTTATTTCAA AAAATAAAGT    3420
AAATCAATTT AATAAATTGA AAAATAGAAG GCTATCTTTA ATTTAAAAAT ATATGATTCT    3480
ACATAAATGT TACTATAAGA AGAATCACTC ATAAAAACTG CCAACAAAGA CAAAATCTTT    3540
GTTGGCAGTT CGAAATAGAC ATTTATTTGT ATGAGGAATC TACATTAATA TAAGCGGATA    3600
ATTTTTATTC AGAATAAGGA ATTTAAAAATA ATCGTAATAA AATAATACCT ATAGCTATAC  3660
```

```
ATAATAATCC ACCTAACTTA CGTGATGTTA TTTTGTTTTT AGGTGAACCC AACAAACCGA    3720

AATGATCGAT AATAATACCC ATAATCATTT GGCCCATCAT AGCAATTATA GTAGTTAAAG    3780

CTGCTCCTAA GAAAGGCATT AAAATAATAT TAGATGTTAC GAATGCCATT CCTAGTATCC    3840

CTCCAATAAA ATAAATAGAT TTAATCTTAC CTAGTGTTTT ATGAGTAGAT GATATTTTCA    3900

GACTACGATT AAATACTAAT GTTAATATAA ATAACGCTAT TGTACCAACG CTAAATGATA    3960

TGAGTGAAGC AAATATGGAT GAGTGTGTGT GTTGAGCCAG TGTGCTGTTG ATTGTTGTTT    4020

GGATTGGCGG ACGAAACCAA ATACGAATCC AATAAGCAAC CAGAATACTA TTGGTGTATT    4080

CTTATGTCTA TTAACAGGAT GTCTACGAAC ATAATTCATA AATATAATTC CAGTAATTAA    4140

AAATATAATT CCAACACCTT TAAATAATGT AAAAGATTGT TGATGGGCGC CAATAATCC     4200

AAATGTATCA ATGATTACAC CCATAATAAT TTGCCCTGTA ACCGTAATAA CAACAGTAAG    4260

TGCTGCGCCT AATCTTGGTA ATAATAATAA GTTCCAGTT AAATAGATAA CACCTAATAG     4320

TCCTCCTAGG ACCCAAGTAT AGTTAAGTGT TTGCTTAGAA AAGAATTCTG GTGTTAATAC    4380

TTGTGGATGA ATAATGATAT TAAGCACAAG TAAGCATATT GTTCCGACAG CAAAAGATAT    4440

GGTTGAAGCA TAAAAAGATG AACGGGTAAA TTGGCTTAGC CTTGAGTTGA TTGAAGTTTG    4500

AATAGGAAGT AACATGCCAA CAAAAATTCC TAAAAGATAT AGAAAAAACA ATGATAAAAA    4560

CCAACTTTCT CAATTTAATA TGATTATCAT ACCATTCATA ATCATGTTTC TAAAATGATT    4620

GAGCCATAAG CAAAGTATAG AAATAAGTTG TGAATGTTCC GAGGTGTCAT ACAGCCGATA    4680

CTATTTGAT GAATCATTAT AATAAATGC ACATTAAACA AGTTTTAGAA TTAAAAAAG      4740

CGAGACATCA TTTTGAATTT GATATCTCAC TTCATATTAA TAAAGAACA ATGTAAATTA    4800

AGTTCTTTTT TAGACTTGAA CAATTTTAAA AAATTTGTTC TTCGATAAGT CTTTTTTATG   4860

ATTTTAGTAC TTTAAATAAA GCGTCAAAAA TAATGTTTTA TGAATTAATT TTTATCTTCA   4920

AATATAACAG TTGTCCTTTT ATCAATAAGT TGTGCAGCAT AAATTTTGAC AGGCTTTCCC   4980

AAACTAAATC TTAAAATGTC TAATTCTAAA ATGTCTAATT CTAAAAGTTG GTTCATACTT   5040

TCTTTAATTA ATTGTTCTGT AGTAATAGCG TTAAAATCGG GTAATAGTAA TTTGACGGGT   5100

TTATTAAGAT TTGATTTAAA TACGAGTTCC AAAGTTTTTG ACATACTGAT GTATCCTCCT   5160

TAAATTAAAG ATTCTGTTTT AACGATCTCG ACTTTGTCAT ACTCTTCGCC ACTGAACGTT   5220

CAATGATGGA ACGAAAAGAT TTGATTTGAT CATTAGAAAC AAGCGGATTA ATGTTAGAAA   5280

AACGACGCTT ATGTTCGACT ACTTTACCTT CAGAATTATG TTTGATTTGA GTAAAGATAA   5340

TCGTCACTTG ATTGACTTCA TTCATAATAA AACCTCCTTT CACTATATAT ATCGAAATAG   5400

ATTGAAAAAA AAGGACACAT TTTTGAAAA ATATAGGCAA ATGCCTTTGA TGTGATACAA    5460

ACGTCATTTA TCATTAATTA TGAAACCTGT TTTAGAAGGT ATATGAGGTA AGTAGAATTG   5520

TTAAGTTGTA AAAGAAAAA TTGGAACCTG ATATTTAAAA TAACCAACTT AAAAGATTGA    5580

TCAGTGTCTA AAATTACTAT TTATATATGA ATTAAAATAT TAAGATCTCC CAATATGAGA   5640

ATGAATTAGT TTAAGTTTAT CGATGATTGA AAAATTATAG CCTCATGGAT TCTATCTTAT   5700

ATAAAATAAA GTTCTATTCC CTTTTGGATA TAAATAAGAA TAGTTACCTT TTTGTGATAT   5760

GCCAATTCAG AAAAAAAGCG ACAGTGCTTG AATCTATGTA TGCTCAATAA ACTCATTCAA   5820

ATCAACTAGC AATATCAAAT CATAAATCGT GTTGCACCAT AATAAGGATT AAAACCTGTT   5880

AGTTAACTA ATTTAAGAAA AACATTTGAT TATCTTCTCT TTCAATCGGG AATATTAATT    5940

TCTATCATTC AACAATATTT TGGATATCAG ATAACTTAAG AAATATTGAG ATTTATTGAA   6000

ATACGATATG TTTCAAATCG CCATACAATG ATTACACTTA ATAAATGATT ACACTTAATA   6060
```

```
TAAATGTAAA AAGAAAAGGA GGGGTTAAAT GAGTTTAGTA TATCTTATGG CGACTAATTT      6120
ATTAGTCATG CTCATAGTTT TATTCACTCT GAGTCATCGT CAACTAAGAA AGGTTGCGGG      6180
CTATGTTGCA TTAATAGCTC CTATTGTGAC ATCTACATAT TTTATTATGA AAATACCAGA      6240
TGTGATTCGA AATAAGTTTA TTGCTGTTCG ATTACCATGG ATGCCTTCAA TTGATATTAA      6300
TTTAGATTTA AGATTAGATG GTTAAGTTT AATGTTCGGC TTAATTATTT CGCTAATAGG       6360
TGTGGGTGTA TTTTTTTATG CTACGCAATA TTTATCCCAC AGTACGGACA ATCTTCCTAG      6420
ATTTTTCATC TATTTACTAT TATTTATGTT CAGTATGATT GGCATTGTAA TAGCTAATAA      6480
TACCATCTTA ATGTATGTAT TTTGGGAACT CACAAGTATT TCCTCATTCT TGCTTATATC      6540
CTATTGGTAC AATAATGGTG AAAGTCAATT AGGCGCCATT CAATCTTTCA TGATTACAGT      6600
GTTGGTGGG CTAGCGTTAT TAACAGGATT TATCATTTTA TATATCATTA CAGGAACAAA      6660
CACAATTACT GATATCTTAA TCAACGCAAT GCAATTTCAC GACATCCTTT ATTTATACCA      6720
ATGATTTGA TGCTATTATT AGGTGCTTTT ACCAAATCTG CACAATTTCC GTTTCATATT      6780
TGGTTACCAA AGGCCATGGC AGCACCTACA CCAGTAAGTG CTTATCTTCA TTCGGCAACA      6840
ATGGTAAAGG CTGGAATCTT TTTACTATTT AGATTACAC CTTTATTGGG ACTTAGTAAT       6900
GTTTATATTT ATACAGTGAC ATTTGTTGGT CTAATAACTA TGTTATTTGG ATCTTTAACT      6960
GCTTTACGAC AATACGACTT AAAAGGTATA CTCGCTTATT CTACAATAAG TCAATTAGGT      7020
ATGATTATGA CAATGGTAGG TCTAGGTGGC GGTTATGCTC AGCACACATC AGATGAATTG      7080
TCTAAGTTTT ATATTTAGT TTATTTGCT GGCTTATTCC ATTAATGAA TCATGCGGTT         7140
TTTAAATGTG CATTATTTAT GGGCGTTGGT ATCATTGATC ACGAGTCCGG AACACGTGAT      7200
ATTCGTTTGC TAAATGGTAT GCGTAAAGTC TCCCCTAAAA TGCATATTGT CATGTTGCTC      7260
GCTGCATTAT CTATGGCAGG TGTTCCTTTT TTAAATGGCT TTTTAAGTAA GGAAATGTTT      7320
TTAGATTCGT TAACTAAAGC AAACGAACTT GATCAATATG CTTCGTATT AACGTTTGTG       7380
ATTATTTCAA TAGGTGTCAT CGCGAGTATA TTGACTTTTA CTTATGCACT TTACATGATA     7440
AAAGAAACAT TCTGGGGAAA TTACAATATA GAAAAATTTA AACGTAAACA AATACATGAA      7500
CCATGGCTAT TTAGTTTACC AGCTGTGATT TTAATGTTAC TCATTCCAGT TATCTTCTTT      7560
GTTCCAAACG TTTTTGGCAA CTTTGTTATT TTGCCCGCAA CCAGATCTGT ATCTGGGATA      7620
GGGCGGAGGT TGATGCATTT GTGCCACATA TTTCTCAGTG GCATGGTGTG AATCTCCATT      7680
AATTTAAGA TAGTGTATAT ATTGGACTAT TTAGCTCTA GTGTGATTGG AAAGAGGTTA        7740
CGCATCAAAT AATCAAAAGT GCTCGATTAC AGTGGCTATC GGAAATTTAT AGAGAATTTG     7800
AATTATACTC AGCCCGTGGT ATACGTGCAT TGATGAATAA TAAATTGAAT TATTACATCA      7860
TGATTACATT ATTTATTTTT GTAGCTATTG TAGTTATGGA TATTTGACTG TGGGTTTTCC      7920
TCATGTACTC AGCTTCATAT TAGTTCTTTC GGACCGTTGG AAGTTATCTT ATCAGTTGTA     7980
ACATTGATTA TCGGCATTTC ATTAATCTTT ATTCGTCAAC GACTAACGAT GGTGGTATTG      8040
AATGGAATGA TTGGATTCGC AGTTACATTA TATTTATTG CAATGAAAGC TCCAGATTTA       8100
GCTTAACAC AGTTAGTTGT TGAAACTATT ACGACAATCT TATTTATTGT TAGTTTTTCG       8160
AGACTACCTA ACATCCCTCG AGTTAAGGCA AATTTAAAAA AAGAGACCTT CAAAATCATT      8220
GTGTCACTTG TTATGGCATT GACGGTGGTA TCACTTATTT TTGTTGCTCA ACAAGCAGAT      8280
GGTATGCCTT CAATTGCTAA ATTTATGAA GATGCATATG AACTTACAGG TGGAAAAAAT       8340
ATTGTCAATG CTATACTAGG TGACTTCAGA GCTTTAGATA CTATGTTTGA AGGACTAGTG      8400
TTAATCATAG CTGGATTAGG TATTTATACG TTACTTAATT ACAAAGATAG GAGGGGGCAA     8460
```

| | | | | | |
|---|---|---|---|---|---|
| GATGAAAGAG | AATGATGTAG | TACTTAAATC | AGTTACAAAA | ATTGTAGTGT | TTATTTTGTT | 8520
| AACATTTGGA | TTTTATGTAT | TTTTTGCTGG | CCATAATAAT | CCAGGTGGTG | GCTTTATTGG | 8580
| TGGCTTGATT | TTTAGCTCGG | CATTTATCTT | AATGTTTCTT | GCCTTTGATG | TAAATGAAGT | 8640
| GTTGAAAAAA | GCTT | | | | | 8654

( 2 ) INFORMATION FOR SEQ ID NO:7:

( i ) SEQUENCE CHARACTERISTICS:
        ( A ) LENGTH: 5024 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 32

( x i ) SEQUENCE DESCRIPTION: SEQ ID NO:7:

| | | | | | |
|---|---|---|---|---|---|
| AAGCTTTTTG | ATTTTTAAAG | AAAAAATTAA | ACAAGGGGGC | ATTGCTTATG | GTCAATAGAA | 60
| GAAAGATATC | AATTATTGGC | GCGGGACATA | CAGGTGGGAC | TCTAGCATTC | ATTCTTGCAC | 120
| AAAAGGAATT | AGGAGATATT | GTGTTGATTG | AACGCCAGCA | ATCAGAGGGT | ATGGCTAAAG | 180
| GAAAGGCGTT | AGATATTTA | GAAAGCGGAC | CCATTTGGGG | GTTTGACACA | TCTGTACATG | 240
| GTTCAGTAAA | TATAGAAGAT | ATTAAAGATT | CAGACATAGT | GGTGATGACT | GCAGGTATAC | 300
| CTAGGAAATC | AGGAATGACA | AGGAGAAGAA | TTAGTTCAAA | CTAATGAACA | AATAGTACGA | 360
| GAAACTGCAT | TACAAATTGC | AACGTATGCA | CCTCATTCAA | TAATTATTGT | ATTGACTAAT | 420
| CCGGTTGATG | TTATGACATA | TACTGCATTT | AAAGCATCAG | GTTTCCTAA | AGAACGTATT | 480
| ATTGGTCAAT | CTGGAATTTT | AGACGCTGCA | AGATATCGAA | CTTTATTGC | TCAAGAACTT | 540
| AACGTGTCTG | TCAAAGATGT | AAATGGGTTT | GTTTAGGTG | GACATGGTGA | TACGATGTTA | 600
| CCTTTGATTA | ATAACACACA | CATTAATGGG | ATTCCAGTTA | AGCATCTTAT | TTCTGAAGAA | 660
| AAGATTGATC | AAATTGTTGA | ACGTACACGT | AAGGGTGGTG | CAGAAATTGT | TGCATTACTA | 720
| GGTCAAGGCT | CAGCATATTA | TGCACCAGCA | ACTGCTATAT | ATGAAACTAT | AGATGCAATT | 780
| TTTAATGATC | GGAAACGGTT | ATTACCAAGT | ATTGCTTATC | TAGAGGGAGA | ATACGGTTGT | 840
| TCAGATATTT | GTTTCGGAGT | TCCTACTATA | ATAGGATATC | AAGGAATAGA | AAAGATTATA | 900
| GAGGTAGATA | TGAATAATGA | TGAGTATCAA | CAACTACAAC | ACTCTGCGCA | AGATGTGAGT | 960
| GAAGTCAAAA | ACTCACTAAA | ATTCAAATAA | ATAATTATGA | AGTTCTACAT | CTTAAATTGT | 1020
| TAGATTTTG | TGAAAATTGT | GTAAAGGGTA | TTTTTTCGTT | GATTATAAA | AGCGCTTTCT | 1080
| TGATATAATG | AACATATATT | CATAGAATAA | GGAGACGATT | AAAATGGCTA | AAGGGGACCA | 1140
| ATATCAAGCT | CATACTGAAA | AATATCATGA | GTAAAAAGTC | TAAAAAAAGT | TATAAACCTG | 1200
| TGTGGATTAT | CATTAGTTTT | ATTATTTAA | TTACAATCTT | GTTATTACCC | ACACCAGCAG | 1260
| GATTACCTGT | AATGGCTAAA | GCAGCACTAG | CTATTTAGC | TTTCGCTGTA | GTTATGTGGG | 1320
| TTACAGAAGC | AGTTACTTAT | CCAGTTTCTG | CAACATTAAT | TTTAGGATTA | ATGATACTTT | 1380
| TACTAGGTTT | AAGTCCAGTT | CAAGATTTAT | CCGAAAAACT | TGGAAACCTA | AAAGTGGCGA | 1440
| CATAATACTA | AAAGGTAGCG | ATATTTTAGG | AACGAATAAC | GCGCTTAGTC | ACGCTTTTAG | 1500
| TGGTTTTTCA | ACCTCAGCCG | TAGCACTTGT | AGCTGCAGCA | TTATTTTAG | CAGTAGCTAT | 1560
| GCAGGAAACC | AATTTACATA | AACGACTTGC | ATTATTTGTG | CTATCAATTG | TTGGAAATAA | 1620

```
AACTAGAAAT ATAGTCATTG GTGCTATTTT AGTATCTATT GTTCTAGCAT TCTTTGTACC    1680
ATCAGCTACA GCACGTGCTG GTGCAGTTGT CCCAATATTA CTGGGAATGA TTGCTGCATT    1740
TAATGTGAGT AAGGATAGTA GACTTGCTTC ATTATTAATT ATTACTGCTG TACAAGCAGT    1800
TTCGATATGG AATATAGGTA TTAAAAACGG CTGCAGCACA AAATATTGTA GCCATCAATT    1860
TTATTAACCA AAATTTAGGA CATGATGTAT CATGGGGAGA GTGGTTTTTA TATCTGCGCC    1920
GTGGTCAATC ATTATGTCTA TAGCTCTTTA TTTTATAATG ATTAAGTTTA TGCCACCTGA    1980
ACATGATGCA ATTGAAGGTG GAAAAGAGTT AATTAAAAAG GAACTTAATA AATTAGGACC    2040
AGTCAGTCAT AGAGAATGGC GACTAATTGT GATTTCAGTG CTTTTATATT CTCTGGTCGA    2100
CTGAGAAAGT ATTGCATCCG ATTGATTCAG CTTCGATTAC ACTAGTTGCT CTAGGTATTA    2160
TGCTAATGCC AAAGATTGGT GTTATTACTT GGAAAGGTGT TGAAAGAAG ATTCCTTGGG    2220
GGACGATTAT AGTATTTGGT GTAGGAATCT CACTTGGTAA TGTATTACTT AAAACAGGAG    2280
CCGCTCATGG TTAGTGATCA ACATTTGTTT GATGGGTCTT AAACATTTAC CGATCATAGC    2340
AACTATTGCG TTAATTACCT TATTTAATAT ATTAATACAT TTAGGTTTTG CAAGTGCAAC    2400
GAGCTTAGCC TCTGCGTTAA TACCTGTGTT TATTTCTTTG ACTTCAACGC TAAATTTAGG    2460
TGATCATGCT ATTGGTTTTG TATTAATACA ACAATTGTTG ATTAGTTTTG GTTCCTACT    2520
ACCTGTCAGT GCACCACAAA ATATGCTTGC ATATGGTACT GGGACTTTTA CCGTAAAGGA    2580
TTTTTTAAAG ACAGGTATAC CTTTAACGAT AGTAGGTTAT ATTTTAGTTA TCGTATTTAG    2640
TTTAACGTAT TGGAAATGGC TTGGTTTAGT GTAAGTAAAA GATTAGGTA TTAAAATGAT    2700
AATTATAAAT GTCTCGTAAA GTTTAATATT TTAACTTTAC GACACATTTT TTATAAACTC    2760
GTGGCAAGTT AATCTTAATA GTTGAAATGT ATCGTATAAA AAATATATGA ATGTAAATAG    2820
AATTTAGTAT TAGAGAATAA CAAAAAATTG ATGTTAGGTG GTAAAATCTA ATGGCTATAG    2880
GTGTCATATT AAATAGAGTT TTTAGGCTAA ATAATAATCC ATTATTTGAT TATATATATA    2940
GTAATAAAGA ATCTATAAAT CATTGTTATT TTATTATTCC AACTGAAGAG TTTGAAGAAG    3000
AAGCAAAAAA GAAAGCACAA TACTATTATG GGTCCATACA GAAGTTTATG TATGAACTAC    3060
AACGATATGA TATAGAACCC TTTTTGATGT CTTATGATAA ATTAATAGAC TTTTGTAAAA    3120
AACAAGCTAT AGACAAAGTT GTTGTTGCAG GTGATATTAT GAGTTATCAT CACGAAGAAT    3180
ATGACATTTT ACATCAAAGG AAACGATTTA AACAAGCTAA TATTCAAGTA ATATCATTAA    3240
GAGCAAATCA TTATTTTAAC CCCCGCAAAA CACATAATAA ACAAGGGGAA CCATATAAAG    3300
TATTTACCAG TTTTTATAGA AAATGGCGTC CTTACTTAAT GATTAGAGAT GAATATGACT    3360
ATCATTTAGA AGATATTTCA AAGGTTGTAG TGAAATCTCA ACATAAAATT AAAGAAGATT    3420
ATCATTCATA TGGTATAAGT GAACGTGATG TTCAAAATCG TTGGTCTGAA TTTTTATCTC    3480
AAGATATCGA AAATTATAAA GAAACAGGG AATACTTGCC TGAAGTATTA ACAAGCCAAC    3540
TAAGTATTTA CTTAGCTTAT GGAATGATAG ATATTATACA ATGTTTTCAA CGATTTACTT    3600
CAAAATTATG ATAAAAATGA ACAAAATTAC GAAACTTTTA TACGTGAATT GATTTTTAGA    3660
GAGTTTTATT ATGTATTAAT GACCAATTAT CCCGAAACAG CTCATGTTGC TTTTAAAGAA    3720
AAATACCAAC AATTGAAATG GTCTTATAAT GAAGAGAATT TAAACTGTG GAAAGATGGG    3780
AATACTGGTT TTCCAATTAT TGATGCAGCA ATGGAGGAAC TTAAAACAAC TGGATTTATG    3840
CATAATCGCA TGAGAATGGT AGTTTCTCAA TTTTTAACTA AGATTTGTT TATTGACTGG    3900
ATTTGGGGTG AGTCATTTTT CAAACAAAAA TTAATAGATT ATGATGCAGC TTCAAATGTT    3960
CACGGATGGC AGTGGTCAGC TTCTACTGGA ACAGATGCTG TACCATACTT TAGAATGTTT    4020
```

-continued

| | | | | | |
|---|---|---|---|---|---|
|AATCCTATAA|GACAAAGCGA|GCGTTTTGAT|AATAATGCAC|GATATATAAA|AACTTACATT 4080|
|CCAAGATTAA|ATCAGGTAGA|TGCTAAGTAT|TTACACGATA|CTCATAAATT|CGAGCAACAA 4140|
|ATAAAGGGGC|AAGGTGTTGA|AATAGGTAAA|GACTATCCTA|AACAAATGAT|TGATCACAAA 4200|
|GAAAGTAGAC|AACGTGTAAT|GTCAGAATTC|AAAGCTATAG|ATTAAATAAA|AAAGATCTGA 4260|
|ACAACATGAT|ATAGGTGTTC|AGATCTTTAT|CTAGTTACAT|AAAAAAGCAA|ACATGAATTA 4320|
|AAATATATTC|TAACAAAGTT|AAAATATACA|TATATTTAAG|ATTTAATTTA|GTTTTCAAAG 4380|
|GTACTTCCCA|ATTTGTATAA|CGGGGCTCAT|AATAAAATAA|TTGCATCAAA|TATAATCCTA 4440|
|TCCCTAACGG|TAAACACATT|AATAAAATAG|CTTTAGTATA|ACTCCATCCT|ATTTGATGCC 4500|
|ATAAATGACC|TATCATAAGT|TGAATAATGA|TGAGACATAC|CATTAAAATT|ACTTCAATTA 4560|
|TCATTGGTAT|AATCTCACCC|CTTTAATAAA|CAATATGACT|GTTGCTTGTA|TGAGCACCAT 4620|
|TAAAACGACA|AATAGTAACG|CTTTAACATC|TATGATTAAA|AAAACCTCTT|TCACAATTTT 4680|
|TAAAGGTGCA|TTTAATAAAT|AGACAGTATG|TAATCTTAAG|AATCGACCGA|TGTAAATACC 4740|
|TAATCCATTT|AAGAACATTA|ATATAACTAT|CAATAGTCGA|TTTAACCATA|CATAAGACGT 4800|
|AAAATGTGCA|ATTTCTAAAA|ATATAAGAAT|TGTGAGGTAT|ATTGCTAAGA|GTACGCCAAG 4860|
|TATTAAATAG|GTGAAATAAA|TCCATTCTGT|GATGTTTAAT|CCAGCTAAAA|AGTTAAATTG 4920|
|AAATTGGTTT|AAGTGTATGA|GATCGGTAAT|CATATAAAAT|GTGTTTGGAA|CTAATAATAG 4980|
|AAATATGAGT|CCGAAAACAA|TAAATAAGGG|CCATTCAAAA|GCTT| 5024|

( 2 ) INFORMATION FOR SEQ ID NO:8:

( i ) SEQUENCE CHARACTERISTICS:
        ( A ) LENGTH: 3287 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 37

( x i ) SEQUENCE DESCRIPTION: SEQ ID NO:8:

| | | | | | |
|---|---|---|---|---|---|
|AAGCTTGCCT|ATTGATTTTA|AAAAATTAAT|GATTATAGGT|TCACTCATAT|CTGTTGCAAC 60|
|TGCATCAGTG|CCTATGTTTT|TTGGGAAGCC|ATTTTTATAT|CAAACTGAAG|CAAATGTAAC 120|
|ATTTCCATTA|CTAGGACATG|TTCATGTTAC|TACTGTGACT|TTATTTGAGC|TTGGCATCTT 180|
|ATTAACAGTA|GTAGGTGTGA|TTGTTACAGT|TATGCTATCT|ATAAGTGGGG|GTAGATCATG 240|
|AATTTAATAT|TACTCCTTGT|GATAGGATTT|TTAGTGTTTA|TTGGAACTTA|TATGATTTTA 300|
|TCTATTAATT|TAATTCGTAT|TGTTATTGGT|ATTTCTATTT|ATACACACGC|CGGTAATTTA 360|
|ATTATTATGA|GTATGGGGAA|ATATGGACCT|CATATGTCTG|AACCGCTAAT|TCAAGGTCAT 420|
|GCTCAAAACT|TTTGTTGATC|CTTTATTACA|AGCTATCGTT|TTAACAGCTA|TTGTGATTGG 480|
|ATTTGGTATG|ACTGCGTTTT|TATTGGTGTT|AATATATAGA|ACTTACAGAG|TAACTAAAGA 540|
|GGATGAAATA|AGTGCATTGA|AAGGTGATGA|AGATGATGAG|TAATTTAATA|ATATTGCCTA 600|
|TGTTGTTGCC|TTTTGTATGT|GCTTTAATTT|TAGTCTTCAC|TAAAAATAAA|AATCGTATTT 660|
|CGAAAATCCT|ATCCATTACA|ACTATGATTG|TTAATACAAT|GATTTCAATT|GCTTTACTTA 720|
|TTTATGTCGT|TAATCATAAA|CCGATAACAC|TTGATTTTTG|GGGGGATGGA|AAGCACCTTT 780|
|CGGCATTCAA|TTTCTAGGTG|ATTCACTGAG|TCTGCTTATG|GTGTCAGTAT|CATCTTTTGT 840|
|TGTTACGCTA|ATAATGGCAT|ACGGCTTTGG|TAGAGGGGAG|AAGCGAGTCA|ATCGATTCAC 900|

```
CTCCTACATT ATCTTTATTA ACAGTAGGTG TTATTGGTTC GTTTTAACT  TCTGATTTAT    960
TTAACCTATA CGTGATGTTT GAAATTATGC TTCTTGCTTC GTTTGTACTT GTTACATTAG   1020
GACAATCTGT TGAACAATTA CGTGCAGCGA TAGTATATGT TGTTCTGAAT ATTTTAGGTT   1080
CGTGGTTGCT TTTATTAGGA ATTGGCATGT TATATAAGAC AGTCGGAACA CTTAATTTCT   1140
CACATTAGC  GATGCGATTG AATCATATGG AAAATAACCA AACAATAACG ATGATATCTT   1200
TAGTATTTCT AGTTGCTTTT AGTTCAAAGG CAGCACTAGT GATTTCATG  TGGTTACCTA   1260
AAGCATATGC AGTGCTTAAT ACGGAACTTG CCGCGTTATT TGCAGCATTG ATGACAAAAG   1320
TTGGAGCTTA TRCGCTTATT CGTTTTTTA  CTTTACTATT CGACCATCAT CCAAGCGTCA   1380
CGCATACATT GCTCGTGTTT ATGGCTTGTA TCACAATGAT TATCGGTGCA TTTGGTGTCA   1440
TCGCTTACAA AGATATTAAG AAAATTGCGG CTTATCAAGT TATTTGTCT  ATTGGATTCA   1500
TTATTTTAGG TTTAGGTTCT CATACTATAT CAGGTGTAAA TGGTGCTATC TTCTATTTAG   1560
CGAATGATAT TATCGTTAAG ACATTATTGT TTTTGTAAT  TGGTAGTCTT GTTTATATGT   1620
CAGGCTATCG AAATTATCAG TATTTAAGTG GACTGGCAAA AGAGAACCAT TCTTTGGTGT   1680
TGCATTTGTC GTGGTAATTT TTGCTATAGG TGGCGTACCT CCTTTTAGTG GCTTTCCGGG   1740
TAAAGTCTTA ATATTCCAAG GGGCTATTAC AAATGGTAAT TATATTGGTT TAGCACTTAT   1800
GATTGTGACA AGTTTAATTG CTATGTATAG TCTTTTTAGA GTGATGTTTA TAATGTATTT   1860
TGGTGATGCT GACGGAGAAC AAGTACAATT TAGACCACTA CCTATTTATC GTAAAGGTTT   1920
ACTTAGTGTT TTAGTTGTAG TGGTATTAGC GATGGGTATT GCAGCCCCTG TTGTTCTGAA   1980
AGTAACAGAG GATGCAACAA ATCTTAATAT GAAAGAAGAT GTCTTCAAA  AGAATGTAAA   2040
TACACATTTG AAGGAGGTTA ATCATAAGTG AAGCAAGTTG TATTAAATAT TGTTATCGCG   2100
TTCCTTTGGG TACCCTTTCA AGATGAAGAT GAATTTAAAT TTACAACCTT CTTTGCTGGA   2160
TTTTTAATTG GTTAATTGT  GATTATATT  CTGCATCGCT TTTTTGGTGA AGAATTTTAT   2220
TTGAAAAAGA TATGGGTGGC TATTAAATTT TTAGCTGTAT ACCTATACCA GCTTATTACT   2280
TCTAGTATAA GTACCATAAA TTACATCTTA TTTAAGACGA ATGAAGTTAA TCCAGGTTTA   2340
CTCACATATG AAACTTCATT AAAAAGTAAT TGGGCTATTA CTTTTTTAAC GATTTTAATT   2400
ATTATTACTC CAGGATCGAC AGTTATTCGA ATTTCTAAAA ATACTAATAA ATTTTTTATT   2460
CACAGTATTG ATGTGTCAGA AAAAGATAAA GAAAATCTTC TAAAAAGTAT TAAGCAGTAT   2520
GAGGATTTAA TTTTGGAGGT GACACGATGA TTGAAATGTT CACTCAAATA TTTATTATAA   2580
GTGCATTAGT GATTTTTGGT ATGGCACTAC TTGTTTGTCT AGTCAGATTA ATTAAAGGTC   2640
CCACTACTGC TGATAGAGTT GTATCATTTG ATGCCTCGAG TGCTGTTGTT ATGTCTATTG   2700
TTGGTGTGAT GAGCGTTATT TTTAACTCAG TGTCTTAATG TTAATTGCAA TTATTTCGTT   2760
TGTCAGTTCG GTCTCAATTT CAAGATTCAT CGGGGAAGGA CGTGTCTTCA ATGGAAATCA   2820
TAAAAGACAT CGTTAGTCTT ATTGCTTCGA TACTTATTTT CTTAGGAAGT ATTATTGCAT   2880
TAATTAGTGC AATAGGGATT GTAAAATTTC AAGATGTCTT TCTAAGAAGT CACGCCTCAA   2940
CGAAAAGTTC TACATTGTCA GTATTACTAA CTGTAGTTGG TGTACTGATC TATTTTATTG   3000
TGAATTCAGG TTTTTTCAGT GTCAGATTAT TATTATCACT AGTTTTATC  AATCTTACAT   3060
CTCCGGTTGG AATGCATTTG ATAAGTAGAG CGGCCTACCG TAATGGTGCA TATATGTACA   3120
GGAAAGACGA TGCATCTAGA CAATCTACTA TCTTATTAAG CCAAAAAGAG TTTAATACGC   3180
CAGAAGAATT AAAAAAACGT GCAAAACTAC GAGAAGAAAG ACGAGAAAAA TTATACTATA   3240
AAGAAAAAGA ATATATTAAT AAAATGGACG ATTGATTGTT TAAGCTT                3287
```

( 2 ) INFORMATION FOR SEQ ID NO:9:

( i ) SEQUENCE CHARACTERISTICS:
        ( A ) LENGTH: 2291 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus faecalis
        ( B ) STRAIN: Clinical Isolate S2-1

( x i ) SEQUENCE DESCRIPTION: SEQ ID NO:9:

```
AAGCTTTAGA  TAATGATAAA  CGCGTGTATG  TGAATGTCCA  GCCGATTCAA  TCGCCTACTG    60
GAGAAACAGT  GATTGGTGTC  CTTTATGTGA  AAAGTAATTT  AGAAAATAAA  TACCAAGAAA   120
TTACTAACAC  AGCAAGTATC  TTTTTCACTG  CTTCTATTAT  TGCCGCAGCA  ATCTCGATTA   180
TTGTGACCCT  ACTGATTGCA  CGATCAATCA  CGAAGCCGAT  TGGTGAAATG  CGCGAGCAAG   240
CCATTCGAAT  CGCTCGTGGT  GATTACGCTG  GAAAAGTAGA  AGTCCATGGA  AAAGATGAAT   300
TAGGCCAATT  AGCAGAAACA  TTTAATCAAT  TATCAGAACG  GATTGAAGAA  GCACAAGAAA   360
CAATGGAAGC  AGAAGAATCG  TTTAGATAGT  GTCTTAACGC  ATATGACAGA  TGGTGTCATT   420
GCGACGGATC  GCCGCGGAAA  GGTGATTACG  ATTAATGAGA  TGGCCCTTTC  ATTATTAAAT   480
GTAAAAAATG  AAAATGTGAT  TGGGACCTCG  TTATTAGAGT  TGTTAGATAT  TGAAGAAGAT   540
TACACATTGC  GGAAGCTGTT  AGAAGAGCCA  GATGAACTGC  TGATTGATCG  CTCAACGTCT   600
GATCGTGAAG  AAGACCAAAT  GATTATCCGG  GTAGACTTTA  CGATGATTCG  TCGGGAATCA   660
GGATTTATTA  CTGGCTTAGT  TTGCGTACTT  CATGACGTCA  CAGAACAGGA  AAAAAACGAA   720
CGGGAAAGAC  GGGAATTTGT  TTCCAATGTT  TCTCATGAGT  TGCGACGCCT  TTGACAAGTA   780
TGCGTAGTTA  TATAGAGGCT  TTGAGTGAAG  GAGCTTGGGA  AAACCCTGAG  ATTGCGCCGA   840
ATTTCTTAAA  AGTCACGTTA  GAAGAAACCG  ACCGGATGAT  TCGTATGATT  AATGATTTGT   900
TAAATTTATC  TCGGATGGAC  TCTGGGAATA  CACATCTTCA  ATTAGAGTAT  GTGAATTTTA   960
ACGAATTGAT  TAATTTTGTC  TTGGATCGCT  TTGATATGAT  GATTGAAAAT  GAGCAAAAAA  1020
ATTACAAAAT  TCGCCGTGAA  TTTACTAAAC  GCGATTTATG  GGTAGAGTTA  GATACAGACA  1080
AAGTAATTCA  GGTTTTTGAC  AACATTTTGA  ACAATGCGAT  TAAGTATTCG  CCAGATGGCG  1140
GCGTCATTAC  CTGCCGACTA  GTTGAAACAC  ATAATAATGT  CGTCTTTAGT  ATCTCGGACC  1200
AAGGTTTGGG  CATCCCTAAA  AAAGATCTCG  GGAAAGTCTT  CGAGCGTTTT  TATCGTGTGG  1260
ATAAAGCACG  TGCGCGAGCA  CAAGGTGGGA  CTGGTTTAGG  TTTAGCAATT  TCTAAAGAAG  1320
TAATTCGGGC  CCATAACGGG  AGTATTTGGG  TGGAAAGTAC  AGAAGGTGAA  GGATCAACTT  1380
TCTATATTTC  ACTACCATAT  GAACCTTATG  AAGAGGATTG  GTGGGAATGA  TGAAAAAATC  1440
AGAATGGATT  ACAAGAATTG  GCTTGATTTT  GATGGTCATT  TTAAGTATAT  ATTTTTCAGT  1500
CAATATCTGG  CTGAATTCTG  CCAAAAAAAT  ACCAGAAATG  AAGTCGGGAA  GCCAAGTCAC  1560
AACAGCTGTC  AATGAAAAAG  CCATTGGCGA  TGTCTATTTA  CCTTTGCAAT  TGATTCGAAT  1620
AGCCGATGGA  AAAGCGATGC  AAAGTAATCG  TGAAACATTA  ATTAGTAATG  TTCAAAATGA  1680
TATTAAAATG  GCTACGTTTG  GTAAATTGAC  ACAAGTTGTG  ACAAAAAATG  CAGAGCAACT  1740
TAAGCGCTAC  AACCAAATGG  AACAAGGCAT  TGAACTTCTT  TATCAAGGTC  CCTTTTTAAT  1800
CTCGGACTAT  GCTTCGATTT  ATAATCTATC  CATTAATTTT  ACTAACTTTA  ATGAGTTGAC  1860
```

| | | | | | |
|---|---|---|---|---|---|
| GGACCAGTAT | TTTACGAAAA | TTCAATTGGA | TTTTAACGAA | AATAAGATAC | GTTTTTTAGA | 1920
| TTATGATCAA | TCCAACGTCT | ATGAAGCGCC | CATGACTGTT | AATAAGGCGC | GCTTAATGGG | 1980
| AATTATCAAT | AAAGAGGGAT | TGCAATATCA | AGACGTTTCC | GAAAATACGC | TAACCAAACA | 2040
| AGGACAATGT | TATTTAACCA | ATGATATGAA | GTTGAAAAAG | TACAGTTATA | TCTTANTTCG | 2100
| CAACCAGTTA | CTCGTTTTAG | GAATGCTTTT | TTCAATGAAA | CGGAAGATAT | CCAAACCAAT | 2160
| GAAGACAGTC | AAGACTTAAC | CTATACGAGT | AAAGAAGAAC | GATTGTTTGC | AGAAGAAAAA | 2220
| CTGGGGAAAA | TCGATTTTAA | AGGGACCTTG | CCAGAAGAGA | ATAAACGGGA | CTCAATCTAT | 2280
| AATCAAAGCT | T | | | | | 2291

(2) INFORMATION FOR SEQ ID NO:10:

(i) SEQUENCE CHARACTERISTICS:
      (A) LENGTH: 3719 base pairs
      (B) TYPE: nucleic acid
      (C) STRANDEDNESS: double
      (D) TOPOLOGY: linear (ii) MOLECULE TYPE: Genomic DNA (vi) ORIGINAL SOURCE:
      (A) ORGANISM: Enterococcus faecalis
      (B) STRAIN: Clinical Isolate S2-3

(xi) SEQUENCE DESCRIPTION: SEQ ID NO:10:

| | | | | | |
|---|---|---|---|---|---|
| AAGCTTCATT | AGAGCGTCAA | CTGTTTTTGG | TGTTGGGTTC | ACAATGTCAA | TTAGACGTTT | 60
| GTGAGTACGC | ATTTCGAATT | GTTCGCGAGA | ATCTTTGTAT | TTATGAGTCG | CACGAATAAC | 120
| TGTGTAAAGT | GAGCGTTCTG | TTGGTAATGG | AATCGGACCT | GATACGTCAG | CTCCAGTTCT | 180
| TTTTGCTGTT | TCCACAATTT | TATCCGCTGA | TTGATCTAAA | ATACGGTGTT | CATACGCTTT | 240
| TAAACGGATA | CGAATTTTTT | GTTTTGCCAT | CTTGTTCCCT | CCTTCGCCTA | TTTTAAAAGT | 300
| AGACATAGCT | CCACGAAAAT | TTATCCGGCA | TGCTCGTTCA | TGGCAAAGCG | TCCGAGCGTG | 360
| TCGCAACCTC | TCGCTTCACA | GCCGGCAAAT | CAAATCGTTG | ATCTACCAAT | GCTTTTTACA | 420
| CTCCTGTAAA | CAGCACCTTT | TTGATTATAC | TATGAAAGGA | TAGTGTTAGC | AAGGATTTTC | 480
| TGCGTTTTTT | TAAAAGAATT | TTTTCTTGTT | TTGAAAAGCA | TTTGTTTTGT | TTTTCAATTC | 540
| TTTTCATTCT | ATTTTTATAA | AAAAAGAATT | TGAGATTCTT | TTTTTACCAG | AATCTCAAAT | 600
| TCTTTCTTTT | TTATTCTATT | AACCAATCCG | GCGCATTGGA | ATATCATTGT | TATCTGGATG | 660
| AACCAATAAA | TATTGAATAA | CATCAATATT | GCTTGCTTGG | AATGAGGCTG | CACATGCTTG | 720
| CAAATATAAG | TCCCACATTC | GATAGAAGCG | CTCGCCTTTT | TCGTCAACAA | TTTCTGTTTC | 780
| TATATTATGG | AAGTTTTTG | TCCAATGTTC | CAACGTCAAT | TGATAATCTC | TGCGCAAACT | 840
| TTCCAAGTCA | ATCACTTGCA | AGTCGTTTTC | TGTCATATGG | CCGACTAGCT | CAGTGACACC | 900
| AGGAATATAG | CCACCTGGGA | AAATATAACG | ATTAATCCAA | GCATTTTAG | CCCCACCTTG | 960
| TTGGCGACTG | ATCCCATGAA | TCAACGCCGT | ACCTTTAGGC | GCTAAATTTC | GCTGAACGAC | 1020
| ATCAAAATAT | TCATGTAGAT | TTTCCGCACC | GACATGTTCA | AACATCCCAA | CACTCGTAAT | 1080
| ATGGTCAAAA | GACTCTCCTT | TTAAATCACG | ATAATCCATC | AATTTGACAG | TCATTCGATC | 1140
| TTGTAGACCT | TCTTTTTCTA | TAATATGGCG | AATATGATGA | AATTGCTCTT | CACTTAATGT | 1200
| AATCCCAGTT | GCTTGGCTC | CATATTCTTT | CACCGCAGTT | AAAATTAACG | TGCCCCAGCC | 1260
| GCAGCCAATA | TCCAGTAAAG | TGTCGCCCTC | TTTGATAAAC | AATTTATCTA | AAATATGATG | 1320
| AACTTTATTC | ACTTGCGCTT | GTTCTAATGT | ATCTTCAGGC | GTTTTAAAAT | AAGCACATGA | 1380
| ATACGTCATT | GTTTGGTCAA | GCCATTTTTT | GTAAAAATCA | TTTCCTAGAT | CGTAATGGCT | 1440

```
GTGAATATCC  TCTTGCGAAC  GTTTTTTGA   ATGACTTTCT  TTAGGAAGCC  ATTTAATAAA   1500
TTTAGCATTG  TGTAAAAAGC  TATCCTTTTG  GTTATACACA  TCATAAATCA  GCGCTTGGAT   1560
ATCGCCTTCG  ATTTCAATTT  TGCGATCCAT  GTAGGCTTCC  CCTAAAGTTA  ACGAAGCGTT   1620
ATTCAGTAAA  TCCTTCACAG  GAATTTTTC   ATTGAATACA  ATTTAAAAA   CCGGATCCCC   1680
CGACCCTTGC  CCATACTCTT  TGACGGTACC  ATCCCAGTAT  GTGACTTGTG  TCTTTTTTGA   1740
AAAAGACCAT  TTAAACAGTT  GACTGTACGT  TTCTTTTTCT  AACATTGCAT  TCCCTCCATT   1800
AAATACCATT  TGAAGCCAAA  ACAAAAGAA   GTCGCTTTCC  GGTAGTTCGT  CAAAACAAAC   1860
ACCACAGTCC  GTTCTAAACT  GAAGCACAGA  AAAGTTATCA  CCCCTTCTAT  GTTCCGCTTC   1920
TTTTTTGCAA  TTACAGTTCT  ATTCTACTCC  TCTTTTAAAA  ATTTGAACAT  TCTTTTAACG   1980
TAATACCTAC  TATTGTTATT  CTTTATCACA  AAAAAACTAG  AGCCAGTCCT  TGACAGACTC   2040
CTCTAGTTCT  AAATATTATG  CTTTCTTACG  CATCCGTTGT  TCCGCATGAG  TGTAAGCGCC   2100
ATGCCACACG  TGCCCCACAT  AAGGATTAAC  TTGAATACCG  TGTTAATCG   CCGCTGCTAC   2160
AAATTTTTCG  CTAAAGTTAC  TGCTTCTAAC  ACCGAATAAC  CTTTCGCCAA  GCCAGCTGTG   2220
ATTGCCGCTG  AAAAAGTACA  ACCTGCACCA  TGATTATAAT  CAGTTGGATA  TAATTCATTT   2280
TCCAAAAGAT  GCGCGGTGTG  ACCATCGTAA  AATAAGTCCA  GTGCTTTTC   ACCAGCTAAG   2340
CGATGTCCCC  CTTTAACCAC  GACATGCTTG  GCTCCCATTT  GTACAATTCG  TTTTGCCGCT   2400
TCTTCCATCT  CCGCCACGGA  AGAAATTTCG  CCTAAACCAG  ATAAGATGCC  CGCTTCAATT   2460
AAATTAGGCG  TGGCAACTAA  TGCTAATGGC  AGTAAATCGT  TTTTAGGCCT  TCCACACTTT   2520
TGGGTTGCAG  AATTTGTGCC  GTTCCCTTAC  AAGCAATGAC  TGGGTCAATC  ACGACTTTTT   2580
GAATTTTTTC  TTGTTTAATG  TACTTACTAG  CCATTTAAT   ATTTGTTCA   TTACCCCATC   2640
ATCCCTGTT   TTCAAAGCCG  CTACTGGACC  GCCTGCAAAA  ACCGAAATCA  ATTGTTTTC    2700
TAAGAGCGTT  TCTGGCAATT  CAGTTACTTC  ATGTGACCAA  CCTGTCGTAG  GATCCATCGT   2760
CACAATCGAG  GTAAACTTG   AAAATCCAAA  AACTCCATAC  TCTTCAAATG  TTTTTAAATC   2820
TGCTTGAATC  CCTGCCCCTC  CAGTTGAATC  GGAGCCTGCA  ATCGTCAATA  CTTTTTCCAT   2880
TAAATCACCT  AACCTTTTTC  TCCAAGTATA  CGGAAGAAAC  AAGTCTGCTA  AAACAGCCAA   2940
TTGGCTTATT  TTTTAGCCAG  CCAATTTCTA  AACAAAAAA   AGACCAGAGA  ATAAATTCTC   3000
TGGTCTTACG  TCCGAATACC  CCAGTTTTTC  ACGCTGGTTA  AAGCTATAGT  TAAAAAGTTA   3060
ATTATTAAC   GATTTCAGTA  ACAACGCCTG  AACCTACAGT  ACGTCCGCCT  TCACGAATAG   3120
AGAAACGAGT  TCCGTCTTCG  ATAGCGATTG  GGTGAATTAA  TTCAACGTCC  ATAGCAACGT   3180
TATCACCAGG  CATTACCATT  TCAGTACCTT  CTGGCAATTC  TACAACACCA  GTAACGTCTG   3240
TTGTACGGAA  GTAGAATTGA  GGACGATAGT  TAGTGAAGAA  TGAGTGTGAC  GTCCGCCCTC   3300
TTCTTTTGAT  AATACGTATA  CTTCAGCTTT  GAATTTTGTG  TGTGGAGTGA  TTGTAGCTGG   3360
TTTAGCTAAT  ACTTGTCCAC  GTTCGATATC  TTCACGTGCA  ACACCACGTA  ATAAAGCACC   3420
GATGTTGTCG  CCTGCTTCAG  CGTAGTCTAA  TAATTTACGG  AACATTTCAA  CACCTGTAAC   3480
AGTTGTTTTA  GATGTTTCGT  CTTTAATACC  AACGATTTCA  ACTTCGTCAC  CAACGCGAAC   3540
TTCACCACGT  TCAACACGGC  CTGTAGCAAC  AGTACCACGT  CCAGTGATTG  AGAATACGTC   3600
TTCGACTGGC  ATCATGAATG  GTTTGTCAGT  ATCACGTTCT  GGAGTTGGGA  TATATTCGTC   3660
AACTGCAGCC  ATTAATTCTA  AGATTTTTTC  TTCATAAGAC  TCGTCGCCTT  CTAAAGCTT    3719
```

( 2 ) INFORMATION FOR SEQ ID NO:11:

( i ) SEQUENCE CHARACTERISTICS:
  ( A ) LENGTH: 3480 base pairs
  ( B ) TYPE: nucleic acid
  ( C ) STRANDEDNESS: double
  ( D ) TOPOLOGY: linear ( i i ) MOLECULE TYPE: Genomic DNA ( v i ) ORIGINAL SOURCE:
  ( A ) ORGANISM: Enterococcus faecalis
  ( B ) STRAIN: Clinical Isolate S2-7

( x i ) SEQUENCE DESCRIPTION: SEQ ID NO:11:

```
AAGCTTCTAG CGTTTCGGAT TGGCGCCTAT GATGCACCAG GAGAGCGACG AATCAATACC      60
AAAAATATGC CTACAGCAGG AGGACTTGCA ATCTACATTG CTTTTGCTAG TTCATGTTTA     120
TTGATTTTTC GTTCGATTAT CCCACAAGAT TATATTTGGC CGATTATTTT GGCTGGTGGA     180
ATGGTTGTTT TGACAGGCCT CATTGATGAT ATTAAAGAGA TTACTCCAAT GAAAAAAACA     240
ATCGGTATTT TGTTAGCAGC ATTAGTTATT TTATTTGTT GCTGGAATTC GGATAGATTT     300
TGTGACGTTG CCAGTTGTTG GAATGATTGA TTTGCGCTGG TTTAGTTTAC CACTAACTTT     360
ATTGTGGATT TTAGCGATTA CGAATGCAGT AAATTTAATT GATGGTTTGG ATGGTTTAGC     420
ATCAGGCGTA TCCATTATTG GATTAACCAC GATTGGTATT ACAGGGTATT TTTTCCTACA     480
TGCTAAAACG GTCTATATCC CAATTGTTAT TTTTATTTTA GTTGCGAGCA TTGCGGGATT     540
TTTCCCATAC AATTTTTATC CGGCTAAAAT ATTTCTAGGA GATACCGGGG CGTTATTCCT     600
CGGGTTTATG ATTGCAGTAA TGTCGTTACA GGGCTTGAAA AATGCTACGT TTATTACGGT     660
AATTACGCCA ATGGTGATTT TAGGTGTGCA ATTACGGATA CGGTTTATGC AATTATTCGA     720
CGGCTATTGA ACAAGAAGCC CATTCCTCA GCAGATAAAA TGCATTTACA TCACCGCTTG     780
TTATCTTTAG GTTTTACCCA TAAAGGGGCG GTCATGACTA TTTATGCATT AGCGTTAGTT     840
TTTTCCTTTG TCTCTTTATT GTTCAGCTAT TCAAGTACAG TAGCATCAAT TTTATTAATT     900
GTCTTTTGTT TAATTGGCTT AGAACTATTC ATTGAACTAA TCGGTCTAGT TGGCGAAGGG     960
CATCAACCGT TGATGTATTT GTTACGGATT TTAGGGAATC GTGAATATCG TCAGGAGCAA    1020
ATGAAAAAGC GACTTGGCAA GCATTCTAAG AGAAAGTAAA GAAATCTTTA GGTTGCTTTG    1080
CGAGAGCTAA ACCTATGATA TAATTCCATT AAACTTAAAA AAGTATATGT GTGAAACATA    1140
TGCTTTTTTT TTAAGACGAT GTTTCAGTAG TAAGGAGAAA TGAGCATGCA AGAAATGGTA    1200
ACAATCTCGA TTGTCACTTA TAATAGTCGT TACATTTTA ATGTACTAGA CCAATTAAAA    1260
GCCGAACTAG GTACTGATAG TATCTATGAT ATTCATATCT ATGACAATCA TTCTGAAACA    1320
GCGTATCTTG AAAAATTAAC AACATATGAA CCATTTATTA CTATCCATCG CGCTGAAGAA    1380
AATCAAGGGT TTGGTCATGG TCATAATCAA GTGTTATTCA ATGCTTCGAC AAAGTATGCA    1440
ATTATTTTTA TCCCGATGTG TTGGTTACTA AAGACGTGCT TGATCGTTAT TAGACGTATC    1500
AAATAGATAA GAACATTGCA GTCGGTAGCC CTAAAGTTGT TAAATGAAGA TGGCACGACG    1560
CAATATTTAG TTCGTCAAAA ATTAGATGTC TTCGATTATA TGTTACGTTT TATTCCCTTT    1620
CAATTTGTAA AGAAAATTTT TGATAAACGT TTGAGTATTT ATGAATGTCG CGATTTGTCG    1680
GATACAGAAA CAACGGATAT TAAAATGGGC TCAGGCTGTT TTATGTTGAT TGATCGTGAA    1740
AAATTCGTTG AAATTGGTGG GTTCGATGAA CGTTCTTCA TGTACTTTGA AGACAACGAT    1800
TTATGTTTAC GCTTTGGCAA AGCAGGCTAT CGGATTCTCT ATACGCCTTT TGAAACGGTT    1860
GTTCACATGT ATGAAAAGGG CGCCCATAAA AGTCGAAAAT TGTTTAAAAT CTTTATGCAA    1920
TCAATGGGGA AATTTTTTAA CAAATGGGGC TGGAGGTTCT TTAATGAGT CAAAGATTAG    1980
```

-continued

```
CGGTAGTCAT CGTCTTATAT CAAATGAAAA TGGCTGATAC GCCGAATTAT TTGTTATTAA    2040
AAGAAGTGGT AGACCACCCC CAATTGCACT TATTTATTTA TGACAACAGT CCACTTCCTC    2100
AAGAAGATGC ATTATTTTTA CAACCAAATG TTACTTATCG ACATAATCCT GATAATCCAG    2160
GACTAGCGAC CGCTTATAAT GAAGCGATTG CTTTTAGTCA AGCGAATCAA TGTGAATTAT    2220
TGTTGCTCCT TGACCAAGAC ACAGAAGTGC CAGCCTCTTA TTTTGATACG TTGATCATCA    2280
TGCCATTAGA TCCGACTGTG GCAGTCTATG TTCCAATTGT AGAAGCAAAT GGACAACAAA    2340
TTTCGCCAGT ATATAGTGAT CAATACGTTG GGCTTAAAGG AGCAAAGCCA ACAGCAGGGA    2400
TAGCCAACCA ACCGTTGATG GCTATCAATT CTGGTACAGT TATTACGGCA GAAACGCTAC    2460
GCTGGTTGGA AGGATTTTCG GAAGAATTTC CTTGGACTA TTTAGACCAT TGGTTCTTTT    2520
ATCAATTAAA TCAAGCCAAT AAAAGATTG AAGTCTTACC AATCCACCTA AAACAAGAAT    2580
TGTCTGTTTT AGATTATCGT ACAATGAGTC CTCAACGTTA TCGCTCTATT ATTGAAGCAG    2640
AAACGTTATT TTATCGTCGA TATGATCAAG AAAAGTTTTC CCATCATCGA CGCCATTTAT    2700
TTTTACGCAG TAGTAAGCAA TTTTTAACTG TCAAAAATCG CCAAATTTGG CGGCAAACAT    2760
TGGCAGAATT TCTCAAGTTA ATGAAAGGAT AATCTATGAT CTCAGTTTGT ATTGCGACAT    2820
ATAATGGAGA AAAATATCTC GCGGAACAAT AGATAGTAT TCTTTTACAA GTCAGTGAAG    2880
AAGATGAACT AATTATTTCA GATGATGGTT CTACTGATCA TACGTTGGAA ATTTTGAGGA    2940
CGTATGCAGC GAATTATCCC CAAATTCAAT TGTTACAAGG TCCCAGGGCA AGGAGTGATT    3000
GCTAATTTTG CATTTTGCCT TACGCATACG AAAGGCGAAG TAATATTTTT AGCAGATCAA    3060
GATGATGTTT GGTTGCCAAA TAAAGTAACG ACGGTGACAG AATATTTGA AGCGCACCCT    3120
GACATCCAAG TGGTTATTAG TGACTTGAAA ATTGTTGATG CGGATTTACA AGTTACCAAT    3180
CCCTCTTATT TAAGTTTCGA AAAGTCAAAC CAGGGTTTTG GCGAAATGCG ATAAAAAGTG    3240
GCTATATTGG GGCAGGTATG GCCTTTCGTC AAGAAATGAA AAACGTCATT TTACCCATTC    3300
CGCCAGAAGT TCCTATGCAT GATATGTGGA TTGGCTTATT AGCTGCACGG AAGAAGCAAA    3360
CGGGTCTCAT TAAAGAACCA TTAGTGCTTT ACCGAAGACA TGGAGCGAAT GTCAGCCCCA    3420
TTATTACCAA AACAAGTTTC CAACAAAAAT TAAATTGGCG TGTGAATTTA TTAAAAGCTT    3480
```

(2) INFORMATION FOR SEQ ID NO:12:

(i) SEQUENCE CHARACTERISTICS:
        (A) LENGTH: 2441 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Enterococcus faecalis
        (B) STRAIN: Clinical Isolate S2-27

(xi) SEQUENCE DESCRIPTION: SEQ ID NO:12:

```
AAGCTTCTGC GCTAGGAACC AGCCCTTTAA TTACATCTCC CCATACTGGA TTTGACAATG     60
CCACTTGATA AGCAAAAATC ACAAAAATAA CAACAATTAA AGCAACAACA ATAGCTTCAA    120
TTTTTCTAAA ACCAATTTTT GTCAATAACA ACAAAGTAA AACATCAAAT ACCGTAATGA    180
AGACAGCCAG ACCTAAAGGA ATATGAAATA ATAAATATAA GGCAATTGCG CCCCCGATAA    240
CTTCAGCGAT ATCTGTAGCC ATAATTGCTA ACTCTGTTAA AATCCATAAT ACAATACCTA    300
ACGTCTTACT AGTTCTAGCA CGAATCGCTT GTGCTAAATC CATCTGTGAA CAATGCCTAA    360
TTTAGCAGCC ATATATTGGA GCAACATTGC AATCAAACTG GAAATTAAAA TAATCGACAT    420
```

```
CAATAAATAT TGAAAATTTT GTCCCCCAGT AATTGAAGTA GACCAGTTTC CTGGATCCAT      480
ATACCCCACT GCTACCAATG CTCCTGGACC TGAGTAAGCA AATAACGTTT TCCAAAAACT      540
CATATTTTTA GGCACGTCGA TGGTGCCATT AATTTCTTCA AGCGAAGGAC CATTTGCATA      600
TTCAATCAAA TGATGTCTTT GCTTGGTTC  ATGTTCTTCT GAATTTTTCA ATTCAATTCC      660
TTCTTTCGTT TTGCAATAAT TTTAAAAGGC CCTTCCCGTT AGAAGGTTAA CCTCTAGTAT      720
ATTTTAGGTA CACCTAAAAT ATACTGCTAA AAATAACAAA ATGCAAGACT GAAAGAAAA       780
TTTTGACAGT GTAAAATAG  ATTGTCGTAA ATGTGCGATC TTAAAGTTTG AAGAAATCAG      840
GGTAGCTGGT AGTTGATTAT CTTAAGAAGT AGAAAATAAG GGACCTAAGT CATTTCGGCT      900
TAGGTCCCTT ATTTATTTT  TATTCGGTTA TTCTATTAAG AATGGATGCT ACAATTCTG       960
TCGTGTCAGC TGAATGATTT CTAAAATCTC GTAAACTTAA TCTGACGAAA ACCTTCAAGT     1020
ACTTCGGGCA ACTTATTTTN CCCCCATTCA AAAGTTCCAT CATTTCTTTT CAATAATCTT     1080
TGTAAAATTT CTTCTTTCTC GACCGCTAAC AAAAAATGAT AAACGTCAAT GCCTGCTCGT     1140
CTCAGATATC CAATCAGCTC TTCTTCATAT TCATTTTAT  AAAGGGTCAT TGTAACAATA     1200
ATCGGCCGTC CAGACTCTTT GGACATTCGT TTTAATAAAT GAGCATTCCA GCAACGCCAT     1260
TCCTGATACT CCTGAAAATC ATTTTCTTTC ATTCTTCGG  GAACTAGCTC CATCAATGCA     1320
CTACCAATAA TTTCTGGATC ATAAATGATT GCGTTGGGAA GTTTTGTTG  TAACTCATGT     1380
GCAATGGTCG TTTTTCCGGA TCCAAACGCA CCGTTTAACC AAATAATTAT CATAATTTCC     1440
TTTTCTTCTG AACAAATTTC TTTGTTGTTT AATTTAGGTG CTAGATTACT TTTAATTTTT     1500
TTAGCCATTC ACTTATAGTT ACTACTTACA TCTTTAACAG TAAACGAGAC AAACTAAAAA     1560
TACAACATCC TACGCTATTA ACCTCGGGTT ATATAACATA CTCATCTGAT AATTTCTCCC     1620
TAAAAAAACA GAATGTGGGC AATCTTTTA  AGAATAATTG AATAGAATAA CAACAAACAG     1680
TAATTCAGGT ATAACCAGCT AGAAATTGTT TTATTTTAG  TCACGAGTAT GATAAGCATG     1740
TAAATCAAAT AGAATCATAT TAGGTGAGGT TACTCTGAAG AACACAGGTT ATCGCTCGGA     1800
AATGTCGAGA GACAGTAACG AGTAAAGCAG GGATTGTCGA ATTAAGGCTT TCCTAAGATA     1860
ACTAGAATTT TTTTCTTACG TCTCAGAAAG CCAAAGCTCA ATTATTGTGA TTACCCTATA     1920
ATCTTCTTCT TTTATTCGGC GACCTCTTTA ATATGATTAA TTGGAGGTTT TTAAATTGAA     1980
AGCTGTCACT GCATCATCTA AGAAAAATAC CCTACTTGCT AAAAGTATCG GGAATCTTAC     2040
CTTGCTCATC ATTTTAGGCA TTTTCATTTT TATCATCGTC TTCTCTTGGC TAAAAATGAA     2100
TCGCCCTCTC CACACCCTTC CCTCAGAAGA ATTCCTCGCA ACACCAAGTA AAACAGATGA     2160
TTTCTTATCT CCATCAAATC TTTTTTACTT TTCAATTCGA ACCATGTTTC GAATGATTGT     2220
GGGGATGGCT TGGTCCTTCC TGTTTTCCTT TGTTTTGGT  ATTTAGCCG  TAAAATATAA     2280
AACGGCACGA AGAGTCATTT TACCATTAGT TAATTTCCTT GAATCTGTTC CATTGCTAGG     2340
TTTTTTGACC TTTACAACTG CTTGGTTACT TGGTTTATTT CCAGGAAATG TGATGGGCGC     2400
AGAAGCGGTT GCTATTTTTG CCATCTTCAC AGGTCAAGCT T                        2441
```

( 2 ) INFORMATION FOR SEQ ID NO:13:

( i ) SEQUENCE CHARACTERISTICS:
        ( A ) LENGTH: 9515 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
  ( A ) ORGANISM: Pseudomonas aeruginosa
  ( B ) STRAIN: Clinical Isolate P2- 2

( x i ) SEQUENCE DESCRIPTION: SEQ ID NO:13:

| | | | | | | |
|---|---|---|---|---|---|---|
| AAGCTTTCCT | CCAGACCCTT | CACCGCCGTG | GAGATCGACG | GCTGGGCGAT | GTACAGCTTG | 60 |
| CGCGAGGCCT | CGGCCACGCT | GCCGCATTCC | ACGGTGGTCA | CGAAATACTT | GAGTTGCCGC | 120 |
| AAGGTATAGG | ACGCCACTGC | AAGACCTCAT | CGGCGCATCA | TCCTCCCCGG | GCCGGGCGTG | 180 |
| CGCGCCTCGA | TTGTTGTGTC | CGCCGCGCTG | CAAGCAAGTT | GCAGGCCGCT | GCCGAGCGTC | 240 |
| GCGCGCTGGC | CGCGGAACGA | TTGCCCGCCT | GCACGATAAC | CCAGCACGAC | GCACTTTGCC | 300 |
| GGGGCACGCC | TGGCCAGCTT | TTTCTTATGT | CCCGAGGACA | TTTTAATAA | TTTTCCTTCG | 360 |
| CCGCGGCTTG | CGCGACCATC | CTTCCCCATC | GACCCCATGG | ACAGCGGTTC | GCCTCCCGGC | 420 |
| GGTCCGGGCC | ATGCGTGCAG | AACCACGACC | GGCGCAGACC | GGCGAGATAA | CAAGGAGAAG | 480 |
| GTGGGGTGTT | CGAACTCAGC | GATTGGCAAC | GGCGCGCCGC | GACACAGCGC | TTCATCGACC | 540 |
| AGGCCCTGAT | CGGCGGCCGC | CAGCGTCCAG | CCGCCAGCGG | CGCTACCTTC | GACGCCATCG | 600 |
| ATCCGGCGAG | CAATCGCCTG | CTGGCGCGGG | TCGCGGCCTG | CGATGCGGCC | GACGTCGACG | 660 |
| CGGCAGTGGC | CGCCGCCCGC | CGCGCCTTCG | ACGAAGGCCC | CTGGGCGCGT | CTCGCCCCGG | 720 |
| TCGAGCGCAA | GCGCGTGCTC | TGCGCCTGGC | CGAGCTGATG | CTGGCCCATC | GCGAAGAGCT | 780 |
| GGCGCTGCTC | GACTCGCTGA | ACATGGGCAA | GCCGGTGATG | GACGCCTGGA | ACATCGATGT | 840 |
| ACCCGGCGCC | GCCCACGTCT | TCGCCTGGTA | TGCGGAAAGC | CTCGACAAGC | TCTACGACCA | 900 |
| GGTCGCGCCG | GCCGCCCAGC | AGACCCTGGC | CACCATTACC | CGCGTGCCGC | TGGGGGTGAT | 960 |
| CGGCGCGGTG | GTGCCGTGGA | ACTTCCCGCT | CGACATGGCC | GCCTGGAAGC | TCGCCCCGGC | 1020 |
| CCTGGCCGCC | GGCAACTCGG | TGGTGCTCAA | GCCGGCCGAG | CAGTCGCCGT | TCTCCGCCCT | 1080 |
| GCGCCTGGCC | GAGCTGGCCC | TGGAGGCGGG | GGTGCCGGAA | GGCGTGCTGA | ACGTGGTGCC | 1140 |
| GGGCCTCGGC | GAGCAGGCCG | GCAAGGCCCT | CGGCTTGCAC | CCGGAGGTGG | ACGCACTGGT | 1200 |
| GTTCACCGGC | TCCACCGAGG | TCGGCAAGTA | CTTCATGCAG | TATTCCGCGC | AATCCAACCT | 1260 |
| CAAGCAGGTC | TGGCTGGAGT | GCGGCGGTAA | GAGTCCGAAC | CTGGTGTTCG | CCGATTGCCG | 1320 |
| CGATCTTGAC | CTGGCGGCGG | AAAAAGGCGC | CTTCGGCATT | TTCTTCAATC | AGGGCGAGGT | 1380 |
| CTGTTCGGCG | AACTCGCGCT | TGCTGGTGGA | GCGTTCGATC | CACGACGAGT | TCGTCGAGCG | 1440 |
| CCTGCTGGCC | AAGGCCCGCG | ACTGGCAGCC | GGGCGATCCG | CTGGACCCGG | CCAGCCGCG | 1500 |
| CCGGCGCCAT | CGTCGACCGC | CGGCAGACCG | CCGGGATTCT | CGCCGCCATC | GAGCGGGCGC | 1560 |
| AAGGCGAGGG | CGCGACCCTG | CTCGCGGTGG | CCGCCAGTTG | ACGATCAACG | GTTCGGACAA | 1620 |
| CTTCATCGAA | CCGACCCTGT | TCGGCGACGT | ACGCCCGGAC | ATGCAGCTGG | CCCGCGAGGA | 1680 |
| AATCTTCGGC | CCGGTGCTGG | CGATCAGCGC | CTTCGACTCC | GAGGACGAGG | CCATACGCCT | 1740 |
| GGCCAAGGAC | AGCCGCTACG | GCCTCGCCGC | CTCGCTGTGG | AGCGACGACC | TGCACCGTGC | 1800 |
| GCACCGGGTG | GCGCGGCGCT | TGAATGCCGG | AACGTGTCGG | TGAATACCGT | GGACGCGCTG | 1860 |
| GACGTCGCGG | TGCCTTTCGG | CGGCGGCAAG | CAGTCCGGCT | TCGGTCGCGA | CCTGTCGCTG | 1920 |
| CATTCCTTCG | ACAAGTACAC | CCAGTTGAAG | ACGACCTGGT | TCCAGTTGCG | CTGAAGACGC | 1980 |
| GACGACGCG | ACACGACTCG | ATGCCGATAA | CGACAACAAG | AGGACGATCG | AATGAACGAC | 2040 |
| ACGCCGAACG | TGCGTGAGCC | GGCCCTGCGC | CGCGTGCTCG | GGCTGGGACC | GCTGCTGGCG | 2100 |
| GTGGCCATCG | GCCTGGTGGT | TTCCCAGGGC | GTGATGGTAC | TGATGCTGCA | AGGCGCCGGG | 2160 |
| ACGGCCGGCC | TGGGCTTCAT | CGTGCCGCTG | GGAGTGGCCT | ACCTGCTGGC | GCTGACTACG | 2220 |

```
CCTTTTCCTT TTCCGAGCTG GCCCTGATGA TTCCCCGCGC CGGTAGCCTG AGCAGCTACA   2280
CCGAGGTGGC CATCGGGCAT TTCCCGGCGA TCCTGGCGAC CTTTTCCGGC TACGTGGTGG   2340
TGGCGATGTT CGCCCTCTCG GCGGAACTGC TGCTGCTCGA CCTGATCATC GGCAAGGTCT   2400
ACCCCGGCGC GCTGCCGCCG ATGCTGGTGC TACGGCGTGC TCGGCCTGTT CACCCTGCTC   2460
AACCTGCTCG GCATCGACAT CTTCGCGCGC CTGCAGAGCG CGCTGGCGCT GCTGATGATG   2520
ATCGTCCTGC TGGTGCTCGG CCTGGGTGCG GTGAGCAGCG ACCACGCTTC CGCGCAGACC   2580
GCCCTGGCGA GCGGCTGGAA CCCGCTGGGG GTAAGCGCCC TGGCGCTCAC CGCGATGGCC   2640
GTGTGGGGCT TCGTCGGCGC CGAGTTCGTC TGCCCGCTGG TGGAGGAGAC GCGGCGTCCG   2700
GAGCGCAACA TCCCGCGTTC GATGATCCTC GGCCTGAGCA TCATCTTCCT GACCATCGCC   2760
CTCTACTGCT TCGGTGCGCT GCTGTGCATC CCGCAGGCGG AACTGGCCGG CGACCCGCTG   2820
CCACACTTCC TCTTCGCCAA CCGCGTGTTC GGCGAGTACG GCCAGCTGTT CCTGGTGATC   2880
GCCGCGATCA CCGCCACCTG CAGCACCCTC AACTCGTCGC TGGCGGCGAT CCCGCGGATG   2940
CTCTACGGGA TGGCGCAGAA CGGCCAGGCC TTCCCGCAAT TCAAGCAGCT CAGCCGGCGG   3000
GCGCGCACGC CCTGGGTGGC GGTGCTGTTC GTCGCCGCGA TCACCGGCCT GCCGATCCTG   3060
ATCCTCGGCC AGGACCCGGA CTCGATCAAC CTGCTGCTGC TCGCCGCCGC GCTGGCCTGG   3120
CTGCTGGCCT ACATCATCGC CCACGTCGAC GTGCTGGCCC TGCGCCGTCG CTATCCGCAC   3180
ATCGCCCGTC CGTTTCGCAC GCCGTTCTAC CCGCTGCCGC AACTGTTCGG CATCGCCGGG   3240
ATGATCTACG CGGTGGTCCA CGTCTCGCCG ACCCCGGAAA TGACCGGACG GATCTTCGCC   3300
AGCGCCGGCG TGGTGCTCGG CGTGGTCTCG CTGGTGGCGG TGGTGTGGAT CAAGGGCGTG   3360
ATGCGCAAGC CCCTCTTCGT ACCCGAACCG CTCGAGACGG CCGGTGAGAC TGCCCAGGGC   3420
AAGTCCGTCG CCCTCGATCC CCTGCAATCC CTTCGGCCTG ACGCGCCAAG GGAACAAGGA   3480
GAACACAGAC GATGACCGCT CAGCTCAACC CGCAGCGCGA CACCCGCGAC TACCAGCAAC   3540
TGGACGCCGC GCACCACATC CACGCCTTCC TCGACCAGAA GGCGCTGAAC CGCGAAAGGC   3600
CCGCGGGTGA TGGTCCGCGG CGATGGCCTG CAGCTCTGGG ACAACGACGG CAAGCGCTAC   3660
CTGGACGGCA TGTCCGGCCT CTGGTGTACC AACCTCGGCT ACGGCCGCCA GGACCTCGCC   3720
GCCGCCGCCA GCGCCAGCT GGAACAACTG CCGTACTACA ACATGTTCTT CCACACCACC   3780
CACCCGGCGG TGGTGGAGCT TTCCGAGATG CTCTTCAGCC TGCTGCCGGA CCACTACAGC   3840
CACGCGATCT ACACCAACTC CGGCTCCGAG GCCAACGAGG TGCTGATCCG TACCGTGCGG   3900
CGCTACTGGC AGATCCTCGG CAAGCCGCAG AAGAAGATCA TGATCGGCCG CTGGAACGGC   3960
TACCACGGCT CGACCCTGGG CAGCACCGCG CTCGGCGGGA TGAAGTTCAT GCACGAGATG   4020
GGCGCATGCT GCCGGACTTC GCCCACATCG ACGAACCCTA CTGGTACGCC AACGGCGGCG   4080
AGCTGAGCCC GGCCGAAGTT CGGTCGCCGC GCGGCGCTGC AACTGGAGGA GAAGATCCTC   4140
GAACTGGGCG CGGAGAACGT CGCCGCCTTC GTCGCCGAGC CCTTCCAGGG CGCCGGTGGC   4200
ATGATCTTCC CGCCGCAAAG CTATTGGCCG GAGATCCAGC GCATCTGCCG GCAGTACGAC   4260
GTGCTGCTGT GCGCCGACGA AGTGATCGGC GGCTTCGGCC GCACCGGCGA ATGGTTCGCC   4320
CACGAACACT TTCGCTTCCA GCCGGACACC TTGTCCATCG CCAAGGGCCT GACGTCCGGC   4380
TACATCCCCA TGGGCGGCCT GGTACTCGGC AAGCGCATCG CCGAGGTGCT GGTGGAGCAG   4440
GGCGGGGTGT CGCCCACGG CCTGACCTAT TCCGGCCACC GGTGGCGGC GGCGGTGGCC   4500
ATCGCCAACC TCAAGGCTGC GCGACGAGGG CGTGGTCACG CGGGTCAGGG AGGAGACCGG   4560
CCCCTACCTG CAACGCTGCC TGCGCGAGGT CTTCGGCGAC CATCCGCTGG TCGGCGAGGT   4620
```

-continued

| | | | | | |
|---|---|---|---|---|---|
| CCAGGGCGCC | GGCTTCGTCG | CCGCGCTGCA | GTTCGCCGAG | GACAAGGTGA | CCCGCAAGCG | 4680 |
| CTTCGCCAAC | GAGAACGATC | TGGCCTGGCG | CTGCCGCACC | ATCGGCGGCT | TCAGGAGGG | 4740 |
| CGTGATCATC | CGCTCCACCC | TCGGCCGCAT | GATCATGGCC | CCGGCGCTGG | TGGCCGGGCG | 4800 |
| TGCCGAGATC | GACGAACTGA | TCGACAAGAC | CCGTATCGCG | GTGGATCGCA | CCGCGCGCGA | 4860 |
| GATCGGCGTG | CTCTGACGCG | CCCCGGCGGC | CCGGCCTCGG | CCGGGTCGCC | TGCGACACGG | 4920 |
| AGCGTCCCCC | CATAACGACG | ATGCGGCGCC | TGGCGACCGC | GCGCGGAACC | GTTTCGGCCT | 4980 |
| CTGGCGGCAA | CTGCCTAAGC | AACATCACAA | CAATGCCAAT | CGGCTGTGGG | AGTGTTCCAT | 5040 |
| GTTCAAGTCC | TTGCACCAGT | ACGCACACGT | GTTTTCCCGG | TTGTCCCTGT | TCGTCCTGGC | 5100 |
| GTTCGCCGCG | GCGGCCCAGG | CGCAGAGCCA | GAGCCTGACG | GTGATCTCCT | TCGGCGGCGC | 5160 |
| GACCAAGGCC | GCCCAGGAAC | AGGCCTATTT | CAAACCCTTC | GAGCGAAGCG | GCGGCGGGCA | 5220 |
| GGTGGTCGCC | GGCGAATACA | ACGGCGAAAT | GGCCAAGGTG | AAGGCCATGG | TCGACGTCGG | 5280 |
| CAAGGTCAGC | TGGGACGTGG | TCGAGGTGGA | GAGCCCCGAA | CTGCTCCGCG | GCTGCGACGA | 5340 |
| GGGGCTGTTC | GAACGCCTCG | ACCCGGCGCG | TTTCGGCGAC | CCCGCGCAGT | TCGTCCCCGG | 5400 |
| CACTTTCAGC | GAGTGCGGGG | TGGCCACCTA | CGTCTGGTCG | ATGGTGATGG | CCTACGACTC | 5460 |
| GACGAAGCTG | GCCAGGGCGC | CGCAGTCCTG | GGCGGATTTC | TGGAACGTCC | GCGAGTTCCC | 5520 |
| CCGGCAAGCG | TGGCCTGCGC | AAGGGCGCCA | AGTACACCCT | GGAAGTGGCG | TTGCTGGCCG | 5580 |
| ACGGGGTGAA | GGCGGAGGAC | CTCTACAAGG | TACTCGCCAC | CCCGGAGGGG | GTCAGCCGCG | 5640 |
| CCTTTCGCCA | AGCTCGACCA | GCTCAAGCCG | AACATCCAGT | GGTGGGAGGC | CGGCGCCCAG | 5700 |
| CCGCCGCAAT | GGCTGGCGGC | CGGCGACGTG | GTGATGAGCG | CGGCCTACAA | CGGGCGCATC | 5760 |
| GCCGCTGCGC | AGAAGGAGGG | GGTGAAACTG | GCCATCGTCT | GGCCCGGCAG | TCTCTACGAT | 5820 |
| CCGGAGTACT | GGGCGGTGGT | GAAGGGCACC | CCGAACAAGG | CGCTGGCGGA | GAAATTCATC | 5880 |
| GCCTTCGCCA | GCCAGCCGCA | GACGCAGAAG | GTGTTCTCCG | AGCAGATCCC | CTACGGGCCG | 5940 |
| GTACACAAGG | GCACCCTGGC | GTTGCTGCCG | AAGACGGTGC | AGGAGGCGCT | GCCGACCCGC | 6000 |
| GCCGGCCAAC | CTCGAAGGCG | CGCGGGCGGT | GGATGCCGAG | TTCTGGGTGG | ACCACGGCGA | 6060 |
| GGAGCTGGAA | CAGCGTTTCA | ATGCCTGGGC | GCGCGCTGAG | CGCTGCGCGT | CGGCAAAAAA | 6120 |
| AATGACGGGC | CCCAAGTCGT | CCGGGCCCGT | CGGGTCAAAG | CGCTGACGGG | GTGATCAGCG | 6180 |
| CAGCTCTTCC | AACAACCCCT | GCAGATACCG | ACAGCCCTCG | GTATCCAGCG | CCTGCACCGG | 6240 |
| AAGGCGCGGC | GCCCCCACCT | CCAGGCCGGA | GAGGCCCAGG | CCGGCCTTGA | TGGTGGTCGG | 6300 |
| CAGGCCCCGG | CGGAGGATGA | AGTCGAGCAG | CGGCAACTGC | CGGTAGAACA | GCGCGCGGGC | 6360 |
| CTTCTCCAGG | TCGCCGTCGA | GCACCGCCTG | GTAGAGCTGG | CCGTTGAGCG | TCGGGATCAG | 6420 |
| GTTCGGCGCG | GCGCTGCACC | AGCCTTTCGC | GCCGGCCACG | AAGGCCTCCA | GCGCCAGCGC | 6480 |
| GTTGCAGCCG | TTGTAGAAGG | GCACCCGGCC | TTCGCCGAGC | AGGCGCAGCT | TGTGCATGCG | 6540 |
| CTGGATGTCG | CCGGTGCTCT | CCTTGACCAT | GGTCACGTTG | TCCACTTCGC | GGACGATGCG | 6600 |
| CAGGATCAGT | TCCACCGACA | TGTCGATGCC | GCTGGTGCCC | GGGTTGTTGT | AGAGCATCAC | 6660 |
| CGGCACGCCG | ATGGCTTCGC | CAACCGCGCG | GTAGTGCTGG | AACACTTCCG | CCTCGTTGAG | 6720 |
| CTTCCAGTAG | GAGATCGGCA | GGACCATCAC | CGCCTCGGCG | CCGAGGGATT | CGGCGAACTG | 6780 |
| CGCGCGGCGC | ACGGTCTTGG | CGGTGGTCAG | GTCGGAGACG | CTGACGATGG | TCGGCACGCG | 6840 |
| ATGGGCGACG | GTCTTCAGGG | TGAAGTCGAC | CACCTCGTCC | CATTCCGGGT | CGCTCAGGTA | 6900 |
| GGCGCCTTCG | CCGGTGCTGC | CGAGCGGGGC | GATGGCGTGC | ACGCCGCCGT | CGATCAGGCG | 6960 |
| CTCGATGGAG | CGGCCGAGGG | CCGGCAGGTC | GAGACCGCCG | TCGGCGCCGA | AGGGGGGTGA | 7020 |

```
TGGTGTAGCC GATGATGCCG TGGATGGATG CGGACATTGG ATGTACCCGT GACATTGAGT    7080
GGGAAATGCC AGGACGGACC TGGTGGGAAA GGTCGTTCAG CTCAGGCAGT CGCTGTTGCG    7140
CGGCAGGCAG CGCCGGGCGT AGTAGTTGAA TGCGGCGCCG TGGCGCTTCG GGGTGGAGAT    7200
CCAGTCGTGG GCCTCGCGCG CCAGGGCCGG CGGGATCGGC TTGATCTCTC CGGCGGCCAT    7260
CGCCAGCAAC TGCATCTTCG CCGCGCGCTC GAGCAGCACC GCGATCACGC AGGCCTCCTC    7320
GATGCTCGCA CCGGTGGCCA GCAGGCCGTG GTGGGAGAGC AGGATGGCGC GCTTGTCGCC    7380
GAGGGCGGCG GAGATGATCT CGCCTTCCTC GTTGCCTACC GGCACGCCCG GCCAGTCCTT    7440
GAGGAAGGCG CAGTCGTCGT ATAGCGGGCA AAGGTCCATG TGCGAGACCT GCAGCGGTAC    7500
TTCCAGGGTC GACAGCGCGG CGATGTGCAG CGGGTGGGTG TGGATGATGC AGTTGACGTC    7560
CGGGCGGGCG CGATAGACCC AGCTGTGGAA GCGATTGGCC GGATTCGCCA TGCCGTGCCC    7620
GTGGAGGACG TTGAGGTCTT CGTCGACCAG CAGCAGGTTG CCGGCGCTGA TCTCGTCGAA    7680
GCCCAGGCCC AGTTGCTGGG TGTAGTAGGT CCCCGCCTCC GGGCCGCGCG AGGTGATCTG    7740
CCCGGCGAGC CCGGAGTCGT GGCCGGCCTC GAAGAGAATC CGGCAGGTCA GGGCCAGCTT    7800
TTGCCGGTCA GTCCACGTAT TATCGCCGAG GCTGCTTTTC ATCTGCTTCA GCGCGTGCTG    7860
GATCAGTTGA TCCTTGGGTA ATTCCAGTGT CGTAACCATG CGAGGTTCCT TTGACGGAGC    7920
GAGTCGGGGG AAACGCCAGG CAGTTGCGCG CCACGCAACG ACCCGGCTGT AAATGACACG    7980
GATCAAGTTA TATGACACAA AGTGTCATTT AGCAAGAGAG AAGTTTCATC GCCATCGGGA    8040
GAAGGCTGTC CTCAATGTCC ATGCGCTTGA AATTGCTGAG AAAAAAACTC GGGGTCACGC    8100
TGGAGACCCT GGCCGACAAG ACCGGCCTGA CCAAGAGCTA CCTGTCCAAG GTCGAGCGCG    8160
GGCTGAACAC GCCGTCCATT GCCGCCGCGC TGAAGCTGGC GAAGGCGTTG AACGTGCAGG    8220
TGGAGGAGCT GTTCTCCGAG GAAAGCGACG GTGTCGACGG CTACAGCATC GTTCGTCGCG    8280
ACCAGCGCAA GTCGCTGTCC AGCGGCGACG ACGGCCCGGC CTACGCCTCC CTCGTCGCAG    8340
CAGATCGGCG CCCGCGCGCT GTTGCCGTTC ATCGTCCACC CCCCGCGCGA TTTCAGTCAC    8400
TCGACGTTCA AGGAGCACCT CGGCGAAGAG TTCATCTTCG TCCATGAGGG CCAGGTCGAG    8460
GTCGACTTCA TGAACCAGCG GATCATCCTC GAGCGCGGCG ACGCCCTGCA TTTCAACGCA    8520
CAGAAGCCGC ACCGCATCCG CTCCCTGGGG GAGACCCAGG CGGAATTGCT GGTGGTGATC    8580
CACAGCGACG AATGAGGCGA CGGCTTCGGT CGATCGGATG CTTGCTAACG TTCTGTTCGA    8640
TTATCGAACT GTTAATCGAT TATCGGATTG TGAGCCCTCG GACCCCGGCG TAAGGTTCTC    8700
GTCACGTGCC GTCCAGGCAG CGCACAACAA GACGAGACCC GACCGATGGC TGAAATCCTC    8760
TCCCTGCGCG AACGGTGCGA CGCTTCGTCC ACGATGGCGA CAGCGTCGCC CTCGAAGGCT    8820
TCACTCACCT GATCCGACG NCCGCCGGCC ACGAGCTGAT CCGCCAGGGC AGGAAAGACC    8880
TGACGCTGAT CCGCATGACT CCCGACCTGG TCTACGACCT GCTGATCGGT GCAGGCTGCG    8940
CGAAGAAGCT GGTGTTCTCC TGGGGCGGCA ACCCCGGTGT CGGTTCGCTG CACCGCCTGC    9000
GCGACGCGGT GGAGAAGGGC TCGGCCGCAA CCGCTGGAGA TCGAGGAACA CAGCCACGCC    9060
GACCTCGCCA ACGCCTATTT TGCCGGCGCC TCCGGGCTGC CCTTCGCGGT NTGCGCGCCT    9120
ACGCCGGCTC CGACCTGCCG AAGGTCAACC CGCTGATCCG CAGCGTCACC TGCCCGTTCA    9180
CCGGCGAAGT GCTGGCGGCG GTGCCCTCGG TGCGTCCGGA CGTCAGCGTG ATCCACGCGC    9240
AGAAGGCCGA CCGCAAGGGC AACGTGCTGC TCTGGGGCAT CCTCGGCGTG CAGAAGGAAG    9300
CGGCCCTGGC GGCGAAGCGC TGCATCGTCA CCGTCGAGGA GATCGTCGAC GAACTGGACG    9360
CCCCGATGAA CGCCTGCGTC CTGCCGAGCT GGGGCGCTCA GCGCCGTGTG CCTGGTGCCC    9420
```

-continued

| GGCGGCGCGC | ATCCGTCCTA | TGCCCACGGC | TACTACGAGC | GCGACAACCG | CTTCTACCAG | 9480 |
| GACTGGGACC | CGATCGCCCG | CGACCGCGAA | AGCTT | | | 9515 |

( 2 ) INFORMATION FOR SEQ ID NO:14:

( i ) SEQUENCE CHARACTERISTICS:
        ( A ) LENGTH: 2471 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 7

( x i ) SEQUENCE DESCRIPTION: SEQ ID NO:14:

| AAGCTTGTTC | CAGGCCCTCG | ACCGCTGCGA | TCTTCTGCGG | GTAGGCGGCG | ATGGTCTGTT | 60 |
| CGGAGTTCGC | CAACTGCAGG | CGACGCTGCG | CCAGCTGCGC | CGCCTGCACG | CCGGCAAGCA | 120 |
| TCAGGTCCTG | ATCGAGCGAG | GGGTTGAAGC | CGCGCACGAA | CTCGCTGAAC | TGGTCCACGC | 180 |
| CGAACAGGGT | GGCGATGAGC | TGGCGCTGAT | CGCTCGGGGT | CCGCGCGGCG | ATTCGGGCGA | 240 |
| AATCGTCGAG | GCGGTTCTTC | TCGATGAAGC | AGAAGCGATA | CTCAGCTTCG | TCGGGCTGGA | 300 |
| CGGCCTGCGC | CTCGCCCGCN | GCCGTAGACG | ACAGGACTGG | CGCGATGTGG | CGGCGCAGGC | 360 |
| GAGCGTTGTT | GCAGTACGTC | CGCTGGTCGA | CCGCTTGGCC | TGCGCTTCGC | TGATCGAACC | 420 |
| GAGCATCGCC | ACTTCCAAGG | CTTCGCAGAA | GCTGCTCTTG | CCGGTGCCGT | TGGCACGTNA | 480 |
| GACCAAGGTG | ATGTCATGGC | TGAGGTCGAA | CGTCTCCTGC | CGCATGAATC | CTCGAAACGG | 540 |
| CCCGACTTCG | AGCTGGTGCA | GTCGCCCGAG | CGCCGGCCCG | TTTTCGGGGC | CGCGCGCGTC | 600 |
| CCCGTCGTAG | GCGACAGGCA | TCTGCGCCAA | GATGCGCGAT | GGCCAGCGGC | GCCAAGCCGC | 660 |
| GTGGGAGCGC | CCCCGGCGT | GCAGCACCGA | CCTCGGCCAG | TGGCTGCAGG | TGATCGAGCA | 720 |
| CCAGGGTGCG | CCAGCCGGCG | CACCGTTTCG | TCGTGCACGT | GCCGCTGCGT | CAAGTGCGCC | 780 |
| AGGAACCGGT | GGTACTCCGA | ACGTATGCTT | GCCACAGCGA | CCCCTCACTT | GGTCAACCAC | 840 |
| TGACCGTAAG | CCTCCACATC | GATCATGGGG | ACCGTTCCAC | TGAACTGAAG | CTGCGCGATC | 900 |
| AGCTTGAAAA | GAAACGCGGT | CGCCGGCTTG | TTTTCGTTGG | TGTAGCTGTA | CGCGCCGCTG | 960 |
| GCTTGGTCAT | AGAAAAAGTG | CCCGTGGGCG | GCAACGCATC | CGATGTCCAG | ACGCCCCTCG | 1020 |
| GTGAGGTTTG | CGTTCAGCGC | CTTGTCCATG | GATGGGCCCA | ATGCAGGACT | CCATTCGCTC | 1080 |
| TCGAAGGTGA | GCAAGCCACC | CAGAATCGGA | ATCAACGCTT | CGCTGGGTAG | GTCCCGCCAG | 1140 |
| CGTGCGGGAT | CGGCAGGCTC | GTGCGGTGCA | GCCTGCGCAC | ACTGGCGACC | TTCTCCTGGC | 1200 |
| ATAGCCACAA | GCCCGCGTC | AGCCGTCTGC | TTGGCCTCGA | ACACGGCGTA | CACGCTTTCG | 1260 |
| GCTGGAATGA | TCGTCTCGTT | CTCGTAGGTG | AAGATAAAAG | GCGAATATTG | CCGATCAAAC | 1320 |
| ACCACCACAT | CGATCTGCTG | GCTGAAGTTC | CCCAGGCTGT | CCACCACATG | CGCCTTCGCC | 1380 |
| GCCTGGTACC | GTTTGGGCAG | ATAGGTATCC | AGCATGTCGA | TCCAGACGTT | CTCGCTCGCA | 1440 |
| TCCCCCTTCG | TACCCGGGTG | ACCGAAGGTC | TTGCGTACTA | CGGACAAGCG | CTGCTGGATG | 1500 |
| TCTTCATGCA | GGGACGACAG | GAGCTGGGAA | AGCGACCACT | GGGACATGCT | GTACCTCGAT | 1560 |
| GGGACGTGTA | TGGAAGCCGA | TGGAATCAGG | ACAGTGGGAA | CTTGGGGCCA | AACAGTGCGC | 1620 |
| GCCAGGGCGA | AGCGCTTCGA | TATTGCGACC | ACGACGCGTG | TGGTCGATGG | CGATGCTTGC | 1680 |
| GTCCTGGCTC | GCCTGGAACA | GCAGCTGCTN | GCGNGCGCTG | CTTGCGCGCG | GCATCCATAT | 1740 |
| CGTTGCTGAT | CGCCGGGCCA | AGTCCGGCGG | GATCCGGCCA | CTCGTCATGA | ACACGATCGG | 1800 |

| | | | | | | |
|---|---|---|---|---|---|---|
| CAAGCGTGGC | AAAGAACGAC | TGGATCTCGC | GATCGAACGA | TCCTCCCCAG | CCGCCGTAAA | 1860 |
| GACACTCAAG | GGCCATTACC | TCGATCAGGA | ACGAGGGCTT | CACCGGCTTC | TGATCGCCGT | 1920 |
| GCTTGGGATT | GTTGTTCCAG | TACTTCACCA | TGCGCACGAG | ACCTTTCCAC | TCATTGCCAT | 1980 |
| AGGCTTGGTG | CGCTGCGGTC | GCCTTGTCCT | TATGGATCTC | CGGGTCCGTC | TTGATCCACT | 2040 |
| TTCCGGACGC | CGTATCGGGG | ATCTCATACT | GGTCGCCGGT | GTCGAATGCG | GGCACCGCAT | 2100 |
| CCACGCTGAC | CACCCGGTAG | TCCGTGTTGT | CCTCCGCGTC | GATGTGAACA | CCGAAATCCA | 2160 |
| CGTTGATCGA | GNGCGCCTGT | TTGCGCACGG | CCGCCGAACC | GTATTCTCC | ACCAATGCAG | 2220 |
| AGTGGAAATC | ATCCAGCACT | ACCGATGCGG | CCTTGCCGTG | GTAATGCTTC | TCCGAGTCCT | 2280 |
| TCAGCACGAA | GAAGATGTCG | ATATCCTTGA | GCGGCTTCGT | CTTCGTGTAT | CGAGCATAGG | 2340 |
| ACCCGGTCAG | GAACTGCGCG | CAATGCCGAA | CTTGGTCTGC | AGGTAGTCCC | GCACTTCGTT | 2400 |
| CTGGCGTTGC | GAGGCATTCT | TCTGCTCGCG | TTCGTTGAGT | TCCAGACGCG | ACTTGAACTT | 2460 |
| GCGAAAAGCT | T | | | | | 2471 |

( 2 ) INFORMATION FOR SEQ ID NO:15:

( i ) SEQUENCE CHARACTERISTICS:
        ( A ) LENGTH: 5247 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 17

( x i ) SEQUENCE DESCRIPTION: SEQ ID NO:15:

| | | | | | | |
|---|---|---|---|---|---|---|
| AAGCTTCGAG | GGGGCTGGGC | GAGGATCGAC | CGGCCCCGCT | CGTGTCGGAA | GGGAAGGCCA | 60 |
| GGGCTGGCCT | GCCCGTTCGG | CGCTTCGGCA | GGCTGGCGCA | GAACGATGCA | AGGTCGTTCG | 120 |
| GGTCAGCATC | AGGGATGAAA | TGACTGACAG | GAGTCGGGAT | GCTGCGTTAC | GTCGTGGGTT | 180 |
| TTCTCGCGTT | CACCGTGCTG | GCGGCCTATC | TGTTGCTGGG | GGTTTCCCAG | CACGCCTTCC | 240 |
| TGCCGTGACC | GGTCGGCATG | GCGGCTTCAG | CTGCGTTGCG | GAAGAGGCTG | TGGCGGCCGT | 300 |
| GCGGGATGCC | GGTTTTCGGC | TTGCCGTGCC | TTGCGTTGCA | GGCGTCGCGC | CGACGCGGCA | 360 |
| CGCCAGGGAA | GGCCCACAGG | GTGACGCCGG | CGAGGCCCAG | CCAGGCGACG | ATCAGCAATG | 420 |
| TGACGAAGGA | TTCGGGAGTC | ATGGTTCGTC | CTCCTCTTAC | CCAAGGATAG | ACCCTGCGGG | 480 |
| AAGGGGAATT | ACTGCAATCG | GTCTTCGACC | ATGGTCTGAA | ACGCGGTCAC | TCGGGGCCGG | 540 |
| CGCCGACCAG | GGCCAGGCAG | CCGGTGAGGC | TGGTCAGCAG | GGGCAGGGCG | AGCAGGAAAG | 600 |
| CCAGCCAGAT | GGCCTCCATG | CGCAACAGCG | TGGCGCCGAG | GAACAGCGCG | ACCAGGAGGA | 660 |
| TGGTCATGAG | CAGGGCGGTC | CAGCCGAAGT | ACATGGCGAA | GTTGTCGATG | CCCAGGCCGA | 720 |
| TGCCCCAGCC | CAGCAGCAGG | GCCCATACCC | CGGCCAGAGC | CAGGCCGAGG | GCCAGCATGC | 780 |
| TCGCCAGGGT | CCGGGCGGAC | GGGGCATGCA | GCGGGTGGTT | GCGGAATAGC | TCGTAGAAGA | 840 |
| TCGGCGTATT | CATCGGCGTC | ACCTCCGCAG | GGGAACTTCC | AGCCTAGTCC | AGCGGGCGAG | 900 |
| ACGGCCCTAG | ACCTATTTGT | CATTACGAGG | CGTGACCTCA | GGCCGTTAAC | ATCCATCTTT | 960 |
| TTCCAGGCGA | TGCCGTGCAT | CGGGCTGCGG | GCCCGCTCAC | CGTTCGTCGC | GCTGAGTCGA | 1020 |
| AAAAGAAACC | GAAAGGGTTG | CGTGCATGAG | TTGGCGAACT | CGCCTCGTTC | GAGGTGGATG | 1080 |
| GGTATCAACT | GGTCTATCAG | GACCTGGGTG | AAGGCACGCC | GGTGCTACTG | GTCCACGGTT | 1140 |

| | | | | | | |
|---|---|---|---|---|---|---|
| CGCTGTGCGA | CTACCGCTAC | TGGCAATGGC | AGTTGCGCAG | CTCGGCAAGC | ACCACCGGCT | 1200 |
| GATCGTGCCG | AGCCTGCGTC | ACTACTACCC | CGAGCGCTGG | GACGGGCAGG | GTGCGGACTT | 1260 |
| CACCAGCGCC | CGCCACGTCG | CCGACCTGCT | GGCGCTGGTC | GAGCGGCTCG | GCGAGCCGGT | 1320 |
| ACACCTGCTC | GGCCATTCCC | GTGGCGGCAA | CCTGGCGTTG | CGCCTGGCGC | TGGCCGCTCC | 1380 |
| GGACGCCCTG | CGTTCGCTGA | GCCTGGCCGA | TTCCCGGCGG | CGACTATGCC | GCCGAGGTCT | 1440 |
| ACGCCCACGC | CGGCCTGCCT | GCGCCCGAGG | AACCATTGGA | ACGCAACCAG | TTCCGGCGCC | 1500 |
| AGGCGCTCGA | ATTGATCCGT | GGCGGCGAGG | CGGAACGGGG | ACTGGAACTG | TTCGTCGATA | 1560 |
| CGGTGAGCGG | CGCCGGGGTA | TGGAAACGCT | CGTCGGCGAC | GTTCGCCGA | ATGACGCTGG | 1620 |
| ACAACGCCAT | GACCCTGGTC | GGGCAGGTGG | CCGACCAGCC | GCCGGCGCTG | GCGCTGTCGG | 1680 |
| AACTGCGCTC | GATCGACCTG | CCGAGCCTGA | TCCTCAATGG | CGAACGCAGC | CCGCTGCCAT | 1740 |
| TCCCGGCCAC | CGCCGAGGCG | CTGGCGGCGG | CCCTGCCGCG | CGCCGAGCTG | CAACGCATCC | 1800 |
| AGGGCGCGTC | CCATGGCCTC | AATGCCACCC | GTCCGGCGGC | TTTCAACCGG | TCGGTGCTGG | 1860 |
| AGTTCCTGGC | GCGCGTCGAT | GGCGTTGCGC | CGGACGTGGA | AACGTCCTGA | AGCGAGGCCG | 1920 |
| GGCGAACTGA | CCGCTCGTCA | GCTCGCCGCG | GATGCTTTAC | CATGCGTTCG | CGCCGGATCA | 1980 |
| GCTCCGGCGT | TTTTCGTCAG | TATCCATTCC | CAGTGATCTC | CGTCCGCGCG | CTTCGGCGCA | 2040 |
| GGGGTGCCGC | AAGGCGCCTG | CCACTGTGAG | GCAGGCCGGC | CCGGCGGGCG | ACGCTTACTG | 2100 |
| GCACATCCCA | ACCCACGTGG | CCTTTGGTAG | GGTCACCACT | AGAGAGAGCG | CCATGCCCAT | 2160 |
| CATTACTCTT | CCCGACGGCA | GTCAACGTTC | CTTCGATCAC | CCGGTCTCCG | TGGCCGAGGT | 2220 |
| GGCCCAATCC | ATCGGCGCAG | GCCTGGCCAA | GGCGACCCTC | GCCGGCAAGG | TCGACGGCCG | 2280 |
| CCTGGTCGAC | GCCTGCGACA | CCATCGATCG | CGACGCGACC | CTGCAGATCA | TCACGCCCAA | 2340 |
| GGACGAGGAA | GGACTGGAGA | TCATCCGCCA | CTCCTGCGCC | CACCTGGTCG | GCCATGCGGT | 2400 |
| CAAGCAGCTC | TATCCGACCG | CGAAGATGGT | CATCGGCCCG | GTGATCGAGG | AAGGCTTCTA | 2460 |
| CTACGACATC | TTCTTCGAGC | GCCCCTTCAC | CCCCGAGGAC | ATGGCGGCGA | TCCAGCAGGC | 2520 |
| ATGCGCGAGC | TGATCGACAA | GGACTACGAC | GTGATCAAGA | AGATGACCCC | GCGCGCCGAG | 2580 |
| GTCATCGAGC | TGTTCAAGTC | CCGTGGCGAA | GACTAACAAG | CTGCGCCTGA | TCGACGACAT | 2640 |
| GCCGGACGAG | AAGGCCATGG | GCCTGTACTT | CCATGAGGAG | TACGTGGACA | TGTGCCGCGG | 2700 |
| CCCGCACGTG | CCGAACACTC | GCTTCCTCAA | GGCGTTCCAG | CTGACCAAGA | TTTCCGGCGC | 2760 |
| CTACTGGCGC | GGCGACTCGA | AGAACGAGCA | GTTGCAACGC | ATCTACGGCA | CCGCCTGGGC | 2820 |
| CGACAAGAAG | CAACTGGCGG | CCTACATCCA | GCGCATCGAA | GAGGCCGAGA | AGCGCGACCA | 2880 |
| TCGCCGCATC | GGCAAGCAGC | TCGACCTGTT | CCACCTGCAG | GAAGAAGCGC | CGGGCATGGT | 2940 |
| GTTCTGGCAC | CCGAATGCTG | GAGCGTCTAC | CAGGTGCTCG | AGCAGTACAT | GCGCAAGGTC | 3000 |
| CAGCGCGACC | ATGGCTATGT | CGAAGTGCGT | ACCCCGCAGG | TGGTCGACCG | CATCCTCTGG | 3060 |
| GAGCGTTCGG | GCCACTGGTC | GAACTACGCC | GAGAACATGT | TCACCACCTC | CTCGGAAAGC | 3120 |
| CGCGACTACG | CGGTCAAGCC | GATGAACTGC | CCGTGCCACG | TGCAGATCTT | CAACCAGGGC | 3180 |
| CTGAAGTCCT | ACCGCGACCT | GCCNTGCGCC | TCGCCGAGTT | CGGCGCCTGC | CACCGCAACG | 3240 |
| AGCCGTCCGG | CGCGCTGCAC | GGATCATGCG | GTACGCGGCT | TTACCCAGGA | CGACGCGCAT | 3300 |
| ATCTTCTGCA | CCGAAGAGCA | GGTGAAGAAG | GAAGCGGCCG | ATTTCATCAA | GCTGACTTGC | 3360 |
| AGGTCTACCG | CGACTTCGTT | TCACCGACAT | CGCCATGAAG | CTGTCGACCC | GTCCGGCCAA | 3420 |
| GCGCGTCGGT | TCCGACGAGC | TGTGGGATCC | CGAAGGCGCG | CTGGCCGATG | CGCTGAACGA | 3480 |
| ATCCGGCCTG | GCCTGGGAAT | ACCAGCCGGG | CGAGGGCGCG | TTCTACGGGC | CGAAGATCGA | 3540 |

| | | | | | |
|---|---|---|---|---|---|
| GTTCACCCTG | AAGGACTGCC | TCGGCCGTAA | CTGGCAGTGC | GGCACCCTGC | AGTACGACCC | 3600 |
| GAACCTGCCG | GAGCGCCTGG | ACGCCAGCTA | CATCGCCGAG | GACAACAACC | GCAAGCGCCC | 3660 |
| GGTGATGCTG | CACCGTGCGA | TCCTCGGGTC | CTTCGAGCGC | TTCATCGGCA | TGCTCATCGA | 3720 |
| GCACTACGCC | GGAGCCTTCC | CGGCCTGCTG | GCGCCGACCC | AGGCAGTGGT | GATGAACATC | 3780 |
| ACCGACAAGC | AGGCCGATTT | CGCCGCCGAG | GTGGTGCGGA | TCCTCGGGGA | AAGCGGATTC | 3840 |
| CGTGCCAAGT | CCGACTTGAG | AAACGAGAAG | ATCGGCTTTA | AATCCGCGA | GCATACTTTG | 3900 |
| CTCAAGGTTC | CCTATCTCTT | GGTTATTGGA | GATCGGGAAG | TTGAATCGAA | GGCCGTCGCG | 3960 |
| GTGCGTACGC | GCGAAGGGGA | AGACCTGGGC | TCCATGCCCG | TCACCCAGTT | CGCTGAGCTG | 4020 |
| TTGGCACAGG | CGGTTTCCCG | GCGTGGTCGC | CAAGACTCGG | AGTAATCATT | ATTAAGCGTG | 4080 |
| AAATGAGACA | GGATAAGCGA | GCTCAACCGA | AACCCCGAT | CAACGAGAAC | ATCTCGGCTC | 4140 |
| GTGAGGTACG | GTTGATTGGA | GCTGATGGCC | AGCAGGTTGG | TGTTGTTTCG | ATCGATGAGG | 4200 |
| CGATCCGCCT | AGCCGAAGAG | GCGAAGCTGG | ACCTGGTTGA | GATTTCGGCC | GACGCGGTGC | 4260 |
| CTCCTGTCTG | CCGCATCATG | GACTACGGCA | AGCACCTGTT | CGAGAAGAAG | AAGCAGGCTG | 4320 |
| CGGTCGCCAA | GAAGAACCAG | AAGCAGGCGC | AGGTCAAAGA | AATCAAGTTT | CGTCCAGGGA | 4380 |
| CGGAAGAAGG | GGATTACCAG | GTAAAACTAC | GCAACCTGGT | ACGTTTCCTT | AGTGAAGGGG | 4440 |
| ACAAGGCCAA | GGTATCCCTG | CGATTCCGCG | GCCGTGAGAT | GGCTCACCAG | GAGCTGGGGA | 4500 |
| TGGAGCTGTT | GAAGCGGGTC | GAAGCCGACC | TCGTGGAGTA | CGGCACCGTC | GAGCAGCATC | 4560 |
| CTAAGCTGGA | AGGACGCCAG | CTGATGATGG | TCATCGCTCC | CAAGAAGAAA | AAGTAACCAC | 4620 |
| CAGGGCACTG | GCAGGCCTTG | CGGTTATGCG | TAATCACTCA | ATGCGGAGTA | TCCGAACATG | 4680 |
| CCAAAGATGA | AGACCAAAAA | GTGGGCGCGG | CCAAGCGCTT | CAAGAAGACT | GCTGGTGGCC | 4740 |
| TCAAGCACAA | GCACGCCTTC | AAGAGCCACA | TCCTGACCAA | GATGACCACC | AAGCGTAAGC | 4800 |
| GTCAACTGCG | CGGCACCTCG | ATGCTGAACA | AGTCTGACGT | TGCGCGCGTA | GAACGCTCCC | 4860 |
| TGCGTCTGCG | CTGATTATTA | AGGTAGAGGA | TTAATTCATG | GCTCGTGTTA | AGCGTGGCGT | 4920 |
| TATCGCCCGT | CGTCGTCACA | AGAAAATTCT | GAAGCTCGCC | AAGGGCTACT | ACGGTGCACG | 4980 |
| CTCGCGCGTG | TTCCGCGTTG | CCAAGCAGGC | GGTGATCAAG | GCTGGCCAAT | ACGCCTACCG | 5040 |
| TGACCGTCGT | CAGCGCAAGC | GTCAGTTCCG | CGCACTGTGG | ATCGCCCGTA | TCAACGCTGG | 5100 |
| TGCTCGTCAG | AACGGTCTGT | CCTACAGCCG | CCTGATCGCC | GGCCTGAAAA | AGGCGGCCAT | 5160 |
| CGAGATCGAC | CGTAAGGTCC | TGGCCGATCT | GGCAGTGAAC | GAAAAAGCGG | CGTTTACCGC | 5220 |
| GATTGTCGAG | AAAGCGAAGG | CAAGCTT | | | | 5247 |

( 2 ) INFORMATION FOR SEQ ID NO:16:

( i ) SEQUENCE CHARACTERISTICS:
        ( A ) LENGTH: 2812 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P4-5

( x i ) SEQUENCE DESCRIPTION: SEQ ID NO:16:

| | | | | | |
|---|---|---|---|---|---|
| AAGCTTTGGT | GATCTTAACG | TGACAAGCTC | CTTAGAAAAA | TTTTATGAGT | TTATTAGCGG | 60 |
| GGTCTTTCTT | GATCCGACTG | TACCAAGACT | TTCAACTCGT | AAAATACGCA | AGCACAAAAG | 120 |
| CACTGAAATG | CACTCTGCAC | GTTTGTCGCC | GTCCACGGTA | GCGGCATCCC | TCAATCACAC | 180 |

| | | | | |
|---|---|---|---|---|
| CGAAGCGGTG | AATCTTTCTA | CCTATGCAGA | GGCAACACCT | GAACAGCAGC AATCCGAGTT | 240
| CAGCCTGTTT | TGGGATGCAA | TACGCCACGC | TGCTCATGTT | GTGCGTGAGC GAAGCCGCAA | 300
| GGCTGTAGCA | AGTAGTGTCG | CAATAGCGGC | GGGTCACTGC | GAGGATTTCA ATAAGCCGAC | 360
| GTCTGCCACT | GATGTGGGAT | TGATTATAGA | GCCGAACTGC | CGCACCCAAT ATGGTTGTTT | 420
| GTACTGCGAA | AACTATTTAT | GTCACGGCGA | TGAGGAGGAT | CTGCATAAAA TTCTGAGTTT | 480
| GCAATACGTG | GTCAATGCCG | TGCGTAAATC | GGCCCCCGAT | GCAGCGCATA CTGAGGCACT | 540
| TTTCAAAGAG | TTATCTATCC | GGATCGAGTT | TATAGTCGAT | GCTCTTAGTG AGCGCTCTAG | 600
| CTCGGTGAAA | CAGACAGTCG | AAAAGGTTAA | AGCTAAGGTG | TTTGAATACG GCGAGTTAAC | 660
| TAAGTTTTGG | GAAGTCCGGT | TGGGTCGCTA | TGAAAAAATG | GGGATCGTAT TTGAGTGCT | 720
| GCTGTTCAGT | CGATAGGTAG | TCTTTTTTCT | AGCGGCCAGT | TTCCAGTCAC CAGCCAGCCA | 780
| GATAGTGCGG | CTCAGCTGTA | TGGGAAGCCC | GCGTCGGATT | TTGTTATCTG TCGCACTGAG | 840
| TATGGCAATG | CAACGGCAGT | GTACGGCGAG | TCTGTATGGG | ACTTTAACCC GTACAGGCTG | 900
| AGTGCAAAAA | AAATTGGCCG | AATACGCTTC | GATATGGTGT | TCGGTGATTA TGGTCATGAT | 960
| CAGCAAGCGC | TGATCGAAGA | AGCCAAATAT | CTTCTGTATT | GTCTTATTTA TTTCGCTGGC | 1020
| GGTGGGCGGA | TTGGTAAGCT | GAGTGCATCT | ACGATTATTT | CATATTGGGT TGTGCTGCGC | 1080
| ATCGCTATGA | AGTTCTGCTA | TGCGCAGAAA | AAGAAGTCAA | TGGTTGGTGT GCTGTCCTTG | 1140
| CAGCAGCTTT | TTACCGTGCC | TGTTTATCTA | GCGGCTTTTG | TTAGTGAAAG TAATTTTGAC | 1200
| AAGACGGTTC | TTAGTGGGAT | ATTGCACGGA | TTGATTAGTG | TGGGCGAGGA ACGCCTAGGG | 1260
| TATGTTGTGC | TGAATCCAAG | AGTTTTTGAT | TTGAGAAGAC | CTGATTCTAA ACAGCATTCC | 1320
| GGTAATTCCG | ACACGCCTTT | ATTTGAATTT | AATAATATTG | TGGCGACCTG CTCGATCATC | 1380
| TTACTTGGGT | GTTGGGAATA | TTGATTCATT | TATATCGTGC | TTTGCTGATG AGTATTTCGG | 1440
| TCTTACTCCG | CACCGTCAAA | AATCTTTGGG | GGTTGGTGGT | AAGTCGCGCT ATCGCCCCGG | 1500
| TATTCAGCAA | GCAATAGAGG | AATATGGTCT | GGCTGCGGTT | TTTGTCGGTG AGTTTGCCTG | 1560
| TTCCGAAAAG | AGAAAGCTGC | AGCGAGTCCT | TCTCAAGATG | CAGTATGTGG TGAGAATGGT | 1620
| GATACACCTA | TATACCGGCA | TGCGTGATCA | AGAGGTGATG | CGTATGTCTT ATAACTGCTT | 1680
| ATCTGATCAA | GTCGTGAGAT | GTTCAGTGGT | TGATGATCAA | GGTTTTATGC GCGATCAACC | 1740
| GCAATCAGTA | CACATATTAT | CGACTACCAC | GAAGTTTAGC | GGTTACAAGA AAGAAAGCGC | 1800
| ATGGTTCGCG | GCAGGCGAAG | TCGTCAAGGC | GGTCGAGGTT | GGCCAGGCGA TTTGTCGTGG | 1860
| TTTAGCCCGG | CTCTATAGGA | TTGAACTGGA | TGATCGTTGT | CCGCTATTCA TCAATCCGTC | 1920
| CGTCCTGTGT | AAAACGAAGA | ATTGTGCAGA | AGTTGGTGTA | ACAGACTTTA CATTGAGAGC | 1980
| AACGATGGCA | GTGCTTTGAA | ATCCTTATCG | ATTCAATCAG | AGGATTTACA AGAGTTGGCT | 2040
| CAGAGCGACC | CTTCTCGTGA | CTTTTACAAT | GAGCCAGATT | TGCAGTAGG CCAGCCCTGG | 2100
| CCGCTGACTA | GCCATCAATT | CCGACGTTCG | TTGGCCTTCT | ATGGAAGCAG TAGCGGCTTT | 2160
| CTCTCGTTAC | CGACTCTGCG | AGCGCAGTTC | AAGCATATGA | CCCATTCAGA TGGCGCGCTA | 2220
| TTATGCGAAT | GGCTTTGATA | ACTTGCGCAC | CATTTTGGC | TACTATGACG AGAAGAAAAT | 2280
| AGACTTCGTG | CTACCATATA | ACCACTTTGC | TTTCGAGTTC | CAGATGGCCA TGCCGATGTC | 2340
| GGTGGCCAAT | CAGTTGATTG | CAGATCTGCT | GTTCAAAGAA | GAACCGCTGT TGGTGGCAC | 2400
| CGGTTCATAC | ATGCAGAGGC | AGAAAGAACG | TGTTGAAGCT | GGCGAGATAA AGATTGAAGA | 2460
| TATTCGTGCC | GATACAGAGC | TTCGGGTGAA | GAACGGTGCA | ATTAGCTATC GGCCAACGCT | 2520
| ACTCGGTGGT | TGCACCAAGG | TGGGCCGCTG | CGATTCCTTC | ATGCTCGGTG ACTATACTGA | 2580

```
ATGTTTGTCC  TGCGAGGGTG  CGATTATCAA  GCCCTCCAGG  TTAAGTGCGG  CCATTGAGGA    2640

TGCGAAAAAC  GAGTTGTCAA  ACTACGCAGA  AGACTCAGGC  GAATATCAAA  TTGTGAAGGG    2700

CGATATTGAG  CGCCTAATGG  TTTTCAAGAC  TCGCCTGATC  GACACTGTGG  AGCTTTAGTC    2760

ATGAAGTCTG  GTGAAGGAAT  AAGCAAGGGG  GTTGGTGCCT  GTCAGGAAGC  TT            2812
```

( 2 ) INFORMATION FOR SEQ ID NO:17:

( i ) SEQUENCE CHARACTERISTICS:
        ( A ) LENGTH: 3615 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 24

( x i ) SEQUENCE DESCRIPTION: SEQ ID NO:17:

```
AAGCTTTTCT  TGCGTGTTCT  TGTGAGGCTT  CCTTCGCCAT  TATCATCACG  ATCCACATAA      60

ATAAAGCCGT  AGCGCTTAGA  CATTTGTGAA  TGAGATGCAC  TGACTAAATC  AATTGGCCCC     120

CAACTGGTGT  ACCCCATAAT  ATCCACACCA  TCGGCAATCG  CTTCATTTAC  CTGTACCAGG     180

TGATCGTTTA  AATAGGCAAT  TCGATAATCG  TCCTGTATCG  AACCATCCGC  TTCAACGCTG     240

TCTTTTGCGC  CTAATCCGTT  CTCGACAATA  AATAACGGTT  TTTGATAACG  ATCCCAAAGC     300

GTATTTAACA  GAACCCGTAA  TCCAACCGGA  TCAATTTGCC  ACCCCACTC   TGAACTTTTC     360

AGATGCGGAT  TGGGGATCAT  ATTCAGTATG  TTGCCCTGCG  CATTTTTATT  AATGCTTTCG     420

TCGTGGGAAC  ACAACCAGTC  ATGTATAACT  AAAGAGATGA  ATCGACGGTA  TGTTTAAAT      480

CTCTGCGTCA  CTTTCAGTCA  TCTCAATGGT  GATATTGTGG  TCGCGGAAGA  AACGCTGCAT     540

ATAGCCGGGA  TACTGGCCAC  GCGCCTGAAC  ATCACCAAAG  AACATCCAGC  GCCGGTTCTC     600

TTCCATGGCC  TGCAACATAT  CCTGTGGCTG  GCAGGTGAGG  GGGTAAACCA  GCCCACCGAG     660

AAGCATATTG  CCGATTTTCG  CTTCGGGGAG  CAGGCTATGA  CAGGCTTTAA  CTGCCCGCGC     720

ACTGGCAACC  AGTTGATGGT  GGATAGCCTG  ATAAACTTCC  GCCTCGCCAC  TCTCTTCTGC     780

CAGCCCCACG  CCCGTGAATG  GCGCGTGTAA  CGACATGTTG  ATTTCATTAA  ACGTCAGCCA     840

TAACGCCACT  TTATGTTGGT  AGCGAGTAAA  GACCGTGCGG  GCGTAATGTT  CGAAGTGATC     900

GATGACCGCT  CGATTAGCCA  ACCGCCGTAG  TTTTTCACCA  GCCCATATGG  CATTTCGTAA     960

TGGGATAACG  TTACCAGCGG  CTTGATCCCC  GCCTGCGCCA  TTTCATCAAA  CAGCCGATCG    1020

TAAAACGCTA  ACCCCGCTTC  ATTCGGTTCG  ACTTCGTCGC  CCTGAGGGAA  AATTCGCGCC    1080

CAGGCAATGG  AAATACGCAG  ACAGGTGAAG  CCCATCTCGG  CAAATAACGC  GATATCTTCC    1140

GGGTAACGGT  GATAAAAATC  GATGGCGACA  TCTTTGATAT  TCTCTTTCCC  CAGGATGCGC    1200

GGTTCCATTT  TTCCCATTAC  GCATGAGGCT  GTAAATCTGA  GGTCGAGATC  CCTTTGCCAT    1260

CTTCCTGCCA  GGCACCTTCC  ACCTGATTGG  CAGCTGTTGC  GGCACCCCAA  AGAAATGTTT    1320

CTGGAAATGC  TTTCATAATT  AACTCCTTTT  ATCGTTAGCG  AATGATGGAT  AACAGCGGTT    1380

CACCTGCGCT  TATCTGCGCC  GTGCCGTGGG  GTAATACGTC  CGTAAAATCA  TCGCTATTAC    1440

TGATTAATAC  CGGCGTCGTC  AGATCAAATC  CGGCCTCGCG  AATAGCAGGG  ATATCAAAAG    1500

AAATCAGCCG  ATCGCCTGTA  TTGACCTTGT  CACCCACGTT  GACGTGAGCG  GAAAAGAATT    1560

TGCCGTCCAG  TTTTACGGTG  TCGATACCGA  CATGAATCAG  GATCTCCACA  CCATCATCTG    1620
```

| | | | | | | |
|---|---|---|---|---|---|---|
| ACTCAATGCC | AATGGCGTGT | AATGTGGCGA | ACAACGAAGC | AATTCGACCC | GCAACCGGAG | 1680 |
| AACGCACTTC | ACCAACCGAG | GGCAGAATGG | CAATACCTTT | ACCCAACAGG | CCACTGGCAA | 1740 |
| ACGTGGTATC | AGCGACGTGA | ATGAGCGACA | CAATCTCTCC | CGTCATCGGT | GAACAGATAC | 1800 |
| CGCCCTGCTC | AGGTGGTGTA | ATAACCTCTG | GTGTTTCTC | TTCGGGGCAC | CCTGCGCTGG | 1860 |
| CTGACGTTTA | GCGGTGATGA | AATGAAGCAT | CACCGTACCG | ACAAATGCGC | AACCGATGGC | 1920 |
| AATGACACCG | CCAATAACGC | TGGCCCAGAC | GGTGAAATCA | ATTCCCGTTG | ACGGGATGGT | 1980 |
| TTGCATGAAG | GTGAAAATAC | TTGGCAAACC | AAAGGAGTAG | ACTTTCGTTT | GCGCGTAGCC | 2040 |
| AATAATGGTG | GCCCCCAAAG | CCCCACTGAT | ACAGGCGATA | ACAAAGGGGT | ACTTACGCGG | 2100 |
| CAGGTTGACG | CCATATACCG | CTGGTTCGGT | GATACCAAAC | AGACTCGTCA | ACGCCGCTGA | 2160 |
| TCCCGCCACC | ACTTTTTTCT | GCGCATCGCG | TTCGCAGAGG | AAGACGCCGA | GCGCCGCCCC | 2220 |
| GACCTGCGCC | ATAATGGCGG | GCATTAACAG | CGGGATCATG | GTGTCGTAGC | CCAGCACGGT | 2280 |
| GAAGTTATTG | ATACACACCG | GCACCAGGCC | CCAGTGCAGT | CCGAACATGA | CGAAGATTTG | 2340 |
| CCAGAAGCCG | CCCATTACCG | CGCCCGCAAA | TGCAGGAACC | GCCTGATAAA | GCCAGAGATA | 2400 |
| ACCGGCGGCA | ATCAGTTCGC | TTATCCAGGT | TGATAGCGGC | CCCACCAGCA | GAAAGGTGAC | 2460 |
| GGGTGTGATA | ACCATCAGAC | ATAGCAATGG | TGTGAAGAAA | TTTTGATTG | CCGACGGTAA | 2520 |
| CCACGCATTA | AGTCGGCGTT | CCAGAATGCT | GCACAACCAG | GCAGAAAAAA | TAATGGGAAT | 2580 |
| AACCGATGAC | GAGTAATTCA | ACAATGTGAC | CGGAATACCC | AGGAAATCCA | GCCCCAGCGC | 2640 |
| ATCCGCTTTT | GCGCGTTCTC | GAAAAGCAGT | ACAGAATTAA | TGGATGCACT | AACGCTCCAC | 2700 |
| CAATCACCAT | GGCAGTAAAT | GGATTATCGC | CGAAGCGTTT | CCCCGCGGTG | TATCCCAGGA | 2760 |
| TTATCGGGAA | GAACCAAAAC | AAGGCATCAC | TGGCGCTGAA | TAAAATTAAA | TAAGTACCAC | 2820 |
| TTTGTTCGGG | CGTCCACTGA | AAAGTGAGCG | CCAGAGCCAG | CATACCTTTC | AAGATCCCCG | 2880 |
| GTTGCCCGCC | ATCAAACCGA | TACAGAGGCG | TAAAAATACC | TGAAATAACA | TAAACAAAGC | 2940 |
| GGTTTAGACA | GATTACCTTT | ATCATACATT | TTCCGGTGCC | TGTTGCGCTT | TTTCGTCAAG | 3000 |
| GCCTGCCACA | CTGTTAACCG | CCAGGAAGAC | ATCGGCCACA | TGGTTACCTA | TGACCACCTG | 3060 |
| AAACTGGCCA | CCGCTTTCCA | CCACCATAAT | AATACCGGGG | GTCTTTTTCA | GTACCTCTGC | 3120 |
| TTGCGCTTTG | CTTTCATCCT | TTAATTTAAA | AACGTAAATC | GCGTTGCGCA | ATGCATCAGA | 3180 |
| CTCACAATGT | TATCTGCGCC | CCCGACTCCT | GCGACTATTT | TTCTGGCTAA | CTCCGTCATA | 3240 |
| ACTTGCCCTC | TACGCTTTGC | GGCAAAACTC | CAAAAAAAAA | CCTGAAAAAA | ACGGCCTGAC | 3300 |
| GTGAATCAAG | CAATTTTTTT | CAGGTTTTGC | CCGCTTAGTG | CGGTAACAAT | CCTTTACTCA | 3360 |
| GTAATAATAT | TTCAGTGTTC | TTTGCGCACG | CGCTCTATAT | TTATGGCTAA | AAACATAATC | 3420 |
| TCTGCGGGTG | AAATTTTACG | TTGATACTGC | AAACCAATAA | AAATGGCGAT | CCGTTCCGCA | 3480 |
| CATTGCCATG | CTTGCGGGTA | ATTTTGTTTT | ACTGCTTGTT | GTAATGATTC | ATCACTATCG | 3540 |
| TTAATTGAAG | CATGTTCAAG | AATACGCCAG | GATAAAAACT | TCAGATGTGT | AACCAGTCGC | 3600 |
| TGATAACTCA | AGCTT | | | | | 3615 |

( 2 ) INFORMATION FOR SEQ ID NO:18:

( i ) SEQUENCE CHARACTERISTICS:
        ( A ) LENGTH: 4954 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:

( A ) ORGANISM: Escherichia coli
( B ) STRAIN: Clinical Isolate EC- 34

( x i ) SEQUENCE DESCRIPTION: SEQ ID NO:18:

| | | | | | | |
|---|---|---|---|---|---|---|
| AAGCTTAACC | GCTCTCATCT | GTTGACCGCA | CGGCATAGCT | ATATTCTGCC | GGTCCTGGGA | 60 |
| CGTAGCGAGA | TTGACATGCA | AAAAACGGT | GCGCAGGCGG | TAACCGTTGA | GGATTCAATG | 120 |
| TCGATGATTC | ATGCCTCGCG | TGGCGTGTTA | AAACCCGCCG | GTGTAATGCT | GAAATCAGAG | 180 |
| TGTGCAGTGG | TCGCGGGAAT | CGCGCAGGCA | GCACTACCCC | AGAGCGTGGT | AGCCTGGGAG | 240 |
| TATCTGGTGG | AAGATTATGA | TCGCATTCGC | AATGACATTG | AAGCTGTGCT | GCCAGAGTTC | 300 |
| GCCGACTATA | ACCAGCGCAT | CCGTCATCCC | GGTGGTTTTC | ACCTGATAAA | TGCAGCTGCT | 360 |
| GAAAGGCGCT | GGATGACGCC | GTCAGGTAAG | GCTAATTTCA | TTACCAGCAA | AGGGCTGTTA | 420 |
| GAAGATCCCT | CTTCAGCGTT | TAACAGTAAG | CTGGTCATGG | CGACAGTACG | CAGCCACGAT | 480 |
| CAGTACAACA | CGACGATTTA | TGGTATGGAT | GATCGCTATC | GAGGGGTATT | CGGTCAACGA | 540 |
| GATGTGGTCT | TATGAGTGC | TAAACAAGCT | AAAATTTGCC | GTGTAAAAAA | CGGCGAAAGA | 600 |
| GTTAATCTTA | TTGCGCTTAC | GCCAGACGGT | AAGCGCAGTC | ACGCCGCATG | GATAGATTAA | 660 |
| AAGTGGTCAT | TTACCCTATG | GCTGACCGCT | CACTGGTGAC | CTATTTTCCA | GAATCGAATC | 720 |
| ACATGCTAAC | ACTTGATAAC | CACGATCCAT | TAAGTGGCAT | TCCTGGCTAT | AAAAGTATTC | 780 |
| CGCTTGAATT | AGAACCATCA | AATTAATGTC | TCTTCTCATT | TCTTCTGCTG | TCATCCGCAC | 840 |
| AGCAGAAGAA | TTCCTCATTG | ACTATTATTT | CGCAATTTGC | TCACATGGAT | TAAATTAAAC | 900 |
| TACATACTAT | AAGATATAAA | CTTCTGCCTA | CAGCTGTAAG | AAACTCCGCT | CAGTACTGAA | 960 |
| GCACCAGTCC | TATTTCCTCT | TTTCTCCAGC | CTGTTATATT | AAGCATACTG | ATTAACGATT | 1020 |
| TTTAACGTTA | TCCGCTAAAT | AAACATATTT | GAAATGCATG | CGACCACAGT | GAAAAACAAA | 1080 |
| ATCACGCAAA | GAGACAACTA | TAAAGAAATC | ATGTCTGCAA | TTGTGGGTGT | CTTATTACTG | 1140 |
| ACACTTACGT | GATAGCCATT | TTTTCGGCAA | TTGATCAGCT | GAGTATTTCA | GAAATGGGTC | 1200 |
| GCATTGCAAG | AGATCTTACA | CATTTCATTA | TCAATAGTTT | GCAAGGCTGT | AAACAAACAG | 1260 |
| CAAATTATAA | ATATGAAATG | TTAAAAAGT | ATCGATAAAA | ACTTTATTGT | TTTAAGGAGA | 1320 |
| TAAAATGTCG | CTCGTTTGTT | CTGTTATATT | TATTCATCAT | GCCTTCAACG | CTAACATTTT | 1380 |
| AGATAAAGAT | TACGCCTTCT | CTGACGGCGA | GATCCTGATG | GTAGATAACG | CTGTTCGTAC | 1440 |
| GCATTTTGAA | CCTTATGAGC | GGCATTTTAA | AGAGATCGGA | TTTACTGAAA | ATACCATTAA | 1500 |
| AAAATATCTA | CAATGCACTA | ACATCCAGAC | AGTGACGGTG | CCTGTTCCTG | CGAAGTTTTT | 1560 |
| ACGTGCTTCA | AATGTACCGA | CTGGATTGCT | TAATGAAATG | ATTGCTTATC | TCAACTCGGA | 1620 |
| AGAACGCAAT | CATCATAATT | TTTCAGAACT | TTTGCTTTTT | TCTTGCCTGT | CTATTTTTGC | 1680 |
| CGCATGCAAA | GGTTTCATTA | CACTATTAAC | TAACGGTGTG | CTATCCGTTT | CTGGGAAAGT | 1740 |
| GAGAAATATT | GTCAACATGA | AGCCGGCGCA | CCCATGGAAG | CTGAAAGATA | TTTGTGACTG | 1800 |
| CCTGTACATC | AGTGAAAGCC | TGTTGAAGAA | AAACTTAAGC | AAGAGCAAAC | GACATTCTCA | 1860 |
| CAGATTCTTT | TAGATGCAAG | AATGCAGCAC | GCAAAAAATT | TGATACGCGT | AGAAGGTTCA | 1920 |
| GTCAATAAAA | TTGCCGAACA | ATGTGGTTAT | GCCAGTACAT | CTTATTTTAT | TTATGCGTTC | 1980 |
| CGCAAACATT | TCGGCAACAG | TCCGAAGAGA | GTTTCTAAGG | AGTACCGTTG | TCAAAGTCAC | 2040 |
| ACGGGTATGA | ATACGGGCAA | CACGATGAAT | GCTTTAGCTA | TTTGATTATT | TGCTAACGAG | 2100 |
| TAGTCAACCA | CACACGCTGC | GTAAGAATTA | AATGGGGCAG | CCATTCCCTG | CCCCGCGTTG | 2160 |
| TTTTTAGGCG | ATATATTTAT | TGAAATAAAT | AAGTGACATC | CATCACATAT | TTATGCACTT | 2220 |
| GCATAACCTG | TTGCATGATT | ATTTATGATC | TCAATTCTGC | ATTTTGTCAG | TAAAATGCAA | 2280 |

```
TAATTTATTA AATATCAATA AATTAGTTGT TTATCGGCGA GAAATTACTT AATAGAACAG    2340
AAAGTAATGT CAACGCTTTA TGGACTGTTT TTTCCCTTTT TTTAGCTAAA TCTGCTATCT    2400
CTTTATGTGA CTAACTTCAC TTACATCCAC TTATTTCTCT TCGTAAAATT ACTTTGGAAT    2460
TAAGTACAAT AAGAAGAGGA ACATTATGA AGTCTGCATT AAAGAAAGT GTCGTAAGTA      2520
CCTCGATATC TTTGATACTG GCATCTGGTA TGGCTGCATT TGCTGCTCAT GCGGCAGATG    2580
ATGTAAAGCT GAAAGCAACC AAAACAAACG TTGCTTTCTC AGACTTTACG CCGACAGAAT    2640
ACAGTACCAA AGGAAAGCCA AATATTATCG TACTGACCAT GGATGATCTT GGTTATGGAC    2700
AACTTCCTTT TGATAAGGGA TCTTTTGACC CAAAAACAAT GGAAAATCGT GAAGTTGTCG    2760
ATACCTACAA AATAGGGATA GATAAAGCCA TTGAAGCTGC ACAAAAATCA ACGCCGACGC    2820
TCCTTTCATT AATGGATGAA GGCGTACGTT TTACTAACGG CTATGTGGCA CACGGTGTTT    2880
CCGGCCCCTC CCGCGCCGCA ATAATGACCG GTCGAGCTCC CGCCCGCTTT GGTGTCTATT    2940
CCAATACCGA TGCTCAGGAT GGTATTCCGC TAACAGAAAC TTTCTTGCCT GAATTATTCC    3000
AGAATCATGG TTATTACACT GCAGCAGTAG GTAAATGGCA CTTGTCAAAA ATCAGTAATG    3060
TGCCGGTACC GGAAGATAAA CAAACGCGTG ACTATCATGA CACCTTCACC ACATTTTCTG    3120
CGGAAGAATG GCAACCTCAA AACCGTGGCT TTGATTACTT TATGGGATTC CACGCTGCAG    3180
GAACGGCATA TTACAACTCC CCTTCACTGT TCAAAAATCG TGAACGTGTC CCCGCAAAAG    3240
GTTATATCAG CGATCAGTTA ACCGATGAGG CAATTGGCGT TGTTGATCGT GCCAAAACAC    3300
TTGACCAGCC TTTTATGCTT TACCTGGCTT ATAATGCTCC GCACCTGCCA AATGATAATC    3360
CTGCACCGGA TCAATATCAG AAGCAATTTA ATACCGGTAG TCAAACAGCA GATAACTACT    3420
ACGCTTCCGT TTATTCTGTT GATCAGGGTG TAAAACGCAT TCTCGAACAA CTGAAGAAAA    3480
ACGGACAGTA TGACAATACA ATTATTCTCT TTACCTCCGA TAATGGTGCG GTTATCGATG    3540
GTCCTCTGCC GCTGAACGGG GCGCAAAAAG GCTATAAGAG TCAGACCTAT CCTGGCGGTA    3600
CTCACACCCC AATGTTTATG TGGTGGAGAA GGAAAACTTC AACCCGGTAA TTATGACAAG    3660
CTGATTTCCG CAATGGATTT CTACCCGACA GCTCTTGATG CAGCCGATAT CAGCATTCCA    3720
AAAGACCTTA AGCTGGATGG CGTTTCCTTG CTGCCCTGGT TGCAAGATAA GAAACAAGGC    3780
GAGCCACATA AAAATCTGAC CTGGATAACC TCTTATTCTC ACTGGTTTGA CGAGGAAAAT    3840
ATTCCATTCT GGGATAATTA CCACAAATTT GTTCGCCATA CAGTCAGACG ATTACCCGCA    3900
TAACCCCAAC ACTGAGGACT TAAGCCAATT CTCTTATACG GTGAGAAATA ACGATTATTC    3960
GCTTGTCTAT ACAGTAGAAA ACAATCAGTT AGGTCTCTAC AAACTGACGG ATCTACAGCA    4020
AAAAGATAAC CTTGCCGCCG CCAATCCGCA GGTCGTTATA GAGATGCAAG GCGTGGTAAG    4080
AGAGTTTATC GACAGCAGCC AGCCACCGCT TAGCGAGGTA AATCAGGAGA AGTTAACAA    4140
TATCAAGAAA GCACTAAGCG AAGCGAAATA ACTAAACCTT CATGCGGCGG ATTTTTCCGC    4200
CGCCTTATTG AGCGAGATAG CGATGCACGT TACAGCCAAG CCCTCCAGTT TTCAATGTAA    4260
TCTCAAATGT GATTACTGTT TTTACCTTGA AAAGAGTCG CAGTTACTC ATGAAAAATG      4320
GATGGATGAC AGCACTTTGA AAGAGTTCAT CAAACAATAT ATCGCAGCGT CTGGCAATCA    4380
GGTCTATTTT ACCTGGCAAG GCGGTGAACC CACTCTGGCT GGCCTGGATT TTTTCCGTAA    4440
AGTTATTCAC TATCAACAAC GCTATGCAGG CCAAAAACGT ATTTTAATG CATTACAAAC     4500
GAATGGCATT TTATTGAATA ATGAATGGTG TGCCTTCTCA AAGAACATGA ATTTCTGGTG    4560
GTATCTCGAT CGATGGCCCC CAGGAGTTAC ATGACCGTTA CAGACGCAGT AATTCAGGTA    4620
ACGGTACTTT TGCAAAAGTG ATAGCAGCCA TCGAGCGTCT GAAATCATAT CAAGTAGAGT    4680
```

```
TTAATACGTT AACCGTCATT AATAACGTTA ATGTCCATTA CCCTCTTGAG GTTTATCATT    4740

TTTTAAAATC TATCGGCAGT AAACATATGC AATTTATCGA ATTGCTAGAA ACCGGGACGC    4800

CGAATATTGA TTTCAGTGGT CATAGTGAGA ACACATTCCG TATCATTGAT TTTTCTGTGC    4860

CTCCCACGGC TTATGGCAAG TTTATGTCAA CCATTTTTAT GCAATGGGTT AAAAACGATG    4920

TGGGTGAAAT TTTCATCCGT CAGTTTGAAA GCTT                                4954
```

(2) INFORMATION FOR SEQ ID NO:19:

(i) SEQUENCE CHARACTERISTICS:
        (A) LENGTH: 3796 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Escherichia coli
        (B) STRAIN: Clinical Isolate EC-39

(xi) SEQUENCE DESCRIPTION: SEQ ID NO:19:

```
AAGCTTAATC GCGTGAATCA GGAGTAAAAA AATGACAACC CAGACTGTCT CTGGTCGCCG      60

TTATTTCACG AAAGCGTGGC TGATGGAGCA GAAATCGCTT ATCGCTCTGC TGGTGCTGAT     120

CGCGATTGTC TCGACGTTAA GCCCGAACTT TTTCACCATC AATAACTTAT TCAATATTCT     180

CCAGCAAACC TCAGTGAACG CCATTATGGC GGTCGGGATG ACGCTGGTGA TCCTGACGTC     240

GGGCATCGAC TTATCGGTAG GTTCTCTGTT GGCGCTGACC GGCGCAGTTG CTGCATCTAT     300

CGTCGGCATT GAAGTCAATG CGCTGGTGGC TGTCGCTGCT GCTCTCGCGT TAGGTGCGCA     360

ATTGGTGCGG TAACCGGGGT GATTGTAGCG AAAGGTCGCG TCCAGGCGTT TATCGCTACG     420

CTGGTTATGA TGCTTTTACT GCGCGGCGTG ACCATGGTTT ATACCAACGG TAGCCCAGTG     480

AATACCGGCT TTACTGAGAA CGCCGATCTG TTTGGCTGGT TTGGTATTGG TCGTCCGCTG     540

GGCGTACCGA CGCCAGTCTG GATCATGGGG ATTGTCTTCC TCGCGGCCTG GTACATGCTG     600

CATCACACGC GTCTGGGGCG TTACATCTAC GCGCTGGGCG ACAACGAAGC GACAACGCGT     660

CTTTCTGGTA TCAACGTCAA TAAAATCAAA ATCATCGTCT ATTCTCTTTG TGGTCTGCTG     720

GCATCGCTGG CGGGATCATA GAAGTGGCGC GTCTCTCCTC CGCACAACCA CGGCGGGGAC     780

TGGCTATGAG CTGGATGCTA TTGCTGCGGT GGTTCTGGGC GGTACGAGTC TGGCGGGCGG     840

AAAAGGTCGC ATTGTTGGGA CGTTGATCGG CGCATTAATT CTTGGCTTCC TTAATAATGG     900

ATTGAATTTG TTAGGTGTTT CCTCCTATTA CCAGATGATC GTCAAAGCGG TGGTGATTTT     960

GCTGGCGGTG CTGGTAGACA ACAAAAAGCA GTAATAACGA CTACAGGCAC ATCTTGAATA    1020

TGAACATGAA AAAACTGGCT ACCCTGGTTT CCGCTGTTGC GCTAAGCGCC ACCGTCAGTG    1080

CGAATGCGAT GGCAAAAGAC ACCATCGCGC TGGTGGTCTC CACGCTTAAC AACCCGTTCT    1140

TTGTATCGCT GAAAGATGGC GCGCAGAAAG AGGCGGATAA ACTTGGCTAT AACCTGGTGC    1200

TGGACTCCCA GAACAACCCG GCGAAAGAGC TGGCGAACGT GCAGGACTTA ACCGTTCGCG    1260

GCACAAAAAT TCTGCTGATT AACCCGACCG ACTCCGACGC AGTGGGTAAT GCTGTGAAGA    1320

TGGCTAACCA GGCGAACATC CCGGTTATCA CTCTTGACCG CCAGGCAACG AAAGGTGAAG    1380

TGGTGAGCCA CATTGCTTCT GATAACGTAC TGGGCGGCAA AATCGCTGGT GATTACATCG    1440

CGAAGAAAGC GGGTGAAGGT GCCAAAGTTA TCGAGCTGCA AGGCATTGCT GGTACATCCG    1500

CAGCCCGTGA ACGTGGCGAA GGCTTCCAGC AGGCCGTTGC TGCTCACAAG TTTAATGTTC    1560
```

| | | | | | |
|---|---|---|---|---|---|
| TTGCCAGCCA | GCCAGCAGAT | TTTGATCGCA | TTAAAGGTTT | GAACGTAATG | CAGAACCTGT | 1620 |
| TGACCGCTCA | TCCGGATGTT | CAGGCTGTAT | TCGCGCAGAA | TGATGAAATG | GCGCTGGGCG | 1680 |
| CGCTGCGCGC | ACTGCAAACT | GCCGGTAAAT | CGGATGTGAT | GGTCGTCGGA | TTTGACGGTA | 1740 |
| CACCGGATGG | CGAAAAAGCG | GTGAATGATG | GCAAACTAGC | AGCGACTATC | GCTCAGCTAC | 1800 |
| CCGATCAGAT | TGGCGCGAAA | GGCGTCGAAA | CCGCAGATAA | AGTGCTGAAA | GGCGAGAAAG | 1860 |
| TTCAGGCTAA | GTATCCGGTT | GATCTGAAAC | TGGTTGTTAA | GCAGTAGTTT | TAATCAGGTT | 1920 |
| GTATGACCTG | ATGGTGACAT | AAATACGTCA | TCGACAGATG | AACGTGTAAT | ATAAAGAAAA | 1980 |
| GCAGGGCACG | CGCCACCCTA | ACACGGTGGC | GCATTTATG | GACATCCCGA | ATATGCAAAA | 2040 |
| CGCAGGCAGC | CTCGTTGTTC | TTGGCAGCAT | TAATGCTGAC | CACATTCTTA | ATCTTCAATC | 2100 |
| TTTTCCTACT | CCAGGCGAAA | CGTAACCGGT | AACCACTATC | AGGTTGCATT | GGCGGCAAA | 2160 |
| GGCGCGAATC | AGGCTGTGGC | TGCTGGGCGT | AGCGGTGCGA | ATATCGCGTT | TATTGCCTGT | 2220 |
| ACGGGTGATG | ACAGCATTGG | TGAGAGCGTT | CGCCAGCAGC | TCGCCACTGA | TAACATTGAT | 2280 |
| ATTACTCCGG | TCAGCGTGAT | CAAAGGCGAA | TCAACAGGTG | TGGCGCTGAT | TTTTGTTAAT | 2340 |
| GGCGAAGGTG | AGAATGTCAT | CGGTATTCAT | GCCGGCGCTA | ATGCTGCCCT | TTCCCCGGCG | 2400 |
| CTGGTGGAAG | CGCAACGTGA | GCGTATTGCC | AACGCGTCAG | CATTATTAAT | GCAGCTGGAA | 2460 |
| TCACCACTCG | AAAGTGTGAT | GGCAGCGGCG | AAAATCGCCC | ATCAAAATAA | AAACTATCGT | 2520 |
| TCGCTTAACC | CGCTCCGGCT | CGCGAACTTC | CTGACGAACT | CTGCGCTGTG | GACATTATTA | 2580 |
| CGCCAAACGA | AACGGAAGCA | GAAAAGCTCA | CCGGTATTCG | TGTTGAAAAT | GATGAAGATG | 2640 |
| CAGCGAAGGC | GGCGCAGGTA | CTTCATGAAA | AAGGTATCCG | TACTGTACTG | ATTACTTTAG | 2700 |
| GAAGTCGTGG | TGTATGGGCT | AGCGTGAATG | GTGAAGGTCA | GCGCGTTCCT | GGATTCCGGG | 2760 |
| TGCAGGCTGT | CGATACCATT | GCTGCCGGAG | ATACCTTTAA | CGGTGCGTTA | ATCACGGCAT | 2820 |
| TGCTGGAAGA | AAAACCATTG | CCAGAGGCGA | TTCGTTTTGC | CCATGCTGCC | GCTGCGATTG | 2880 |
| CCGTAACACG | TAAAGGCGCA | CAACCTTCCG | TACCGTGGCG | TGAAGAGATC | GACGCATTTT | 2940 |
| TAGACAGGCA | GAGGTGACGC | TTGGCTACAA | TGAAAGATGT | TGCCCGCCTG | GCGGGCGTTT | 3000 |
| CTACCTCAAC | AGTTTCTCAC | GTTATCAATA | AAGATCGCTT | CGTCAGTGAA | GCGATTACCG | 3060 |
| CAAAGTGAGC | GCGATTAAAG | ACTCAATTAC | GCGCCATCAG | CTCTGGCGCG | TAGCCTCAAA | 3120 |
| CTCAATCAAA | CACATACCAT | TGGCATGTTG | ATCACTGCCA | GTACCAATCC | TTTCTATTCA | 3180 |
| GAACTGGTGC | GTGTCGTTGA | ACGCAGCTGC | TTCGAACGCG | GTTATAGTCT | CGTCCTTTGC | 3240 |
| AATACCGAAG | GCGATGAACA | GCGGATGAAT | CGCAATCTGG | AAACGCTGAT | GCAAAACGC | 3300 |
| GTTGATGGCT | TGCTGTTACT | GTGCACCGAA | ACGCATCAAC | CTTCGCGTGA | AATCATGCAA | 3360 |
| CGTTATCCGA | CAGTGCCTAC | TGTGATGATG | GACTGGGCTC | CGTTCGATGG | CGACAGCGAT | 3420 |
| CTTATTCAGG | ATAACTCGTT | GCTGGGCGGA | GACTTAGCAA | CGCAATATCT | GATCGATAAA | 3480 |
| GGTCATACCC | GTATCGCCTG | TATTACCGGC | CCGCTGGATA | AAACTCCGGC | GCGCTGCGGT | 3540 |
| TGGAAGGTTA | TCGGGCGGCG | ATGAAACGTG | CGGGTCTCAA | CATTCCTGAT | GGCTATGAAG | 3600 |
| TCACTGGTGA | TTTTGAATTT | AACGGCGGGT | TTGACGCTAT | GCGCCAACTG | CTATCACATC | 3660 |
| CGCTGCGTCC | TCAGGCCGTC | TTTACCGGAA | ATGACGCTAT | GGCTGTTGGC | GTTTACCAGG | 3720 |
| CGTTATATCA | GGCAGAGTTA | CAGGTTCCGC | AGGATATCGC | GGTGATTGGC | TATGACGATA | 3780 |
| TCGAACTGGC | AAGCTT | | | | | 3796 |

( 2 ) INFORMATION FOR SEQ ID NO:20:

( i ) SEQUENCE CHARACTERISTICS:

(A) LENGTH: 5541 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Escherichia coli
(B) STRAIN: Clinical Isolate EC-625

(xi) SEQUENCE DESCRIPTION: SEQ ID NO:20:

```
AAGCTTAAGC CTGCATTTGC TCAATGAAGC GCAGAATGAG CTGGAACTGT CAGAAGGCAG      60
CGACGATAAC GAAGGTATTA AGAACGTAC  CAGCTTCCGT CTGGAGCGTC GGGTCGCCGG     120
AGTGGGTCGT CAAATGGGCC GCGGTAACGG CTATCTGGCA ACCATCGGCG CGATTTCTCC     180
GTTCGTTGGT CTGTTTGGTA CGGTCTGGGG CATCATGAAC AGCTTTATTG GTATCGCGCA     240
AACGCAGACC ACTAACCTGG CAGTCGTTGC GCCGGGTATC GCAGAAGCTC TGTTAGCAAC     300
GGCAATCGGC CTCGTGGCAG CGATTCCTGC GGTCGTTATC TATAACGTAT TGCACGCCA      360
GATTGGCGGC TTTAAAGCGA TGCTGGGTGA TGTTGCAGCG CAGGTATTGT TGCTGCAAAG     420
CCGTGACCTG GATCTGGAAG CCAGCGCCGC TGCGCATCCG GTTCGTGTCG CACAAAAATT     480
ACGCGCAGGA TAATATCCGA TGGCAATGCA TCTTAACGAA AACCTCGACG ATAACGGCGA     540
AATGCATGAT ATCAACGTGA CGGCGTTTAT CGACGTGATG TTGGTTCTGC TGATTATCTT     600
TATGGTGGCG GCACCGTTAG CGACGGTAGA TGTGAAGGTG AACTTGCCTG CTTCTACCAG     660
CACGCCGCAG CCGCGGCCGG AAAAACCGGT TTATCTGTCG GTGAAGGCAG ACAACTCGAT     720
GTTTATCGGT AACGATCCGG TCACCGATGA AACAATGATT ACGGCGTTGA ATGCGTTAAC     780
CGAAGGCAAG AAAGACACCA CCATCTTCTT CCGAGCGGAT AAAACCGTCG ATTACGAGAC     840
GTTGATGAAG GTAATGGATA CGCTGCATCA GGCGGGTTAC CTGAAGATAG GTCTGGTCGG     900
CGAAGAAACC GCCAAAGCGA AGTAAAGTAG AATTGCCTGA TGCGCTACGC TCATCAGGCC     960
TACAAAATCT ATTGCAACAT GTTGAATCTT CGTGCGTTTG TAGGCCGGAT AAGGCGTTCA    1020
CGCGCATCCG GCATTAGGTG CTCAATGCCT GATGCGCTAC GTTATCAGG  CCTACAAAAT    1080
CTATTGCAAC ATGTTGAATC TTCATGCGTT TGTAGGCGGA TAAGGCGTTT CGCACATCA     1140
GGTAAGAGTG AATTCACAAT GATGCCCGGT TGCTTTTCAC AACCGGGCAT TTTTTTAACC    1200
TAAATGCTCG CCGCCGCACA CACCGTGCAC TTCTGCGGTG ACGTAGCTCG ACTCCTGACT    1260
TGCCAGATAA ACATATACTG GGGCCAGTTC CGCCGGTTGC CCCGCACGCT TCATCGGCGT    1320
TTTCTGACCA AACTGCGGGA TCTTATCCTG CGTTTGTCCG CCGGAAATTT GCAGTGCCGT    1380
CCAGATAGGG CCTGGCGCGA CAATATTCAC CCGAATACCT TTCTCCGCGA CCTGTTTTGC    1440
CAGGCCACGG CTGTAGTTCA GAATCGCCGC CTTCGTAGCC GCATAGTCCA GTAAATGCGG    1500
ACTTGGCTGG TATGCCTGGA TTGACGAAGT GGTGATAATA CTTGCACCTT TCGGTAGCAG    1560
GGGGATCGCT TCCTGGGTTA GCCAGAACAG CGCGAAAACG TTAATGGCAA AGGTCTTTTG    1620
AAACTGTTCG CTGGTGAGGT CTGCAATATC AGGAATGGCA ACCTGTTTCC CGGCGACCAG    1680
CGCCATAATA TCCAGCCCGC CTAACGCCTT GTGCGCTTCG TGAACCAGCG AACGGGCGAA    1740
TTTCTCATCG CTTAAATCGC CTGGCAGCAG AACGGCTTTG CGTCCGCATT CTTCAATGAT    1800
CTTTTTCACA TCCTGAGCGT CTTCTTCTTC CACGGGAAGA TAACTGATCG CCACGTCAGC    1860
CCCTTCACAC GCGTAAGATG GCGGCAGCGC GACCGATTCC GGAATCGCCC CCTGTCACCA    1920
GTGCTTTACG ATCTTTCAGG CGACCGCTAC CAACATAGGT TTTCTCGCCG CAATCCGGTA    1980
CCGGTGTCAT CTTCGCCTGG ATGCCTGGCG TCGGTTGTTT CTGTTTGGGA TATTCACCAG    2040
```

```
TGTAATACTG CGTGGTCGGG TCTTTTAAAT GAGACATCGT TTTTCTCCCT TCAGGTTCAA    2100
CGTCCTTTAA GGGTAGACGC TCTCGATGCG TTGATAAGGG AACCAGGAAG ATCCCTAACC    2160
CTCAGAATTA TGCGACAAAG GTTAACGGA  TATGTTGATT TGCTGTTGCG CGCTGTTTAC    2220
TCAATTGCGA TATACTGTTG CCCGTTTTAA CTACACGACA GGAATGTATG AACGTTTTC     2280
TTGAAAATGC AATGTATGCT TCTCGCTGGC TGCTTGCCCC CGTGTACTTT GGCCTTTCGC    2340
TGGCGTTAGT TGCCCTGGCG CTGAAGTTCT TCCAGGAGAT TATTCACGTA CTGCCGAATA    2400
TCTTCTCGAT GGCGGAATCA GATTTGATCC TCGTGTTGCT GTCGCTGGTG GATATGACAC    2460
TGGTTGGCGG TTTACTGGTG ATGGTGATGT TTTCCGGTTA TGAGAATTTC GTCTCGCAGC    2520
TGGATATCTC CGAGAACAAA GAGAAGCTGA ACTGGCTGGG GAAAATGGAC GCAACGTCGC    2580
TGAAAAACAA AGTAGCAGCG TCGATTGTGG CAATTTCTTC CATTCACTTA CTGCGCGTCT    2640
TTATGGATGC GAAAAATGTC CCTGATAACA AACTGATGTG GTACGTCATT ATCCATCTGA    2700
CGTTTGTGCT CTCTGCATTT GTGATGGGCT ATCTTGACCG ACTGACTCGT CATAATCACT    2760
GATCTTATGC GGGCGCGGTT CTCGCGCCCG TTATTAACAG GTCATTTATC GGAAGACGCC    2820
TGCCACAGAT TCAGCTCGCC ATCGGCGATA TGCTGATCAA TCTGCGCCAG CTCCTCGGTG    2880
CTAAATGTCA GATTATTCAG CGCCTGCACG TTCTCCTCAA GTTGTCCGCG CGGCTGGCAC    2940
CAATCAATAC CGACGTCACG CGATCATCTT TCAGCAACCA GCTTAACGCC ATTTGCGCCA    3000
TTGATTGTCC ACGCTGCTGT GCCATTTCAT TCAATAAGTG TAGGCTGTTG AGGTTGGCTT    3060
CGGTAAGCAT TTCGGCGTC  AGACCACGAA CTTTATTCCC TTCACGATGC ATCCGTGAAT    3120
CTTGCGGAAT GCCGTTGAGA TATTTTCCGG TCAGCAATCC CTGAGCCAGA GGAGTAAAGG    3180
CAATACAGCC CACGCCGTTA TTTTGCAGGG TATCCAGCAG GCCGCTTTTA TCCACCCAGC    3240
GGTTCAGTAA ATTGTACGAA GGTTGATGAA TTAACAGCGG AATTTTCCAC TCGCGCAGCA    3300
ACTCAACCAT TTTTTGCGTC CGCTCTGGCG AGTAAGAGGA GATCCCGACA TAAAGCGCCT    3360
TACCGCTTTG TACCGCATGA GCCAGCGCAG AGGCGGTTTC TTCCATCGGC GTATTTTCAT    3420
CGACGCGATG AGAGTAAAAG ATATCGACAT ACTCAAGCCC CATACGCTTC AGGCTTTGGT    3480
CGAGGCTGGA GAGCAGGTAT TTACGTGAAC CGCCAGAGCC GTAAGGGCCG GGCCACATAT    3540
CGTAGCCAGC CTTGGTAGAG ATAATCAGTT CATCGCGATA AGCGGCAAAA TCCTCCCGCA    3600
GCAGGCGACC AAAGTTCTCT TCTGCGCTTC CTGGAGGCGG CCCGTAATTG TTGGCTAAAT    3660
CAAAGTGCGT AATGCCTAAA TCAAACGCTT TACGCAGGAT TGCACGCTGT GATTCCAGCG    3720
CGTTAACGTG ACCGAAATTG TGCCATAAAC CGAGCGATAA CGCGGGCAGG CGTAAACCAC    3780
TTTTTCCGCA ATAGCGGTAC TGCATCTGCC CGTAACGTTC GGGTTCGCTA ACCAGACCAT    3840
GACCTCTCCT TTCCACCGTT CAATTTCGAA ACAATGTTTC TAGTTTAGCG ATTCGCCAGC    3900
GCGTATCCCG TAGTCTGGCT CACAGAGTGA CGAAAAATTG GCAAAAACAC GCGCTTATGC    3960
TTTGCTTAAA AAAACACCAG TTGAGGAGTG CAACGATGCC GCGTTTAACC GCCAAAGATT    4020
TCCCACAAGA GTTGTTGGAT TACTACGACT ATTACGCTCA CGGGAAAATC TCGAAACGTG    4080
AGTTCCTCAA TCTTGCGGCG AAGTATGCGG TGGGCGGGAT GACGGCATTA GCGTTGTTTG    4140
ATTTGCTCAA GCCAAATTAT GCGCTGGCGA CTCAGGTAGA GTTTACCGAC CTGGAGATTG    4200
TTGCTGAGTA CATCACGTAT CCTTCGCCAA ATGGTCACGG CGAGGTACGG GGTTATCTGG    4260
TGAAACCCGC AAAAATGAGC GGCAAAACGC CAACCGTGGT GGTGGTGCAT GAGAATCGTG    4320
GACTGAATCC GTATATCGAA GATGTGGCAC GGCGAGTGGC GAAGGCGGGG TATATCGCCC    4380
TGGCACCTGA CGGCTTAAGT TCCGTTGGAG GTTATCCGGG AAATGATGAT AAAGGTCGTG    4440
```

| | | | | | | |
|---|---|---|---|---|---|---|
| AGCTGCAACA | GACAGGTTGA | TCCAACCAAA | CTGATGAATG | ATTTCTTTGC | CGCAATTGAG | 4500 |
| TTTATGCAAC | GCTATCCGCA | AGCGACAGGC | AAAGTGGGTA | TTACCGGATT | TTGCTATGGC | 4560 |
| GGTGGCGTAT | CGAACGCGGC | GGCTGTCGCG | TATCCGGAAC | TGGCCTGCGC | GGTGCCGTTT | 4620 |
| TATGGTCGTC | AGGCACCCAC | TGCCGATGTG | GCGAAGATTG | AAGCGCCTTT | ACTACTCCAC | 4680 |
| TTCGCGGAAC | TGGACACCCG | AATCAACGAG | GGCTGGCCTG | CTTACGAGGC | GGCGTTGAAA | 4740 |
| GCCAATAATA | AGGTTTATGA | GGCGTATATC | TATCCGGGGG | TTAATCACGG | ATTCCATAAT | 4800 |
| GATTCCACGC | CCCGTTATGA | CAAATCTGCC | GCCGATCTTT | CCTGGCAAAG | GACACTGAAA | 4860 |
| TGGTTCGATA | AATATCTCTC | CTGATAGGTT | TATCTCTTAC | GGGATTACGT | CTTAAACAAG | 4920 |
| CATGAAAAAA | TAGCGTGCGC | AAAAGTCGTT | CTTTGCCTAA | AATATCGCTA | TATATAACAA | 4980 |
| TATATAGCGA | ATGAGGTGAA | CGATGAATAA | CCATTTTGGT | AAAGGCTTAA | TGGCGGGATT | 5040 |
| AAAAGCAACG | CATGCCGACA | GTGCGGTTAA | TGTGACAAAA | TACTGTGCCG | ATTATAAACG | 5100 |
| CGGTTTTGTA | TTAGGCTACT | CACACCGGAT | GTACGAAAAG | ACCGGAGATC | GCCAGCTTAG | 5160 |
| CGCCTGGGAA | GCGGGTATTC | TGACGCGCCG | CTATGGACTG | GATAAAGAGA | TGGTAATGGA | 5220 |
| TTTCTTTCGT | GAGAATAATT | CCTGTTCTAC | GTTGCGCTTT | TTTATGGCCG | GTTATCGCCT | 5280 |
| CGAAAATTGA | TCAAACATAC | GTATTATCTT | GCTTTAATTA | ATTACACTAA | TGCTTCTTCC | 5340 |
| CTTCGTTTTA | GCGCCCCGCC | GCAGTATCAT | GATATCGATA | ACCATAATAA | ATGTGTGGTA | 5400 |
| AATGGCGCAT | CGATCGCATT | ATTGATTTTG | CGATTGAGGC | AAAATATATG | CCAGGTCTTC | 5460 |
| GCAACGGAAT | AACTATAAAT | GACTGGAGAT | AACACCCTCA | TCCATTCTCA | CGGCATTAAC | 5520 |
| CGTCGTGATT | TCATGAAGCT | T | | | | 5541 |

( 2 ) INFORMATION FOR SEQ ID NO:21:

( i ) SEQUENCE CHARACTERISTICS:
     ( A ) LENGTH: 6317 base pairs
     ( B ) TYPE: nucleic acid
     ( C ) STRANDEDNESS: double
     ( D ) TOPOLOGY: linear ( i i ) MOLECULE TYPE: Genomic DNA ( v i ) ORIGINAL SOURCE:
     ( A ) ORGANISM: Enterobacter cloacae
     ( B ) STRAIN: Clinical Isolate ET- 12

( x i ) SEQUENCE DESCRIPTION: SEQ ID NO:21:

| | | | | | | |
|---|---|---|---|---|---|---|
| AAGCTTGCCC | GCATCATTCA | GGAGCAGGGG | CGTCGCGACC | AGTTAGGTGT | GAAGTTTGGC | 60 |
| AGCGGTGACA | GCCCGGACTG | CCGGGGGATC | ACGGTTCCGG | AACTGCAGAG | TATCGACTTC | 120 |
| GACAAAATCA | ACTTCTCTGA | CTTCTACGAG | GATTTGATGA | AGAACCAGAA | AATCCCCGAT | 180 |
| ACCAGCGCGC | AGGTCAAGCA | GATTAAGGAT | CGCATCGCCG | CGCAGGTGAA | CCAGCAGGGA | 240 |
| GGTGGCAAAT | GAAGCGTGTC | CTCTGTGGCC | TGCTTATGGC | GCTGGCGAGC | CATACGGCAC | 300 |
| TGGCCGATGA | GATTGTGACG | CCGGCTGAGC | CGTTCACCGG | CTGGTCCTGG | TACAACGAAC | 360 |
| CGAAAAAGCC | CCCTGAGCAG | CCCCGGAAAC | CGCAGCAGCC | AGCACCGCAG | CCATTCCGGA | 420 |
| TCTCAGCAAA | ATGTCCCCGA | TGGAGCAGGC | CAGGGTGCTG | AAAGGGTATA | CACAGGAGGC | 480 |
| GCTTAACCGC | GCCATCCTGT | ACCCCTCAAG | GGAAAACACG | GCGACGTTCC | TGCGCTGGCA | 540 |
| GAAGTTCTGG | ACGGACCGGG | CATCGATGTT | CAGCCAGTCC | TTTGCGGCGG | CGCAGCTGAG | 600 |
| CCATCCGGAC | CTCGACTACA | ACCTGGAGTA | TCCGCACTAC | AACAGCATGG | CGCCGTTTAT | 660 |
| GCAGACCCGT | GACCAGCAGA | CGCGGCAGAG | CGCCGTGGAG | CAGCTTGCGC | AGAGTACGGT | 720 |

| | | | | | |
|---|---|---|---|---|---|
| CTGTTCTACT | TCTACCGGGG | CAGTGACCCG | ATTGATGTGC | AGATGGCGGG | CGTGGTGGCT | 780 |
| GACTTTGCGA | AAACCAACGG | GATCTCACTC | ATTCCGGTCT | CGGTTGACGG | ACAGGTGGCG | 840 |
| GCCACCCTGC | CGCAAAGCCG | TCCGGACACC | GGACAGTCCC | GGTCGATGAA | TATCACGCAC | 900 |
| TTTCCGGCGC | TCTTCCTGGT | TGACCCGCGC | AACCAGAACT | ACCGTGCCCT | GTCCTATGGC | 960 |
| TTCATGACCC | AGGATGACCT | GTCAAAACGA | TTCCTGAACG | TGGCCACCGG | CTTTAAACCC | 1020 |
| AATTCCTGAG | AGCCTTTTAT | GACAAAAACA | CTGTTTACCT | CATCCGCGAT | GCAGGGCGGG | 1080 |
| CTGCCCTGTA | TTCCTTCGTC | CTCGGCCCGG | CACTGGTGCT | GTATGTGTTT | GTGATGCTGG | 1140 |
| CGGCATCAGA | CGGCTCACTT | TCCCGGCAAT | TCCTGACGAC | CTTTCATCAC | CTGACTGAGG | 1200 |
| GTGCGCCTGC | CGGCAAGGTG | ATGGGATGTG | TTAATGAACA | TGAGATGGCA | GGGCGTTTCT | 1260 |
| CGCCACCTGA | ACCCGGAGAG | TCGTTAAAGC | CCGTGCCTTC | CGTTTTAGAT | AAAGCACCGC | 1320 |
| CTGAAGTGTT | ATGTCAGCTC | GGGCCCGTTG | ACAGCGATTC | GTGGGCGCGT | ACGACAGATG | 1380 |
| CAACGTTGCT | CAACACCTGG | ATTATCTCGG | TGATGTTTGG | CTTTGGTGTG | TGGTTTGTTT | 1440 |
| TATATGGCCT | GTCCGGGCC | GCTCAGCGTC | GCATTTCACC | AGACACACAT | TCTGTACTGG | 1500 |
| TACGGCAGAA | CAAGGAGACA | CAGGAATGAA | ACCAACTCTT | CTCGCAGGAC | TGATTTTCTG | 1560 |
| GGGCATGATG | GCGCGCCGTA | CTGAGCGAGC | TGATGACCTG | GTCCGTGGAG | CATACACAGC | 1620 |
| AGGGCCTGCT | GTGGCTGTGC | AATGGGATGT | GGGCCGGGGC | GGCTGGCATG | GTGATTTATG | 1680 |
| CAGGTTATCG | CTGGTACCGT | GACGAAAGAG | GGCAAACGCA | TAAGGAAGGC | GATCATGAAC | 1740 |
| ATTAAAACCG | GACTCACGGC | TCTGCTGATG | TGCCTGCCCC | TGCTGGCGAA | CGCGGGGGCG | 1800 |
| CGCGAGGAGT | TAATGGCGCT | TGAAGCGACA | AAAACAACCT | CTGCTGACGC | TGCAGCCATC | 1860 |
| ACCGCCTCCA | CCATTCCGGT | ACCTGCGCCG | GCCAGCCTGA | TGGCGCTGCC | GGACGGACGT | 1920 |
| CGGGCTAACA | TGAAAGATTA | TGCCGTGGTG | CTTTTTATGC | AGGCACACTG | CCAGTACAGC | 1980 |
| GCGAAGTTTG | ACCCGCTGCT | GAAGGGCTGG | GCTGATGAGC | ATTCTGTCAG | GGTTTATCCA | 2040 |
| TACACCCTGG | ACGGCGGCGG | TGATGTGTCT | TACCGACGCC | GATGATCCCG | CGCAAGACGG | 2100 |
| ACCCGAATTC | TCCCATTGCA | GACGAGATTG | TCACCTTCTT | CGGAAACGGG | CTGCCGATTG | 2160 |
| CGACACCAAC | GGCCTTTATG | GTCAACGTTA | ACACCCTGAA | AGCCTACCCG | CTGACCCAGG | 2220 |
| GTGTGATGGA | CATCCCCGCT | CTTGAGAGCC | GTATGGCCAG | CCTGATTCAG | GCTGACATGG | 2280 |
| ACAACGTCGA | TCCGAAAACG | CTGCCGCCCA | TGCCGGCAAG | TGCGCAGGTC | ACCCCTCAGT | 2340 |
| AATACAAACG | GACTACAAAA | TGACGACAAA | TACGTATGCG | TTATCGCGTA | CCGAGCGCGT | 2400 |
| GTGGCTGTTA | TTCAGCGTGA | CGCTGCTTGT | GTCCGCAGCT | TTCTATGGGG | TACTGGCCCA | 2460 |
| CCGGGTGGTC | AGCGTCTGAC | CGTCAGACTG | ACAACTGTTT | GCAGGACTTT | CCGGTGCTCC | 2520 |
| TGCTTATCTC | GCTGAGTATC | GGATTCTTTT | TCACCGTCAC | CGGGCTGTAC | GTCTGCCGGC | 2580 |
| AGACCCTGGT | CAGGAAACCC | CGGGAGGAGA | TTGCATGAGG | CACATCAGAC | TGAAGACGTT | 2640 |
| TATCCGAAAC | CAGGCTATCG | GGATACTGAA | AGACAGTAGT | GAGGATACGG | AAACCCGAAA | 2700 |
| ATGGACGGAT | TTGTTAACCC | TGAAACTGTT | TTTATGCCTT | AATTTTTACC | GCCGTAGTCG | 2760 |
| AAAGGGTATA | CGTGAAGTGC | GCCATCACAA | CGCTCAGTGC | GATCTCCGTT | GACCGCTCCG | 2820 |
| AACAGTTTAC | GCTCTCGCTT | CTCATCCACT | ATCCACAGTA | CCTGTTGTGG | GGCGTTATGG | 2880 |
| CCGCGATTAT | CGCGCTCATT | GCGGTGAATT | TACTCGTCTG | CGGCTGGTTC | TGTCTGGCCA | 2940 |
| CATATCTTTG | CCGCAAACTG | AACCGGACTG | ACATCCCGGC | AGGCAAGGAT | ATGCAAGCTG | 3000 |
| TGGAGGTGCC | TAATGATTAA | GGCGCTTATT | ACGGCAGGGG | TTGTGTTCTT | CTCAGGTCTG | 3060 |
| GCAGCGCTGC | CTGCTCAGGC | GGACGTCAAT | GGTGACTCAA | CGGCTTCTTT | GGCAAGCTGG | 3120 |

| | | | | | | |
|---|---|---|---|---|---|---|
| GCTACAGCGG | CAACGTCTCT | CAGGCGCAGG | CCTGGCAGGG | GCAGGCGGCC | GGGTATTTCT | 3180 |
| CCGGCGGGTC | GGTCTACCTG | CGAAACCCCG | TCAAAAACGT | TCAGCTGATC | TCGATGCAGC | 3240 |
| TGCCGTCCCT | GAACGCCGGC | TGCGGCGGTA | TCGATGCCTA | CCTGGGGTCA | TTCAGCATGA | 3300 |
| TCAGCGGTGA | GGAAATTCAG | CGATTCGTGA | AGCAAATCAT | GAGTAACGCG | GCTGGCTATG | 3360 |
| CATTCGACCT | GGCACTGCAG | ACGATGGTCC | CGGAGCTGAA | GCAGGCGAAA | GATTTCCTGC | 3420 |
| AGAAGCTGGC | CAGTGATGTT | AACTCCATGA | ACATGAGTTC | GTGCCAGGCC | GCTCAGGGCA | 3480 |
| TCATAGGCGG | GTTGTGGCCC | GTAACGCAGG | TGTCACAGCA | GAAAATCTGC | CAGGACATTG | 3540 |
| CCGGCGAAAC | CAACATGTTT | GCTGACTGGG | CGGCCTCCCG | CCAGGGCTGC | ACCGTCGGAG | 3600 |
| GACAGGGGGA | TAAAGTCACG | GCCAAAGCCG | GCGACGCAGA | AAAAAGACCC | AGGTACTGAA | 3660 |
| AAACAAAAAC | CTTATCTGGG | ACACGCTCAG | TAAGAACGGG | CTGCTTGGTA | ACGATCGCGC | 3720 |
| CCTGAAGGAG | CTGGTCATGA | GTACTGTCGG | CTCCATCATT | TTCAACAAAA | CCGGAGACGT | 3780 |
| GACATCCTGA | CGCCGCTGGT | CGATACCGCG | ACCTGATTAA | AGTTCTGATG | CGCGGGGGAA | 3840 |
| CAGCGAAGGT | CTACGGGTGC | GATGAGGCAA | CACTCTGTCT | GGGGCCTGTC | GTTACTAACC | 3900 |
| TGACGATTAC | TGAGTCCAAC | GCTCTGGTCA | CACTGGTCAA | AAAACTGATG | CTCTCGATGC | 3960 |
| AGAACAAACT | TGTCGATGAC | AAACCGCTGA | CCGATCAGGA | AAAAGGCTTC | GTGAACACCA | 4020 |
| CCTCTGTGCC | GGTACTGAAA | TACCTGACCA | ACGCCCAGAG | TATGGGGATG | AGCGCCACGT | 4080 |
| ACCTCCTGCA | GGTTTCCGAC | TTCATCGCGC | AGGACCTGAT | GATCCAGTAC | CTCCAGGAAC | 4140 |
| TGGTGAAACA | GGCAAGCCTG | TCTCTGGCTG | GTAAGAACTT | CCCGGAAGAG | GCCGCTGCGA | 4200 |
| AGTGCGCGAC | AACATCATTC | ATGCCCAGGG | ACTGCTGGCC | GACATGAAGC | TGCAGTCTGC | 4260 |
| GGCAGACCAG | AACGCACTGG | ACGGCATCGA | CCGCAACATG | CAGTACTGCA | GCAGCAGGTG | 4320 |
| TCCACCATTG | TTTCAGGCTC | CTATCAAAGC | AACTATCACT | GGGGTGATCG | CTGATGCTTG | 4380 |
| AGATATACAC | CATTTATGGC | GGGGGAATGT | GGAAAACGC | GCTGGACGCC | GTTGTCACCC | 4440 |
| TTGTCGGTCA | GAATACCTTC | CACACCTTAA | TGCGTATTCG | CCCGGCACCT | TCGGGGTGCT | 4500 |
| GGCTGTATTG | CTCACTTTCA | TCAAACAACG | TAACCCGATG | GTCTTCGTCC | AGTGGCTGGC | 4560 |
| GATCTTCATG | ATCCTGACGA | CCATCCTGCT | GGTACCGAAA | CGTTCAGTAC | AGATAATTGA | 4620 |
| CCTCTCAGAC | CCCGGCTGCG | GTGTGGAAAA | CCGATAATGT | ACCGGTCGGT | CTGGCTGCCA | 4680 |
| TCGCGTCACT | GACGACCAGC | ATCGGTTACA | AAATGGCATC | GGTGTACGAC | ATGCTGATGG | 4740 |
| CCAGACCTGA | CTCGGTAACC | TACAGCAAGA | CCGGTATGCT | GTTTGGCTCG | CAGATTGTGG | 4800 |
| CGGAAACCAG | TGACTTCACC | ACGCAAAACC | CGGAACTGGC | TCAGATGCTG | CCGGACTACG | 4860 |
| TGGAAAACTG | TGTGATCGGC | GACATTCTGC | TGAACGGTAA | ATACACCATC | AATCAGCTGC | 4920 |
| TCAATTCCAC | TGACCCGCTG | ACGTTGATAA | CCAGTAACCC | AAGCCCGCTG | CGGGGCATCT | 4980 |
| TTAAGATGAC | CTCCACCTCG | CGCCAGTTCC | TGACCTGTCA | GCAGGCGGCA | ACGGAGATTA | 5040 |
| AGACGCTGGC | GAATACCGAC | GTCAATCCGG | GCAGTGCGAC | GTTCACCTGG | CTGACGCGGA | 5100 |
| AGGTATTCGG | CAACAAGCTG | AATGGTGCCT | CGCTTCTGCC | AACGCTATGG | GTGAGAGCTA | 5160 |
| CGGATTCTTC | TATGCCGGGG | GAATGACGGC | TGCGCAGATC | ATGAAGAACA | ACATCACGAA | 5220 |
| CAGTGCAGTT | CGGCAGGGGA | TTAAGGGTTT | CGCCGCTCGC | TCATCCGACA | CGGCTAACCT | 5280 |
| GCTGAACCTG | GCCACCGAGA | ACGCTGCAAC | CAAACAGCGT | CTCAGCTGGG | CTGCGGGTAA | 5340 |
| TGAGCTTGCC | ACCCGAACTC | TGCCGTTTGC | ACAGTCCCTG | CTGATGCTTA | TCCTGGTGTG | 5400 |
| CCTGTTCCCG | TTGATGATTG | CGCTGGCCGC | ATCAAATCAC | ACTATGTTTG | GGCTGAACAC | 5460 |
| CCTGAAAATA | TACATTTCCG | GTTTTATCTA | TTTCCAGATG | TGGCCGGTGA | TGTTCGCCAT | 5520 |

-continued

| | | | | | | |
|---|---|---|---|---|---|---|
| CCTTAACTAT | GCTGCCAACT | ACTGGCTGCA | GAGTCAGTCC | GGGGGCACGC | CTCTGGTGCT | 5580 |
| GGCCAACAAG | GATGTAGTGG | CACTGCAGCA | TTCGGACGTG | GCGAATCTGG | CAGGGTATCT | 5640 |
| GTCGTTGTCC | ATTCCGGTGC | TGTCGTTCGT | ATCTGACCAA | GGGGGCTGCG | GCGATGGGCT | 5700 |
| CTCAGGTGGC | AGGCAGTGTC | CTCAGTTCGG | GCGCCTTCAC | GTCGGCAGGT | GTGGCAGCAA | 5760 |
| CCACGGCGGA | CGGGAACTGG | TCGTTTAACA | ACATGTCAAT | GGACAATGTC | AGCCAGAACA | 5820 |
| AGCTGGATAC | CAACCTGATG | CAGCGTCAGG | CCAGCAGACG | TGGCAGGCAG | ATAATGGTTC | 5880 |
| CACGCAGACG | CAGACGCCGG | TGGCCATACG | GTATCGACGG | CTCAGGCGCA | ATGTCGAATC | 5940 |
| TGCCGGTGAA | CATGAAGCTC | AGCCAGCTGG | CCAGCAGTGG | TTTCCAGGAG | TCTGCCCGCC | 6000 |
| AGTCGCAGGT | CCAGGCGCAG | ACGGCGCTCG | ATGGCTACAA | CCACAGTGTC | ACCAGTGGCT | 6060 |
| GGTCGCAGCT | CTCACAGCTG | TCTCACCAGA | CCGGTACCAG | CGACAGCCTG | ACCAGCGGCA | 6120 |
| GTGAAAACAG | CCAGGCCACT | AACTCAACGC | GCGGCGCGAG | CATGATGATG | TCGGCCGCTG | 6180 |
| AAAGCTATGC | GAAAGCTAAC | AATATCTCGA | CGCAGGAAGC | CTATAACAAG | CTGATGGATA | 6240 |
| TCAGTAATCA | GGGTTCTGTA | TCTGCAGGCA | TTAAAGGTAC | GGCCGGAGGG | GGACTTAATC | 6300 |
| TGGGCGTTGT | TAAGCTT | | | | | 6317 |

( 2 ) INFORMATION FOR SEQ ID NO:22:

( i ) SEQUENCE CHARACTERISTICS:
        ( A ) LENGTH: 6914 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 49

( x i ) SEQUENCE DESCRIPTION: SEQ ID NO:22:

| | | | | | | |
|---|---|---|---|---|---|---|
| AAGCTTTTCG | AGTTCGCCAT | CCGGCAACAG | CTCACTGAGC | TTTTACGCGC | CAGGGTGCC | 60 |
| TTTGAACTCA | ATTCCCAGCT | CAGTAAGGCG | GTCCTGAATA | ATCTCTTTGC | GAGATTTTTC | 120 |
| ACTGGTACCG | GCATCAGGTG | TTGCAGGTTT | CAGCTCGCCA | CCAGCCTCGC | CCTTCATCAG | 180 |
| CCGGACGTTA | GACTTCAGCG | CCGGGTGAAG | ATCTTTCAAC | TCCACCACGT | CGCCAACCTT | 240 |
| TACGCCGAAC | CATGGGCGCA | CAACTTCGTA | TTTAGCCATG | CTGTTTCCTT | ACGCCAGGTT | 300 |
| AGCGCCGTAG | ACAACGCCAG | ACAGGCCTGA | TCGTCTGCAG | TAATTTGCAG | GCCTTCAGCA | 360 |
| GACATGATCT | GGAAGTTGTA | GTTAACGTTA | GGCAGTGGGC | GCGGCAGTGG | CACAACGCCA | 420 |
| ACAGCCATAC | CCACCAGTGG | GGAGATCACG | TCACGACGAC | GAACGTACGC | GATAAACTCG | 480 |
| TTACCGGTCA | GCGCGAAGTC | ATGCGGATTT | CTTTCACCGG | TGCGAATGGC | AGAACAGCCT | 540 |
| GCAGGAGAGT | GCCGCTCACC | ACACCATTAA | CTACGTATGG | CTGAGCCATA | TTTGCCCAGA | 600 |
| TCTCAGGGGA | AACCCACATC | ACATCATACT | GAGCTACTTT | GTTGGTGCGT | GCGGTGGTAC | 660 |
| CGAATGCTCC | TTTACCAAAG | AACTCAAAAT | ATTGAGTCGT | GGTTGCGCTG | GTCAGGTCGA | 720 |
| TGTTCGCACC | ACCAGCACCA | GAACCGAGGT | TAATCTTCTT | GGTGTTGCGG | TGGTTCTTGA | 780 |
| TGCCCTGCGC | CGGGTAGGAC | TGAACCTGAA | TTTTTGAATC | GCCGTTCAGG | TAGTAGTTGA | 840 |
| CGCGCTTCTG | GTTGAACTTG | CGCATCTTCG | CCATCTGCGA | ATCCAGAACC | AGATCAATGC | 900 |
| CTACAGAGTT | AAGGCCAGCA | GCATGACGCC | AGTTAACACC | GTAGCCAGCA | GTGAACACCG | 960 |
| GAATCGGGTC | GCCATCGCTC | GCGTAGTCAG | TGTGGTCGAA | GGAGAATGGC | GCCTGACCAT | 1020 |
| CGATGCTTAC | TGACACGTCG | TCAGCGATGT | CGCCGACCAC | GTTATACAGC | TTGGCGGTTT | 1080 |

-continued

```
TACCAACCGG CAGCACGGTC TGAACGCCGA TCAGGTCGTT TACGATTTCC ATGCCAACTT    1140
CCTGATCCCG CAGCTGCAGC ACCTGGTTGT CAATCTCAGC CCAGAAGTCA CGGGAGAAAC    1200
CGCCAACAGC GTTACAAGCC AGCATGTCAG GCGTCATCAT TGCGCGGTTA GCTGCAATGA    1260
TGGAATCGTT CTGTAGGTTC CACATGTTGC GGTTGCCCA  CAGCTCACTC CAGTGCCCGC    1320
CGAGGCGGGA GTTAGTCGCC AGCGTCTCTT TAGAGAAGTA CATATGTGTT TGTCCTTTTG    1380
TTACGCGCCA GCTGCGGCGA CAGTGCCAAC GCGCATACGC ACGCGAATGA AGTCAGTGGT    1440
GCTGGCCGCG ATGGTGTATT CATCCTGGCT GTAGCCGATC ACTGAATCAG TGTCGGATGT    1500
GGCAAGGGTA AACTGACCGG CAGTTCCCAG CTTGATCGGG CTGTCTTTTT TATACGCACC    1560
AGGCAGGCAG CGCAGCGCCA GCTCACGACC TTCTTCGACG TAGTTACCTA CTGCCGAATC    1620
CCCGGCAGGG ATTTCTTCGG TGATTGTCAG GCCCTGGTGA TAACCGACAT CGATGATGTA    1680
CAGGCGGCCG GTTAGCGCGG TGGCCTGAGC GAATTTATCG GATGAGTTGA TGGTTGCGGC    1740
GGTGCCAGGA AGCAACCCGG CGGCCGTTGT GCGGGTTTCG GTCTTGTACA GAGACTGACC    1800
GTCGATATTA ACGCGACGAT AACGTGGCAT TATTCCGGCT CCTTACTTGA AGTGTTCGTC    1860
TGCGGCTGGT GCGCCGGTTT CTTTGTGCTG CTGAGCATTG TTGGTGCCCA GCGACTTGAA    1920
CATCGCGTCC AGAGCTTCGC CTGACAGAGC GTTCGCGAGC GATATCGCCA TGGACCTTCG    1980
CAACCGCTTC GCGCTTTGCT TTCTCTTCGG CACGGGAGTT CGCGGTAAGG GTTCCGCGA     2040
GTTGCTTCTG ATTGGCCTGC AGCGCATCAA CCTTTTCCGC GAGAGGCTTA ATAGCCGCTT    2100
CAGTATTGGT CGCAACAGCC TGGCCGATCA TGCTGCCGAT TTGTTCCAGT TCTTCTTTGG    2160
TTAAAGGCAT GTCGCCTCCG TTTTGTGGTT TGGTGCAGGC TGTTCCTGCG GTGTGAATAG    2220
AGCTTTGAAT TGTTAGCGAC GACTGCCACC CACGACTCCT GGCGCGCTAC TGCGGTTCCG    2280
GTATCGTCGA TTGTGATCTT CCCGCCATCA GCGAATACCG TAAACCTGAG CATCACCGCC    2340
ATTTCGCACG ATGACCACCT GCGAGTCAGT GAGTCAGCAA CCCAGGCATA TTCATCCGTG    2400
CCCGGCGCAA ACTTGGCTTT GGCTGCCCGA TCGAGACGCT GCTCGCGCTC CCGGTAGGAT    2460
TCACCCACCA GCGCGCCGGA GTTCGCTTTA AGCGGCTGCG CCAGATCGGC GTTTACCATC    2520
AGGCCAACGC CCTGCTCAGG GGTGGCGGCT CCGACTTCGT GCAGTAGGAT CGCGTCGTGG    2580
TCCATGCTGT GAATCTTCGC CACCCACTCG GCACCCGTAG CTCTCTGTTG TTCGTTAGGC    2640
TCAAGCTGGT CGAGGAAAGC GGCGACACTG GTATGAATCG GCGGAACGTC ATCGCCGCGC    2700
TCGATGGCTG CGACGCGCTC AAGTAGTTCT CGGCCACCTT CAGACTCACC GGCGCGGGCA    2760
ACATCAACCC ACTTTTCGAG GTAGATACGA TTACCGGACT TCTTAACGTT GCGGTTCCAC    2820
GCGCCGATAT GGCCTGCGTT AATCCCCTCC GGGGAGAAAG CAGACACGAA CTGACCATTA    2880
ACCTGAGGGT GGCCCAGCGG CGCCAGGGTA CCTTCCAGCC CCTTATAGTG GGCGTCGATT    2940
TGCTCTTGCG TGTACAAGCC GCCATTCATG ACGACGTTAG CTGGAAGTGT GTAGCTCGGC    3000
AGCACCAGGT GCTCACGCCC GTTGTATGTT TCGCGCCGGA TAGACTGGCT GTTCACCTTT    3060
GTGGTGATGT TGACCTGAAT ATGCTCACCA TGTTTCGGTG CCTGGATTGG ACGCTGTGCT    3120
TCGTGGTTTA CCTGGAATTT CATGAGTTAT TTCTCCGCCC AGGCGTAACC GCTCGCCTGC    3180
ATCGATTTAT ATTCCTGTTT GAGTTTCGTG ATGGTGTCCG GGTATTCCGG CTTGCCGTCC    3240
GCATCCACCA GCACCGACTG CTGGCTGCAT TGCAGTTGA  TGGAGTTGCC ATCTTTGCTG    3300
TACCAGTCAC GCACCTCTTC GTTGGTGTAG AGGTGGGCAT GGGCGCACTG CGTGGGTATG    3360
TCGCGTTGTC GGCGACAGAG CTGAGATGTG AACCAGCAGC GTTTAAGGC  CGAACAGGTC    3420
ATTCGCCTCT TGGTCTTCAT CCCACTTGGC CCGGCGCAGC GCGGTAGTCA CTTCAGTGCG    3480
```

-continued

```
TGCTATCCGG TTAGCCCGGC GTTTCTCGAT GCCGGTCTGG TCTGTCAGGT TGCGGGCAAT   3540
GTCCAGAGGA TTGAGCCCGC GCCCAACACC ATCAGTAAGA CACGCGCCAT GTCGCGCTTA   3600
ACGTCAGCCG TCAGCCCCTT CATTTCCTCA AATACACGCG CATGCACCAG CGCCATGCGT   3660
TTCTGATACT GGTCGCTTGC GAGGATGGAG GCCAGCGACT CACGCCCGGC TGCGTACACC   3720
GGGGATTGCT GACTGAGGTT GTAGAACGAC TGCCCGGTCC CTTTTCCGA AGCCAGATCG    3780
ATGTACTCGT AAAACCACAG GTCGTAATCG CCACCTTCAA GCAGTACCTG ATCAACCAGG   3840
TAACTGGCAT CGTTCAGGAT GATGGAGAGT AGCATTGGGT TTAGCTGGTA TTCGTATCTG   3900
GCGTTACTG CGAGGGAGGA AGGTATTTTG TTGAGTGCTG ATTTGTACGC CTTGCCAATC    3960
TTATTCATCC GCCTGGCGAA GTCTTTCATT GCCCGGCGTT CCAGCGCATC GGCTCCGGTC   4020
GGATCCTGAT AGTTACGCGG CAGAATCGGT GGCTTCGTCT TCTTCGTCGC CATCCTCTTC   4080
TCCTAATGGA AATTCATCGA CGTTTTCATA ACCGGCAGCA GTGCGGAATT TCTTCACGAC   4140
TAAAGGCTGG TTTTTCTCCG CTCCCCTGGA ACGTCTGGTT AATCTCTGCC ATGGTTTTGG   4200
CATTTGCGAG TTTCTCAGTT CCAGTCTGTT CGTTGAGGTC ATCCCAGATA ACCGTCTTCT   4260
CGCTGACTGC ATCAATAATT TTCAGGTCGA TGAGCTTGTC ACTGAAGTCT TCAATTTCGA   4320
ATGACAGGTC ACCGCGCCGT GACTGGCAGC GCGCGTTGAA ATATTTCTGA TCCTCGGTGC   4380
TTGCCCTTTC ACCCGTCTGC ATCCCAACCA GAACCTTCAC AGGGATATCA ACAGATGCAG   4440
CGAAGGTTTG CAGGTTGACG TTATAGGTCG CTGACGGATC CGCTACAGCT GTGACCAGTG   4500
GTGTGACTGT AGCCCCTTGG GTTGTCATCA GAACATCGTT ACCACGGTTC ATTCCCCGG    4560
CAACTTCGTT AAACTTATCC TGCAACTCGT CCATGTCACG CCATAAAGTG ACGCGAGATT   4620
GTTGAAATCG ATTTCCTTCT CAAAGTTGAC ATTAAGCTGC CGCGCGGCGT TCTTTAGGAA   4680
TGACTCACCA GAACCACCCT CGACCTTCTC AAGGCTGACG CAGGCGTTAT AGCCAGGCTC   4740
AAGGAAGCCA ATAGCATCAT TAGAATAGTC ACCAAGGATA AAGACGCGAT CGGGATGTAC   4800
GAAGCGCTGA TTAGTTCCAC CGCTTGGAAG GCTCTCAACA TATTTCCACT GCTTTGGCTG   4860
CCCGTAGCCT GCCGATTTCT GGTCAGTTAC CCACTCGCTG ACTGTTAATG ACCCAGCCCA   4920
TGCGATCGTA ACCTTTTTTA GTGACTTGCC ACGAACAACA GGCTGATCCC ATGTTCTGGA   4980
ATCATTGATA TGCAGCAGGA TACCCGCATA ACGTCCGACC TGTCGGCGGC GGTCTGCTTC   5040
AGCAAAAGCC CGCCAAAGGC GCTTTGTGAA AACCTTTTTG GTGTTCTTCT CCCAGGCAGT   5100
TTCATCCTTA CTCTCGTCGG CATCATCACC CTCGATGATT TCCGGGTTGG TCTGCCAGCA   5160
CTTGCCCACC AGCTTCTCTA CTGCGCCGTG GGCTATTCCA CCGCGACGAT ACAGTGCGTA   5220
GAGGTTTTCG TAAGTGACCT GCTCAGGGAA TCCATACTCG CACCATGCGG AATGGCGCTT   5280
ATTGTCCAGC CCCATTGTAG GCGCCAACAG CCCCATACGG GCACGGGCCA TCCGCGCATC   5340
GTTCAACGCA TGGTTGACGG CGAGAGTTAA TTTGTCAGTC ATGGTTTGTC CGTTGGTGGA   5400
TTTAAGGCAT AAAAAAGGC CGCTTTGGCG ACCTTGTGGC TATTTAAAAA GCTAAACTCT    5460
GTTGAACGAA ATAAACATAA TCTGCTCAGG CTTAACGCCA TAATCACTTG CCAACTTCTG   5520
AGTGCACTCA ATTAAGACAG TTGATGCAGA TTTCGAAGAG CTTGCACCAT AAATTTCGAA   5580
GTTTCAAAT ACTCCGCCGT TGGTGTGGTA AATCTTATAT GACATAAACC AATCATTCAT    5640
AATATCTACT CCCTTACAGA ATTGAGTAGA TATTATCGGC AAGTGCATAT GTTTCTTTAA   5700
ATTATCTCAA CCTTTTCGGG ATCATCATCC CGGCCATCTG GCCCTTACGT TAATGTGTC    5760
CGTCGAGGCT GTAGCGAATA CCGTCCCAGC AGTGTTCGTA ACCGTCTGCC AGTTTAGGCA   5820
ATACCTCGCC GGTGATGCGG TCCGTTTTGT AGGACCACAT GCGGGCCTCT CTCGCCACAT   5880
```

```
TCTTGCAGCG  AGGATGGATA  ATGATTTCGT  CAAAGCCGCG  AAGATGCGCG  ATACCGTCCT    5940
CAACACTCCC  CTGCCATTTC  TCGGCAGCCG  AGATGTTGAA  GCCCTGGCGC  TTGAGATAGC    6000
TGATAGTCTC  GGGTCGGGCG  GAGTCGGCCT  TGATGGGCCA  GTCACGCGAT  CCGGGGATTG    6060
TGTCGTATAG  CTCTGGCATA  TGGTCGAGCT  CTGTCTGCTG  ACCGTATGCC  TCGTATTCGA    6120
TGTACAGCCG  GTTGTGCAGG  ATGAACGAGC  GCACCAGCGT  GTTAGGGTCT  TGGCGAAAC     6180
CGAAGTCAGC  ACCGAAGAAA  AGGCGATCGG  CCTCTTTCCA  TAGCTGGTCC  GAGAACTCAG    6240
CGATCCGGTA  TTTACCGGCC  AGCACCTGCT  TATCAGAGTT  TTCGAGGTAA  GCACCTTCCC    6300
AAACCCACGC  GTATGTTGCC  GGGTCAAGGC  GGCGCTGATC  GTTCTGTCGC  TCACCTTCCA    6360
GCACGTCGGG  GAACCATGGA  TTATCCGTGT  AGTTCATCTC  AACGTGATAC  AGTCGTCGCC    6420
AGCCTCTTTA  CGGAAACGCT  TATCCGTGCG  CTGCCGTCGC  GCTCCGGGTT  CCATGTCACC    6480
CAAATCTCTG  AACCTTCCTC  ACGAACGGTC  GGGCTCAGCT  TCTGCCAGGC  TATTTCGCTG    6540
ACTGATTCAG  CCTCATCAAC  CCAACAGAGC  AAGATGCGCG  CTTTCGACTT  GATGCTGTCG    6600
AGGTTATGCC  GCAGACCGCA  GAACACGTAG  TTAACGCTCT  TGTCGATGGT  GCGGATGTAC    6660
TTCTCGCCGA  TATCAAAGTT  GGAAGCCAGC  CAGGGAACAG  ACAGGATAGC  CTGTTTCACC    6720
TCCTGCATAC  TCGACTCTTC  CAGTGAGTTC  ATGAATTCAC  GCGCACAGAG  CACCACGCCG    6780
CTTTCACCGT  TCATCATCGA  CTGATACGCC  TTTACGGCTG  TCATCAGCGC  AAAAGTGCGC    6840
GTCTTGGCAC  TACCACGCCC  ACCATGCGAG  CACCGGTAAC  GCTTATTCTC  GGCGATGAAC    6900
AGTGGCGCAA  GCTT                                                         6914
```

( 2 ) INFORMATION FOR SEQ ID NO:23:

( i ) SEQUENCE CHARACTERISTICS:
        ( A ) LENGTH: 5975 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Klebsiella pneumoniae
        ( B ) STRAIN: Clinical Isolate KI- 50

( x i ) SEQUENCE DESCRIPTION: SEQ ID NO:23:

```
AAGCTTATTC  CACGCTGGAG  GCGTCCGGGA  TTATCGGCGT  CAACGCTATC  GCCGGCATCG     60
CCGGGACCAT  CATCGCCGGC  ATGCTCTCCG  ACCGCTTTTT  CAAACGCAAC  CGCAGCGTGA    120
TGGCCGGATT  CATCAGCCTG  CTGAACACCG  CCGGCTTCGC  CCTGATGCTC  TGGTCGCCGC    180
ACAATTACTA  CACTGATATT  CTGGCGATGA  TTATCTTCGG  GGCCACCATT  GGCGCTCTGA    240
CCTGCTTCCT  TGGCGGGCTG  ATCGCCGTCG  ATATCTCTTC  GCGCAAGGCC  GCCGGGGCCG    300
CGCTCGGCAC  CATCGGCATC  GCAGCTACGC  CGGCGCCGGC  CTGGGCGAGT  TTCTCACCGG    360
GTTCATTATT  GATAAAACGG  CTATCCTTGA  AAACGGCAAA  ACGCTGTATG  ATTTCAGCAC    420
GTTGGCGCTG  TTCTGGGTGG  GTACGGTCTG  GGTTCNGCGC  TACTCTGTTT  TACCACTGCC    480
GCCATCGTCG  CCCGGCGCCA  TGCCGTCGAA  CGGCAGACCT  CGTTCTCCTC  ATAACCGATT    540
AACGAATAAG  GAAGAAGATA  TGATGCCTGC  AAGACATCAG  GGGCTGTTAC  GCCTGTTTAT    600
CGCCTGCGCG  CTGCCGCTGC  TGGCGCTGCA  ATCTGCCGCC  GCGCGGACT  GGCAGCTGGA     660
GAAAGTGGTC  GAGCTCAGCC  GCCACGGTAT  TCGTCCGCCG  ACGGCCGGCA  ACCGGGAAGC    720
CATCGAGGCC  GCCACCGGCC  GACCGTGGAC  CGAGTGGACC  ACCCATGACG  GGGAGCTCAC    780
```

-continued

```
CGGCCATGGC  TATGCCGCCG  TGGTCAACAA  AGGGCGTGCG  GAAGGCCAGC  ATTACCGCCA    840
GCTCGGCCTG  CTGCAGGCCG  GATGCCCGAC  GGCGGAGTCG  ATATACGTGC  GCGCCAGCCC    900
GCTGCAGCGG  ACGCGAGCGA  CCGCCCAGGC  GCTGGTGGAT  GGCGCCTTCC  CCGGCTGCGG    960
CGTCGCTATC  CATTATGTCA  GCGGGGATGC  CGATCCCCTG  TTTCAGACCG  ACAAGTTCGC   1020
CGCCACGCAA  ACCGACCCCG  CCCGCCAGCT  GGCGCGGTGA  AAGAGAAGGC  CGGGGATCTG   1080
GCGCAGGTCG  GCAGGCGCTG  GCGCCGACCA  TCCAGCTATT  GAAACAGGCG  GTTTGTCAGG   1140
CCGATAAGCC  CTGCCCGATC  TTCGATACCC  CGTGGCAGGT  CGAGCAGAGC  AAAAGTGGGA   1200
AGACCACCAT  TAGCGGACTG  AGCGTGATGG  CCAATATGGT  GGAGACGCTG  CGTCTCGGCT   1260
GGAGTGAAAA  CCTGCCTCTC  AGCCAGCTGG  CGTGGGGCAA  GATCACCCAG  GCCAGGCAGA   1320
TCACCGCCCT  GCTGCCGCTG  TTAACGGAAA  ACTACGATCT  GAGTAACGAT  GTGTTGTATA   1380
CCGCGCAAAA  ACGCGGGTCG  GTGCTGCTCA  ACGCTATGCT  CGACGGCGTC  AAACCGGAGC   1440
GAATCGAACG  TACGCTGGCT  GCTGCTGGTG  GCCATGACAC  CAATATCGCC  ATGGTGCGCA   1500
CGCTGATGAA  CTTTAGCTGG  CAGCTGCCGG  GCTACAGCCG  GGGAAATATC  CCGCCGGGCA   1560
GCAGCCTGGT  GCTGGAGCGC  TGGCGCAACG  CGAAGAGCGG  AGAACGCTAT  CTGCGGGTCT   1620
ATTTCCAGGC  CCAGGGCCTC  GACGACCTGC  GTCGTCTGCA  GACGCCGGAC  GCGCAGACCC   1680
CGATGCTGCG  TCAGGAGTGG  CATCAGCCGG  GCTGCCGTCA  GACCGATGTC  GGTACGCTGT   1740
GTCCTTCCA   GGCGGCTATT  ACCGCCCTCG  GTCAGCGTAT  CGACCGATCA  TCCGCCCCGG   1800
CGGTAGCATG  GTCCTGCCGT  AGCGGCGCGG  TGTTTGTCCG  GGCCCGGGAA  AACCTTTTT   1860
TCCAGGCCGG  CACGACGTCC  GTTATCCGTT  GTCCGGCGCA  AACGCCCCGG  CGGCGACCTG   1920
CGCCGGGGTG  ACACCCGCTG  TCCAGCACCC  AGCCGCTTAT  CAGCCCAGCA  GGCGTGACGT   1980
CGAACGCCGG  ATTGTAAACG  GTGGCCCCCG  TCGGCGCCCA  CTGTACCGCG  CCGAAGCTGC   2040
CCGCCACTCC  GGTCACTTCC  GCCGCCGCGC  GCTGCTCAAT  GGGGATCGCC  GCCCCGTTCG   2100
GGCAATGGCG  GTCGAGGGTG  GTCTGCGGGG  CAGCGACGTA  AAACGGGATC  TGGTGATAAT   2160
GGGCCAAAAC  CGCCAGAGAA  TAGGTGCCGA  TTTTATTCGC  CACGTCGCCG  TTGGCGGCGA   2220
TACGGTCGGC  GCCGACCCAC  ACCGCATCCA  CCTGCCCCTG  CGCCATCAGG  CTGGCGGCCA   2280
TTGAATCGGC  GATCAGCTGA  TAGGGCACGC  CCAGCTCGCC  CAGCTCCCAG  GCGGTTAAAC   2340
GACCGCCCTG  CAGCAGCGGC  CGGGTTTCAT  CAACCCATAC  GTTGGTCACT  TTTCCCTGCC   2400
GGTGCGCCAG  CGCGATAACG  CCGAGGGCGG  TCCCTACCCC  GGCGGTCGCC  AGGCCACCGG   2460
TGTTGCAGTG  GGTCAGCAGT  CGACTGCCGG  GCTTCACCAG  CGCACTGCCC  GCCTCAGCGA   2520
TGCGGTCGCA  CAGCTGTTTA  TCTTCTTCGA  CCAGACGCAA  GGCTTCCGCT  TCCAGCGCCT   2580
GCGGGTAATC  TCCGGGCCAG  CGCTGCTTCA  TGCGATCAGA  TTATTCATCA  GGTTGACCGC   2640
CGTCGGCCGC  GCCGCGCGCA  GTCTCCAGCG  CCTGCTGGAG  TGCATCCCGG  TTCAGGCCGC   2700
GCTGGGCCAG  CAGGGCCAGC  AGCAGGCTGG  CGGACAGGCC  AATCAGCGGC  GCGCCGCGCA   2760
CCCCGCAGGT  ATGAATATGG  TCCACCAGCA  GCGCAACGTT  ATCCGCCGCC  AGCCAGCGTT   2820
TTTCCTGCGG  CAAGGCCTGC  TGGTCGAGAA  TAAAAAGCTG  ATTTTCACTC  ACCCGCAGGC   2880
TGGTGGTCTG  TAATGTCTGC  ATGTCGTTAA  ATCCCTGTTG  CGTTGTTGTA  TCACATTGTG   2940
TCAGGATGGA  ATCCAGAAGT  ATAGACGTCT  GAACGGCTTA  ATCAGAATTC  GAGGATCGAG   3000
GCAATGTCGC  AATACCATAC  CTTCACCGCC  CACGATGCCG  TGGCTTACGC  GCAGAGTTTC   3060
GCCGGCATCG  ACANCCATCT  GAGCTGGTCA  GCGCGCAGGA  AGTGGGCGAT  GCAACTCAA   3120
TCTGGTGTTT  AAAGTGTTCG  ATCGCCAGGG  CGTCACGGGC  GATCGTCAAA  CAGGCTCTGC   3180
```

-continued

| | | | | | |
|---|---|---|---|---|---|
| CCTACGTGCG | CTGCGTCGGC | GAATCCTGGC | CGCTGACCCT | CGACCGCGCC | CGTCTCGAAG | 3240 |
| CGCAGACCCT | GGTCGCCCAC | TATCAGCACA | GCCCGCAGCA | CACGGTAAAA | ATCCATCACT | 3300 |
| TTGATCCCGA | GCTGGCGGTG | ATGGTGATGG | AAGATCTTTC | CGACCACCGC | ATCTTGCGCG | 3360 |
| GAGAGCTTAT | CGCTAACGTC | TACTATCCCC | AGGCGGCCCG | CCAGCTTGGC | GACTATCTGG | 3420 |
| CGCAGGTGCT | GTTTCACACC | AGCGATTTCT | ACCTCCATCC | CCACGAGAAA | AAGGCGCAGG | 3480 |
| TGGCGCAGTT | TATTAACCCG | GCGATGTGCG | AGATCACCGA | GGATCTGTTC | TTTAACGACC | 3540 |
| CGTATCAGAT | CCACGAGCGC | AATAACTACC | CGGCGGAGCT | GGGAGGCCGA | TGTCGCCGCC | 3600 |
| CTGCGCGACG | ACGCTCAGCT | TAAGCTGGCG | GTGGCGGCGC | TGAAGCACCG | TTTCTTTGCC | 3660 |
| CATGCGGAAG | CGCTGCTGCA | CGGCGATATC | CACAGCGGGT | CGATCTTCGT | TGCCGAAGGC | 3720 |
| AGCCTGAAGG | CCATCGACGC | CGAGTTCGGC | TACTTCGGCC | CCATTGGCTT | CGATATCGGC | 3780 |
| ACCGCCATCG | GCAACCTGCT | GCTTAACTAC | TGCGGCCTGC | CGGGCCAGCT | CGGCATTCGC | 3840 |
| GATGCCGCCG | CCGCGCGCGA | GCAGCGGCTG | AACGACATCC | ACCAGCTGTG | GACCACCTTT | 3900 |
| GCCGAGCGCT | TCCAGGCGCT | GGCGGCGGAG | AAAACCCGCG | ACGCGGCGCT | GGCTTACCCC | 3960 |
| GGCTATGCCT | CCGCCTTTCT | GAAAAAGGTG | TGGGCGGACG | CGGTCGGCTT | CTGCGGCAGC | 4020 |
| GAACTGATCC | GCCGCAGCGT | CGGACTGTCG | CACGTCGCGG | ATATCGACAC | TATCCAGGAC | 4080 |
| GACGCCATGC | GTCATGAGTG | CCTGCGCCAC | GCCATTACCC | TGGGCAGAGC | GCTGATCGTG | 4140 |
| CTGGCCGAGC | GTATCGACAG | CGTCGACGAG | CTGCTGGCGN | GGGTACGCCA | GTACAGCTGA | 4200 |
| GTGCGCCTGT | TTCCCTCACC | CCAACCCTCT | CCCACAGGGA | GAGGGAGCAC | CCCCTAAAAA | 4260 |
| AGTGCCATTT | TCTGGGATTG | CCCGGCGNGN | TGCGCTTGCC | GGGCCTACAG | ATAGCCGCAT | 4320 |
| AACGGTTTGA | TCTTGCACTC | TTTCGTAGGC | CGGGTAAGGC | GAAAGCCGCC | ACCCGGCAGA | 4380 |
| CATGCGAGTA | CAATTTTGCA | TTTACCTTAC | CCTCACCCCA | GATACTCAAT | CACCGATAGC | 4440 |
| CCGCCGTTGT | AATCGGTGCT | GTAGATAATG | CCTTGCGCAT | CGACAAACAC | GTCACAGGAC | 4500 |
| TGGATCACCC | GCGGGCGGCC | GGGACGGGTA | TCCATCATTC | TCTCAGCGCA | GCCGGCACCA | 4560 |
| GCGCCCCGGT | CTCCAGCGGG | CGATACGGGT | TGGAAATGTC | GTAAGCCCGC | ACGCCGGCAT | 4620 |
| TCTGATACGT | GGCAAAAATC | AGCGTTGAGC | TGACAAAGCT | CCCCGGCCGG | TTCTCATGCA | 4680 |
| GGTTGTGCGG | ACCGAAATGC | GCCCCTTTCG | CCACGTAATC | CGCTTCATCC | GGCGGCGGGA | 4740 |
| AGGTGGCGAT | GCTCACCGGG | TTGGTTGGCT | CGCGGATATC | AAACAGCCAG | ATCAGCTTCT | 4800 |
| CGCCGTCCTC | CTGGTTATCG | AGCACCGCTT | CATCCAGCAC | CACCAGCAGA | TCGCGATCCG | 4860 |
| GCAGCGGCAG | CGCGGTATGC | GTTCCGCCGC | CGAACGGCGG | GCTCCAGTTG | CGATGGCTAA | 4920 |
| TCAGCCTCGG | CTGGGTACGG | TCTTTGACAT | CCAGCAGCGT | CAGGCCGCCG | TCGCGCCAGC | 4980 |
| TGCGTAGGCG | TATCCCCGGC | AATAATGGCG | TGATGCAGCG | CATAGCGTTT | GCCCTGCGGC | 5040 |
| CAGTCCGGTG | TTTCACCGCC | CGCCTGGTGC | ATCCCGGCA | GCCACCAGCG | CCCGGCTACT | 5100 |
| TCGGGCTTAC | GCGGATCGGC | CAGATCGATG | GTCAGGAAGA | TGTAGTCGGT | AAAACCGTCG | 5160 |
| ATCAGCGCAG | ACACATACGC | CCAGCGCCCG | CCGACGTACC | AGATGCGGTG | AATACCGATG | 5220 |
| CCGTTAAGCG | ACAGGAAACT | GATTTCCCGC | GCTGCGCGGG | AGTGGAAATA | TCAAAGATGC | 5280 |
| GCAGCCCGGC | GCTCCAGCCC | CTGTCCTGCA | CATCGCTGAC | CGTGTCACCC | ACCGAGCGGG | 5340 |
| TGTAGTACAC | CTTCTCATCA | GCAAAACGGG | CGTCAGCAAA | CAGATCCCGG | GCGTTGATCA | 5400 |
| CCAGCAGCAG | ATCGTCATGC | GCCTGGAGTG | CACGTTCCAG | GTGCCCGGCG | GCGCGGCAAT | 5460 |
| ATAGTTGACG | GTGGTGGGCC | GGGTCGGATC | GCAACATCG | ACCACGGAAA | AACCCTGCGA | 5520 |
| CACCATATGG | CCGATATAGG | CGAATCCGCG | GTGCACCATC | AGCTGCACGC | CGTCCGGACG | 5580 |

| | | | | | |
|---|---|---|---|---|---|
| ACCGCCCTGA | TCGCTATGGC | CAATCAGCCG | CATATTGCGG | CTGTATTCGG | GGGAAGGTAA | 5640 |
| TGCTGACATA | GGGGATCCCT | CTCGCCCGGT | GGCATGGTTT | TCCCCCCTCT | CCTGCGGAGA | 5700 |
| GGGCCGGGGC | GAGGGCACCA | GGCCGCCGCC | CACCGCCACC | CGGCTTGATT | TTATTTGTTC | 5760 |
| TTCGCTTCCA | GCGTCGCGAA | CCACGGCGCG | ATAAAGTCTT | CGGTCTGGCC | CCAGCCAGGG | 5820 |
| ATAATTTTCC | CCAGCGACGC | CACGTTTACC | GCTCCCGGCT | GGGCCGCCAG | CAGCGCCTGG | 5880 |
| GGAATCGCTG | CCGCCTTGAA | GTCGTAGGTG | GCTGGCGTCG | GCTCGCCGGC | GATCTTGTTG | 5940 |
| GCGATCAGCC | GCACGTTGGT | CGCGCCGATA | AGCTT | | | 5975 |

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:24:

CGACGTTGTA AAACGACGGC CAGT        2

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:25:

CAGGAAACAG CTATGAC        1